(12) United States Patent
Jahng et al.

(10) Patent No.: US 8,979,900 B2
(45) Date of Patent: Mar. 17, 2015

(54) SPINAL STABILIZATION DEVICE

(75) Inventors: Tae-ahn Jahng, Iksan (KR); Jason Yim, Solana Beach, CA (US); Brian Scott Bowman, Encinitas, CA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1389 days.

(21) Appl. No.: 11/705,953

(22) Filed: Feb. 13, 2007

(65) Prior Publication Data

US 2007/0276380 A1 Nov. 29, 2007

Related U.S. Application Data

(63) Continuation-in-part of application No. 11/072,886, filed on Mar. 3, 2005, now Pat. No. 7,326,210, which is a continuation-in-part of application No. 11/009,097, filed on Dec. 10, 2004, now abandoned, which is a continuation-in-part of application No. 10/798,014, filed on Mar. 10, 2004, now Pat. No. 7,763,052, which is a continuation-in-part of application No. 10/728,566, filed on Dec. 5, 2003, now abandoned.

(30) Foreign Application Priority Data

Sep. 24, 2003 (KR) .............................. 2003-0066108

(51) Int. Cl.
*A61B 17/70* (2006.01)
*A61B 17/88* (2006.01)
(Continued)

(52) U.S. Cl.
CPC ............. *A61B 17/88* (2013.01); *A61B 17/1757* (2013.01); *A61B 17/3421* (2013.01); *A61B 17/3468* (2013.01); *A61B 17/7007* (2013.01); *A61B 19/54* (2013.01); *A61B 17/02* (2013.01); *A61B 17/3423* (2013.01); *A61B 17/3439* (2013.01); *A61B 17/3472* (2013.01); *A61B 17/7004* (2013.01); *A61B 17/701* (2013.01); *A61B 17/7032* (2013.01); *A61B 17/8897* (2013.01); *A61B 2017/00004* (2013.01);
(Continued)

(58) Field of Classification Search
USPC .................................................. 606/250-263
See application file for complete search history.

(56) References Cited

U.S. PATENT DOCUMENTS

| 1,276,117 A | 8/1918 | Riebe |
| 1,985,427 A | 12/1934 | Richardson |

(Continued)

FOREIGN PATENT DOCUMENTS

| CA | 2600672 | 9/2006 |
| CH | 675531 | 10/1992 |

(Continued)

OTHER PUBLICATIONS

International Preliminary Report on Patentability for PCT/US2005/044372, mailed Jun. 21, 2007, 4 pages.
Kanayama et al., Journal of Neurosurgery (2001) 95(Spine 1):5-10.
Markwalder and Wenger, Acta Neurochirurgica (2003) 145(3):209-214.
Mulholland and Sengupta, European Spine Journal (2002) 11 (Suppl 2):S198-205.
Schmoelz et al., Journal of Spinal Disorders & Techniques (2003) 16(4):418-423.

(Continued)

*Primary Examiner* — Mary Hoffman
(74) *Attorney, Agent, or Firm* — Baker & Hostetler LLP

(57) ABSTRACT

A flexible connection unit for use in a spinal fixation device that includes: a longitudinal member having first and second ends and a flexible member interposed between the first and second ends, at least one of the first end and second end configured to be engaged by a first bone securing member; and at least one spacer located between the first and second ends, the spacer comprising a resilient element and a ring element encircling at least a portion of the resilient element, wherein the ring element is configured to be engaged by a second bone securing member.

27 Claims, 45 Drawing Sheets

(51) Int. Cl.
  *A61B 17/17* (2006.01)
  *A61B 17/34* (2006.01)
  *A61B 19/00* (2006.01)
  *A61B 17/02* (2006.01)
  *A61B 17/00* (2006.01)

(52) U.S. Cl.
  CPC .......... *A61B2017/00862* (2013.01); *A61B 2017/0256* (2013.01); *A61B 2019/5287* (2013.01); *A61B 2019/5416* (2013.01); *A61B 2019/5487* (2013.01)
  USPC ............ 606/255; 606/259; 606/263

(56) References Cited

U.S. PATENT DOCUMENTS

| | | |
|---|---|---|
| 2,134,197 A | 10/1938 | Miller |
| 2,379,577 A | 7/1945 | Harsted |
| 2,546,026 A | 3/1951 | Coon |
| 2,554,708 A | 5/1951 | Kosten |
| 2,805,441 A | 9/1957 | Reder |
| 2,845,748 A | 8/1958 | Derham |
| 2,895,594 A | 7/1959 | Smith |
| 2,995,151 A | 8/1961 | Lockwood |
| 3,019,552 A | 2/1962 | Schleich |
| 3,028,291 A | 4/1962 | Roberts et al. |
| 3,263,949 A | 8/1966 | Conrad |
| 3,325,327 A | 6/1967 | Swan |
| 3,364,807 A | 1/1968 | Holton |
| 3,401,607 A | 9/1968 | Wortman |
| 3,463,148 A | 8/1969 | Treace |
| 3,575,194 A | 4/1971 | McMurry |
| 3,575,195 A | 4/1971 | McMurry |
| 3,635,233 A | 1/1972 | Robertson |
| 3,669,133 A | 6/1972 | Hyman |
| 3,715,454 A | 2/1973 | Kleykamp |
| 3,741,205 A | 6/1973 | Markolf |
| 3,744,488 A | 7/1973 | Cox |
| 3,858,578 A | 1/1975 | Milo |
| 3,996,834 A | 12/1976 | Reynolds |
| 3,999,730 A | 12/1976 | Consalves et al. |
| 4,041,939 A | 8/1977 | Hall |
| 4,047,523 A | 9/1977 | Hall |
| 4,301,551 A | 11/1981 | Dore et al. |
| 4,338,926 A | 7/1982 | Kummer et al. |
| 4,369,769 A | 1/1983 | Edwards |
| 4,378,712 A | 4/1983 | Yoshifuji |
| 4,409,968 A | 10/1983 | Drummond |
| 4,422,451 A | 12/1983 | Kalamchi |
| 4,448,191 A | 5/1984 | Rodnyansky et al. |
| 4,483,562 A | 11/1984 | Schoolman |
| 4,493,317 A | 1/1985 | Klaue |
| 4,573,448 A | 3/1986 | Kambin |
| RE32,650 E | 4/1988 | Waddell |
| 4,743,260 A | 5/1988 | Burton |
| 4,748,260 A | 5/1988 | Marlett |
| 4,773,402 A | 9/1988 | Asher et al. |
| 4,911,346 A | 3/1990 | Shallman |
| 4,932,975 A | 6/1990 | Main et al. |
| 4,949,927 A | 8/1990 | Madocks et al. |
| 4,960,410 A | 10/1990 | Pinchuk |
| 4,979,531 A | 12/1990 | Toor et al. |
| 5,002,576 A | 3/1991 | Fuhrmann et al. |
| 5,011,497 A | 4/1991 | Persson et al. |
| 5,029,847 A | 7/1991 | Ross |
| 5,030,220 A | 7/1991 | Howland |
| 5,055,104 A | 10/1991 | Ray |
| 5,084,048 A | 1/1992 | Jacob et al. |
| 5,092,867 A | 3/1992 | Harms et al. |
| 5,133,716 A | 7/1992 | Plaza |
| 5,147,361 A | 9/1992 | Ojima et al. |
| 5,180,393 A | 1/1993 | Commarmond |
| 5,194,678 A | 3/1993 | Kramer |
| 5,215,338 A | 6/1993 | Kimura et al. |
| 5,246,442 A | 9/1993 | Ashman et al. |
| 5,251,611 A | 10/1993 | Zehel et al. |
| 5,261,908 A | 11/1993 | Campbell, Jr. |
| 5,282,863 A | 2/1994 | Burton |
| 5,306,275 A | 4/1994 | Bryan |
| 5,353,843 A | 10/1994 | Hoag |
| 5,375,823 A | 12/1994 | Navas |
| 5,387,213 A | 2/1995 | Breard et al. |
| 5,413,576 A | 5/1995 | Rivard |
| 5,415,661 A | 5/1995 | Holmes |
| 5,423,816 A | 6/1995 | Lin |
| 5,423,820 A | 6/1995 | Miller et al. |
| 5,445,471 A | 8/1995 | Wexler et al. |
| 5,468,241 A | 11/1995 | Metz-Stavenhagen et al. |
| 5,480,401 A | 1/1996 | Navas |
| 5,486,174 A | 1/1996 | Fournet-Fayard et al. |
| 5,488,761 A | 2/1996 | Leone |
| 5,507,812 A | 4/1996 | Moore |
| 5,534,032 A | 7/1996 | Hodorek |
| 5,536,268 A | 7/1996 | Griss |
| 5,540,688 A | 7/1996 | Navas |
| 5,558,674 A | 9/1996 | Heggeness et al. |
| 5,562,660 A | 10/1996 | Grob |
| 5,562,737 A | 10/1996 | Graf |
| 5,573,520 A | 11/1996 | Schwartz et al. |
| 5,601,553 A | 2/1997 | Trebing et al. |
| 5,607,428 A | 3/1997 | Lin |
| 5,620,445 A | 4/1997 | Brosnahan et al. |
| 5,649,925 A | 7/1997 | Alacreu |
| 5,658,286 A | 8/1997 | Sava |
| 5,662,300 A | 9/1997 | Michelson |
| 5,662,651 A | 9/1997 | Tornier et al. |
| 5,665,092 A | 9/1997 | Mangiardi et al. |
| 5,672,175 A * | 9/1997 | Martin ............ 606/86 A |
| 5,681,311 A | 10/1997 | Foley et al. |
| 5,688,275 A | 11/1997 | Koros et al. |
| 5,709,686 A | 1/1998 | Talos et al. |
| 5,713,900 A | 2/1998 | Benzel et al. |
| 5,725,582 A | 3/1998 | Bevan et al. |
| 5,733,284 A | 3/1998 | Martin |
| 5,785,713 A | 7/1998 | Jobe |
| 5,810,306 A | 9/1998 | Hung et al. |
| 5,810,823 A | 9/1998 | Klaue et al. |
| 5,814,046 A | 9/1998 | Hopf |
| RE36,221 E | 6/1999 | Breard et al. |
| 5,938,663 A | 8/1999 | Petreto |
| 5,944,719 A | 8/1999 | Leban |
| 5,961,524 A | 10/1999 | Crombie |
| 5,964,767 A | 10/1999 | Tapia et al. |
| 6,010,162 A | 1/2000 | Grau et al. |
| 6,015,409 A | 1/2000 | Jackson |
| 6,030,162 A | 2/2000 | Huebner |
| 6,053,922 A | 4/2000 | Krause et al. |
| 6,099,528 A | 8/2000 | Saurat |
| 6,102,912 A | 8/2000 | Cazin et al. |
| 6,162,223 A | 12/2000 | Orsak et al. |
| 6,175,758 B1 | 1/2001 | Kambin |
| 6,187,000 B1 | 2/2001 | Davison et al. |
| 6,193,720 B1 | 2/2001 | Yuan et al. |
| 6,203,437 B1 | 3/2001 | Durie et al. |
| 6,206,881 B1 | 3/2001 | Frigg et al. |
| 6,241,730 B1 | 6/2001 | Alby |
| 6,267,764 B1 | 7/2001 | Elberg |
| 6,290,700 B1 | 9/2001 | Schmotzer |
| 6,293,949 B1 | 9/2001 | Justis et al. |
| 6,296,644 B1 | 10/2001 | Saurat et al. |
| 6,328,047 B1 | 12/2001 | Lee |
| 6,337,142 B2 | 1/2002 | Harder et al. |
| 6,342,055 B1 | 1/2002 | Eisermann et al. |
| 6,355,038 B1 | 3/2002 | Pisharodi |
| 6,402,750 B1 | 6/2002 | Atkinson et al. |
| 6,440,169 B1 | 8/2002 | Elberg et al. |
| 6,447,518 B1 | 9/2002 | Krause et al. |
| 6,447,546 B1 | 9/2002 | Bramlet et al. |
| 6,468,278 B1 | 10/2002 | Muckter |
| 6,468,279 B1 | 10/2002 | Reo |
| 6,475,220 B1 | 11/2002 | Whiteside |
| 6,475,242 B1 | 11/2002 | Bramlet |
| 6,488,682 B2 | 12/2002 | Kikuchi et al. |
| 6,520,495 B1 | 2/2003 | Le Mendola |

(56) References Cited

U.S. PATENT DOCUMENTS

| | | |
|---|---|---|
| 6,530,929 B1 | 3/2003 | Justis et al. |
| 6,530,934 B1 | 3/2003 | Jacobsen et al. |
| 6,554,831 B1 | 4/2003 | Rivard et al. |
| 6,558,390 B2 | 5/2003 | Cragg |
| 6,575,979 B1 | 6/2003 | Cragg |
| 6,576,018 B1 | 6/2003 | Holt |
| 6,585,769 B1 | 7/2003 | Muhanna et al. |
| 6,589,246 B1 | 7/2003 | Hack et al. |
| 6,596,008 B1 | 7/2003 | Kambin |
| 6,626,905 B1 | 9/2003 | Schmiel et al. |
| 6,626,909 B2 | 9/2003 | Chin |
| 6,645,207 B2 | 11/2003 | Dixon et al. |
| 6,652,585 B2 | 11/2003 | Lange |
| 6,682,533 B1 | 1/2004 | Dinsdale et al. |
| 6,706,044 B2 | 3/2004 | Kuslich et al. |
| 6,749,614 B2 | 6/2004 | Teitelbaum et al. |
| 6,783,527 B2 | 8/2004 | Drewry et al. |
| 6,821,277 B2 | 11/2004 | Teitelbaum |
| 6,827,743 B2 | 12/2004 | Eisermann et al. |
| 6,835,205 B2 | 12/2004 | Atkinson et al. |
| 6,884,241 B2 | 4/2005 | Bertranou et al. |
| 6,966,910 B2 | 11/2005 | Ritland |
| 6,974,461 B1 | 12/2005 | Wolter |
| 6,986,771 B2 | 1/2006 | Paul et al. |
| 6,989,011 B2 | 1/2006 | Paul et al. |
| RE38,983 E | 2/2006 | Antonious |
| 7,083,621 B2 | 8/2006 | Shaolian et al. |
| 7,094,237 B2 | 8/2006 | Gradel et al. |
| 7,097,648 B1 | 8/2006 | Globerman et al. |
| 7,125,410 B2 | 10/2006 | Freudiger |
| 7,137,985 B2 | 11/2006 | Jahng |
| 7,229,441 B2 | 6/2007 | Trieu et al. |
| 7,326,210 B2 | 2/2008 | Jahng et al. |
| 7,329,258 B2 | 2/2008 | Studer |
| 7,335,200 B2 | 2/2008 | Carli |
| 7,377,921 B2 | 5/2008 | Studer et al. |
| 7,556,639 B2 | 7/2009 | Rothman et al. |
| 7,611,518 B2 | 11/2009 | Walder et al. |
| 7,621,912 B2 | 11/2009 | Harms et al. |
| 7,651,515 B2 | 1/2010 | Mack et al. |
| 7,717,941 B2 | 5/2010 | Petit |
| 7,763,052 B2 | 7/2010 | Jahng |
| 7,815,665 B2 | 10/2010 | Jahng et al. |
| 7,993,370 B2 | 8/2011 | Jahng |
| 8,231,657 B2 | 7/2012 | Eckhardt et al. |
| 8,292,925 B2 | 10/2012 | Hestad et al. |
| 8,623,057 B2 | 1/2014 | Jahng et al. |
| 2001/0020169 A1 | 9/2001 | Metz-Stavenhagen |
| 2001/0037111 A1 | 11/2001 | Dixon et al. |
| 2001/0049559 A1 | 12/2001 | Koo et al. |
| 2002/0010467 A1 | 1/2002 | Cooper et al. |
| 2002/0035366 A1 | 3/2002 | Walder et al. |
| 2002/0049394 A1 | 4/2002 | Roy et al. |
| 2002/0055740 A1 | 5/2002 | Lieberman |
| 2002/0065557 A1 | 5/2002 | Goble et al. |
| 2002/0082600 A1 | 6/2002 | Shaolian et al. |
| 2002/0087159 A1 | 7/2002 | Thomas |
| 2002/0095154 A1 | 7/2002 | Atkinson et al. |
| 2002/0099378 A1 | 7/2002 | Michelson |
| 2002/0107570 A1 | 8/2002 | Sybert et al. |
| 2002/0111628 A1 | 8/2002 | Ralph et al. |
| 2002/0111630 A1 | 8/2002 | Ralph et al. |
| 2002/0120270 A1 | 8/2002 | Trieu et al. |
| 2002/0123668 A1 | 9/2002 | Ritland |
| 2002/0123750 A1 | 9/2002 | Eisermann et al. |
| 2002/0123806 A1 | 9/2002 | Reiley |
| 2002/0133155 A1 | 9/2002 | Ferree |
| 2002/0138077 A1 | 9/2002 | Ferree |
| 2002/0143329 A1 | 10/2002 | Serhan et al. |
| 2002/0143401 A1 | 10/2002 | Michelson |
| 2002/0169450 A1 | 11/2002 | Lange |
| 2002/0183748 A1 | 12/2002 | Martin et al. |
| 2002/0198526 A1 | 12/2002 | Shaolian et al. |
| 2003/0032958 A1 | 2/2003 | Soubeiran et al. |
| 2003/0040746 A1 | 2/2003 | Mitchell et al. |
| 2003/0040797 A1 | 2/2003 | Fallin et al. |
| 2003/0045875 A1 | 3/2003 | Bertranou et al. |
| 2003/0055426 A1 | 3/2003 | Carbone et al. |
| 2003/0060823 A1 | 3/2003 | Bryan |
| 2003/0073998 A1 | 4/2003 | Pagliuca et al. |
| 2003/0083657 A1 | 5/2003 | Drewry et al. |
| 2003/0083688 A1 | 5/2003 | Simonson |
| 2003/0088251 A1 | 5/2003 | Braun et al. |
| 2003/0093078 A1 | 5/2003 | Ritland |
| 2003/0109880 A1 | 6/2003 | Shirado et al. |
| 2003/0171749 A1 | 9/2003 | Le Couedic et al. |
| 2003/0191371 A1 | 10/2003 | Smith et al. |
| 2003/0191470 A1 | 10/2003 | Ritland |
| 2003/0195514 A1 | 10/2003 | Trieu et al. |
| 2003/0195551 A1 | 10/2003 | Davison et al. |
| 2003/0220643 A1 | 11/2003 | Ferree |
| 2004/0002708 A1 | 1/2004 | Ritland |
| 2004/0049189 A1 | 3/2004 | Le Couedic et al. |
| 2004/0049190 A1 | 3/2004 | Biedermann et al. |
| 2004/0138661 A1 | 7/2004 | Bailey |
| 2004/0138662 A1 | 7/2004 | Landry et al. |
| 2004/0143264 A1 | 7/2004 | McAfee |
| 2004/0147928 A1 | 7/2004 | Landry et al. |
| 2004/0172025 A1 | 9/2004 | Drewry et al. |
| 2004/0215191 A1 | 10/2004 | Kitchen |
| 2004/0215193 A1 | 10/2004 | Shaolian et al. |
| 2004/0236327 A1* | 11/2004 | Paul et al. ............... 606/61 |
| 2004/0236328 A1 | 11/2004 | Paul et al. |
| 2004/0236329 A1 | 11/2004 | Panjabi |
| 2004/0267260 A1 | 12/2004 | Mack et al. |
| 2005/0021029 A1 | 1/2005 | Trieu et al. |
| 2005/0033295 A1 | 2/2005 | Wisnewski |
| 2005/0033299 A1 | 2/2005 | Shluzas |
| 2005/0038432 A1 | 2/2005 | Shaolian et al. |
| 2005/0049708 A1* | 3/2005 | Atkinson et al. ............ 623/17.16 |
| 2005/0059976 A1 | 3/2005 | Bryan et al. |
| 2005/0065514 A1 | 3/2005 | Studer |
| 2005/0065516 A1 | 3/2005 | Jahng |
| 2005/0085815 A1* | 4/2005 | Harms et al. ............... 606/61 |
| 2005/0090822 A1 | 4/2005 | DiPoto |
| 2005/0101957 A1 | 5/2005 | Buskirk et al. |
| 2005/0113927 A1 | 5/2005 | Malek |
| 2005/0124991 A1 | 6/2005 | Jahng |
| 2005/0131407 A1 | 6/2005 | Sicvol et al. |
| 2005/0149020 A1 | 7/2005 | Jahng et al. |
| 2005/0154390 A1 | 7/2005 | Biedermann et al. |
| 2005/0165396 A1* | 7/2005 | Fortin et al. ............... 606/61 |
| 2005/0171539 A1 | 8/2005 | Braun et al. |
| 2005/0171540 A1 | 8/2005 | Lim et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0182401 A1 | 8/2005 | Timm et al. |
| 2005/0182409 A1 | 8/2005 | Callahan et al. |
| 2005/0197660 A1 | 9/2005 | Haid et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0203519 A1* | 9/2005 | Harms et al. ............... 606/61 |
| 2005/0222569 A1 | 10/2005 | Panjabi |
| 2005/0228381 A1 | 10/2005 | Kirschman |
| 2005/0245930 A1 | 11/2005 | Timm et al. |
| 2005/0261682 A1 | 11/2005 | Ferree |
| 2005/0261685 A1 | 11/2005 | Fortin et al. |
| 2005/0261686 A1 | 11/2005 | Paul |
| 2005/0277922 A1 | 12/2005 | Trieu et al. |
| 2005/0288670 A1 | 12/2005 | Panjabi et al. |
| 2005/0288672 A1 | 12/2005 | Ferree |
| 2006/0009768 A1 | 1/2006 | Ritland |
| 2006/0015100 A1 | 1/2006 | Panjabi et al. |
| 2006/0036240 A1 | 2/2006 | Colleran et al. |
| 2006/0084982 A1 | 4/2006 | Kim |
| 2006/0084984 A1 | 4/2006 | Kim |
| 2006/0111715 A1 | 5/2006 | Jackson |
| 2006/0129147 A1 | 6/2006 | Biedermann et al. |
| 2006/0142758 A1 | 6/2006 | Petit |
| 2006/0142760 A1 | 6/2006 | McDonnell |
| 2006/0149228 A1 | 7/2006 | Schlapfer et al. |

(56) References Cited

U.S. PATENT DOCUMENTS

| | | |
|---|---|---|
| 2006/0149238 A1 | 7/2006 | Sherman et al. |
| 2006/0189983 A1 | 8/2006 | Fallin et al. |
| 2006/0189984 A1 | 8/2006 | Fallin et al. |
| 2006/0195093 A1 | 8/2006 | Jahng et al. |
| 2006/0212033 A1 | 9/2006 | Rothman et al. |
| 2006/0229612 A1* | 10/2006 | Rothman et al. ............... 606/61 |
| 2006/0240533 A1 | 10/2006 | Sengupta et al. |
| 2006/0260483 A1 | 11/2006 | Hartmann et al. |
| 2006/0264940 A1 | 11/2006 | Hartmann |
| 2006/0293657 A1 | 12/2006 | Hartmann |
| 2007/0016193 A1 | 1/2007 | Ritland |
| 2007/0055247 A1 | 3/2007 | Jahng et al. |
| 2007/0073293 A1 | 3/2007 | Martz et al. |
| 2007/0118122 A1* | 5/2007 | Butler et al. .................... 606/61 |
| 2007/0123864 A1 | 5/2007 | Walder et al. |
| 2007/0123865 A1 | 5/2007 | Schlapfer et al. |
| 2007/0123871 A1 | 5/2007 | Jahng et al. |
| 2007/0129729 A1 | 6/2007 | Petit et al. |
| 2007/0149909 A1 | 6/2007 | Fortin et al. |
| 2007/0198088 A1 | 8/2007 | Biedermann et al. |
| 2007/0206244 A1 | 9/2007 | Kobayashi et al. |
| 2007/0225710 A1 | 9/2007 | Jahng et al. |
| 2008/0195149 A1 | 8/2008 | Burke |
| 2009/0076553 A1 | 3/2009 | Wolter |
| 2010/0137919 A1 | 6/2010 | Wolter |
| 2011/0106167 A1 | 5/2011 | Jahng |
| 2011/0301643 A1 | 12/2011 | Jahng |
| 2012/0209330 A1 | 8/2012 | Jahng |
| 2014/0094852 A1 | 4/2014 | Jahng |

FOREIGN PATENT DOCUMENTS

| | | |
|---|---|---|
| DE | 2821678 | 11/1979 |
| DE | 4109941 | 10/1992 |
| DE | 4239716 | 8/1994 |
| DE | 4343117 | 6/1995 |
| DE | 19629011 | 1/1998 |
| DE | 19746687 | 5/1999 |
| DE | 10348329 B3 | 2/2005 |
| EP | 266146 | 5/1988 |
| EP | 0553042 | 7/1993 |
| EP | 0677277 | 3/1995 |
| EP | 0669109 | 8/1995 |
| EP | 1281364 | 2/2003 |
| EP | 1488751 | 12/2004 |
| EP | 1677689 | 7/2006 |
| FR | 742618 | 3/1933 |
| FR | 2702363 | 3/1993 |
| FR | 2702363 | 12/1993 |
| FR | 2694182 A1 | 2/1994 |
| FR | 2715825 | 8/1995 |
| FR | 2717370 | 9/1995 |
| FR | 2718946 | 10/1995 |
| FR | 2728158 | 6/1996 |
| FR | 2775583 A1 | 9/1999 |
| FR | 2799949 | 4/2001 |
| FR | 2802796 | 6/2001 |
| GB | 1237405 | 6/1971 |
| GB | 1575194 | 9/1980 |
| GB | 2382304 | 5/2003 |
| JP | 07-008504 | 1/1995 |
| JP | 09108247 | 4/1997 |
| JP | 11290337 | 10/1999 |
| JP | 2000-325358 | 11/2000 |
| JP | 2002224131 | 8/2002 |
| WO | WO 95/05785 | 3/1995 |
| WO | WO97/09000 | 3/1997 |
| WO | WO 01/28436 | 4/2001 |
| WO | WO03/047442 | 6/2003 |
| WO | WO 2004/017817 | 3/2004 |
| WO | WO 2004/069987 | 8/2004 |
| WO | WO 2004/098452 A2 | 11/2004 |
| WO | WO 2004/105577 | 12/2004 |
| WO | WO2005/030029 | 4/2005 |
| WO | WO2005/030031 | 4/2005 |
| WO | WO 2005/039454 | 5/2005 |
| WO | WO 2005/044117 | 5/2005 |
| WO | WO 2005/039454 | 6/2005 |
| WO | WO 2005/092222 | 10/2005 |
| WO | WO 2005/094704 | 10/2005 |
| WO | WO 2005/110257 | 11/2005 |
| WO | WO2006/063107 | 6/2006 |
| WO | WO 2006/063107 | 6/2006 |
| WO | WO2006/071742 | 7/2006 |
| WO | WO 2006/096414 | 9/2006 |
| WO | WO 2008/100944 | 8/2008 |

OTHER PUBLICATIONS

Stoll et al., European Spine Journal (2002) 11 (Suppl 2):S170-178.

International Search Report for PCT/US04/30732, mailed on Oct. 14, 2005, 2 pages.

International Search Report for PCT/US05/44372, mailed on Sep. 20, 2006, 3 pages.

International Search Report for PCT/US05/46659, mailed on Aug. 14, 2006, 3 pages.

"Defendant Globus Medical, Inc.'s Invalidity Contentions", In the United States District Court for the District of Delaware, Case No. 10-300-RMB, filed Apr. 26, 2011, 34 pages.

Kanayma et al., Journal of Neurosurgery, 2001, 95(Spine1), 5-10.

Markwalder et al., Acta Neurochirurgica, 2003, 145(3), 209-214.

Mullholland et al. European Spine Journal, 2002, 11(Suppl. 2), S198-205.

PCT Application No. PCT/US2004/030732, International Search Report, Filing date Sep. 17, 2004, Mailing date Oct. 14, 2005, 2 pages.

PCT Application No. PCT/US2005/044372, International Report on Patentability, Filing date Dec. 9, 2005, Mailing date Jun. 13, 2007, 4 pages.

PCT Application No. PCT/US2005/044372, International Search Report, Filing date Dec. 9, 2005, Mailing date Sep. 20, 2006, 4 pages.

PCT Application No. PCT/US2005/046659, International Search Report, Filing date Dec. 21, 2005, Mailing date Aug. 14, 2006, 3 pages.

Schmoelz et al., "Dynamic Stabilization of the Lumbar Spine and its effects on Adjacent Segments: An In Vitro Experiment", Journal of Spinal Disorders & Techniques, Aug. 2003, 16(4), 418-423.

Stoll et al., European Spine Journal, 2002, 11(Suppl. 2), S170-178.

U.S. Appl. No. 10/977,165: Amendment to the Non-Final Office Action, dated Sep. 22, 2008, 16 pages.

U.S. Appl. No. 10/977,165: Amendment, dated May 7, 2008, 12 pages.

U.S. Appl. No. 10/977,165: Examiner's Interview Summary, dated Dec. 21, 2007, 2 pages.

U.S. Appl. No. 10/977,165: Examiner's Interview Summary, dated Mar. 21, 2008, 4 pages.

U.S. Appl. No. 10/977,165: Examiner's Interview Summary, dated Sep. 25, 2008, 2 pages.

U.S. Appl. No. 10/977,165: Final Office Action, dated Sep. 1, 2009, 8 pages.

U.S. Appl. No. 10/977,165: Non-Final Office Action, dated Mar. 13, 2007, 12 pages.

U.S. Appl. No. 10/977,165: Non-Final Office Action, dated Jan. 8, 2008, 12 pages.

U.S. Appl. No. 10/977,165: Non-Final Office Action, dated Aug. 7, 2008, 10 pages.

U.S. Appl. No. 10/977,165: Response to Office Action, dated Aug. 28, 2007, 14 pages.

Walder et al., "Dynamic Stabilization of Lumbar Motion Segments by Use of Graf's Ligaments with an Average Follow-Up of 7.4 years in 39 Highly selected Consecutive Patients", Acta Neurochirurgica, 2003, 145(3), 209-214.

European Patent Application No. EP12000069: Extended European Search Report dated Apr. 12, 2012, 6 pages.

* cited by examiner

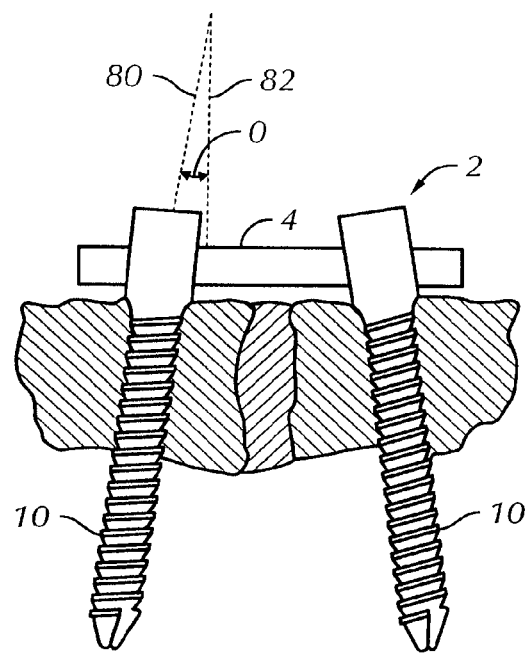
FIG. 23A
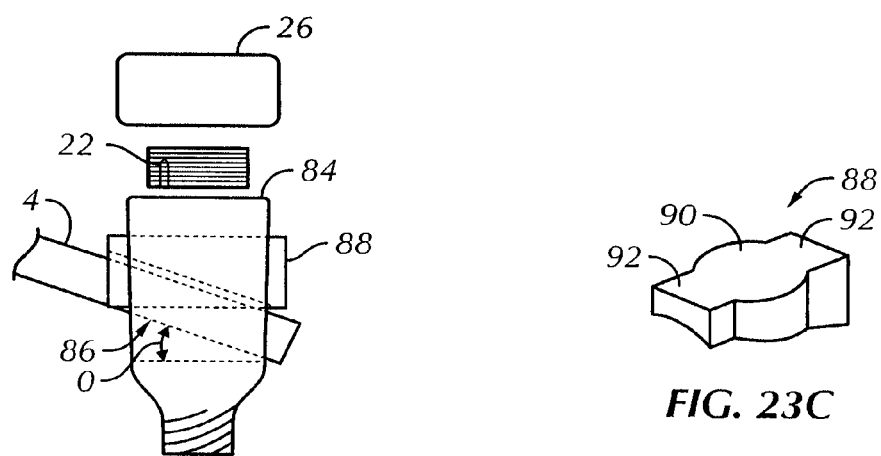
FIG. 23B
FIG. 23C

Uniform Resistance to Bending in All Directions

Easier to Bend in X Direction if Material 279 is Easier to Bend than Material 277

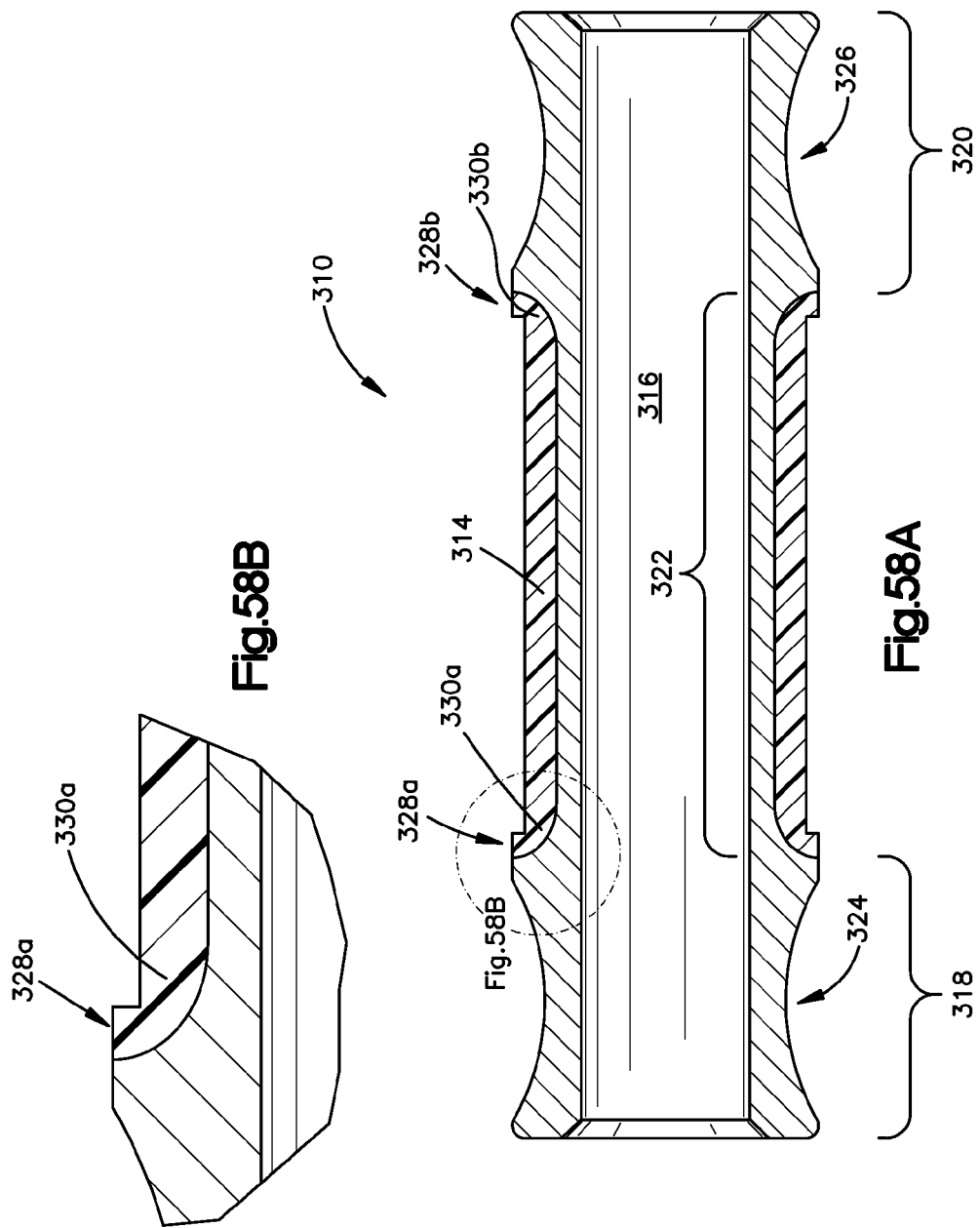

SPINAL STABILIZATION DEVICE

CROSS-REFERENCE TO RELATED APPLICATIONS

The present application is a continuation-in-part of U.S. patent application Ser. No. 11/072,886, filed Mar. 3, 2005, which is a continuation-in-part of U.S. patent application Ser. No. 11/009,097, filed Dec. 10, 2004, which is continuation-in-part of U.S. patent application Ser. No. 10/798,014, filed Mar. 10, 2004, which is a continuation-in-part of U.S. patent application Ser. No. 10/728,566, filed on Dec. 5, 2003, which claims the benefit of priority under 35 U.S.C. §119(a) to Korean Application Serial No. 2003-0066108, filed on Sep. 24, 2003, the entirety of which is incorporated by reference herein.

BACKGROUND OF THE INVENTION

1. Field of the Invention

The present invention relates to a method and system for stabilizing a spinal column and, more particularly, to a method and system of spinal fixation in which one or more screw type securing members are implanted and fixed into a portion of a patient's spinal column and a longitudinal member including flexible, semi-rigid rod-like or plate-like structures of various cross-sections (hereinafter referred to as "rods" or "plates", respectively) are connected and fixed to the upper ends of the securing members to provide stabilization of the spinal column.

2. Description of the Related Art

Degenerative spinal column diseases, such as disc degenerative diseases (DDD), spinal stenosis, spondylolisthesis, and so on, need surgical operation if they do not take a turn for the better by conservative management. Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Conventional methods of spinal fixation utilize a rigid spinal fixation device to support an injured spinal part and prevent movement of the injured part. These conventional spinal fixation devices include: fixing screws configured to be inserted into the spinal pedicle or sacral of the backbone to a predetermined depth and angle, rods or plates configured to be positioned adjacent to the injured spinal part, and coupling elements for connecting and coupling the rods or plates to the fixing screws such that the injured spinal part is supported and held in a relatively fixed position by the rods or plates.

U.S. Pat. No. 6,193,720 discloses a conventional spinal fixation device, in which connection members of a rod or plate type are mounted on the upper ends of at least one or more screws inserted into the spinal pedicle or sacral of the backbone. The connection units, such as the rods and plates, are used to stabilize the injured part of the spinal column which has been weakened by decompression. The connection units also prevent further pain and injury to the patient by substantially restraining the movement of the spinal column. However, because the connection units prevent normal movement of the spinal column, after prolonged use, the spinal fixation device can cause ill effects, such as "junctional syndrome" (transitional syndrome) or "fusion disease" resulting in further complications and abnormalities associated with the spinal column. In particular, due to the high rigidity of the rods or plates used in conventional fixation devices, the patient's fixed joints are not allowed to move after the surgical operation, and the movement of the spinal joints located above or under the operated area is increased. Consequently, such spinal fixation devices cause decreased mobility of the patient and increased stress and instability to the spinal column joints adjacent to the operated area.

It has been reported that excessive rigid spinal fixation is not helpful to the fusion process due to load shielding caused by rigid fixation. Thus, trials using load sharing semi-rigid spinal fixation devices have been performed to eliminate this problem and assist the bone fusion process. For example, U.S. Pat. Nos. 5,672,175, 5,540,688, and U.S. Pub No 2001/0037111 disclose dynamic spine stabilization devices having flexible designs that permit axial load translation (i.e., along the vertical axis of the spine) for bone fusion promotion. However, because these devices are intended for use following a bone fusion procedure, they are not well-suited for spinal fixation without fusion. Thus, in the end result, these devices do not prevent the problem of rigid fixation resulting from fusion.

To solve the above-described problems associated with rigid fixation, non-fusion technologies have been developed. The Graf band is one example of a non-fusion fixation device that is applied after decompression without bone fusion. The Graf band is composed of a polyethylene band and pedicle screws to couple the polyethylene band to the spinal vertebrae requiring stabilization. The primary purpose of the Graf band is to prevent sagittal rotation (flexion instability) of the injured spinal parts. Thus, it is effective in selected cases but is not appropriate for cases that require greater stability and fixation. See, Kanayama et al, Journal of Neurosurgery 95(1 Suppl):5-10, 2001, Markwalder & Wenger, Acta Neurochrgica 145(3):209-14.). Another non-fusion fixation device called "Dynesys" has recently been introduced. See Stoll et al, European Spine Journal 11 Suppl 2:S170-8, 2002, Schmoelz et. al., J. of Spinal Disorder & Techniques 16(4): 418-23, 2003. The Dynesys device is similar to the Graf band except it uses a polycarburethane spacer between the screws to maintain the distance between the heads of two corresponding pedicle screws and, hence, adjacent vertebrae in which the screws are fixed. Early reports by the inventors of the Dynesys device indicate it has been successful in many cases. However, it has not yet been determined whether the Dynesys device can maintain long-term stability with flexibility and durability in a controlled study. Because it has polyethylene components and interfaces, there is a risk of mechanical failure. Furthermore, due to the mechanical configuration of the device, the surgical technique required to attach the device to the spinal column is complex and complicated.

U.S. Pat. Nos. 5,282,863 and 4,748,260 disclose a flexible spinal stabilization system and method using a plastic, non-metallic rod. U.S. patent publication no. 2003/0083657 discloses another example of a flexible spinal stabilization device that uses a flexible elongate member. These devices are flexible but they are not well-suited for enduring long-term axial loading and stress. Additionally, the degree of desired flexibility vs. rigidity may vary from patient to patient. The design of existing flexible fixation devices are not well suited to provide varying levels of flexibility to provide optimum results for each individual candidate. For example, U.S. Pat. No. 5,672,175 discloses a flexible spinal fixation device which utilizes a flexible rod made of metal alloy and/or a composite material. Additionally, compression or extension springs are coiled around the rod for the purpose of providing de-rotation forces on the vertebrae in a desired direction. However, this patent is primarily concerned with providing a spinal fixation device that permits "relative longitudinal translational sliding movement along [the] vertical axis" of the spine and neither teaches nor suggests any particular designs of connection units (e.g., rods or plates) that can provide various flexibility characteristics. Prior flexible rods such as that mentioned in U.S. Pat. No. 5,672,175 typically have solid construction with a relatively small diameter in order to provide a desired level of flexibility. Because they are typically very thin to provide suitable flexibility, such prior art rods are prone to mechanical failure and have been known to break after implantation in patients.

Therefore, conventional spinal fixation devices have not provided a comprehensive and balanced solution to the problems associated with curing spinal diseases. Many of the prior devices are characterized by excessive rigidity, which leads to the problems discussed above while others, though providing some flexibility, are not well-adapted to provide long-term stability and/or varying degrees of flexibility. Therefore, there is a need for an improved dynamic spinal fixation device that provides a desired level of flexibility to the injured parts of the spinal column, while also providing long-term durability and consistent stabilization of the spinal column.

Additionally, in a conventional surgical method for fixing the spinal fixation device to the spinal column, a doctor incises the midline of the back to about 10-15 centimeters, and then, dissects and retracts it to both sides. In this way, the doctor performs muscular dissection to expose the outer part of the facet joint. Next, after the dissection, the doctor finds an entrance point to the spinal pedicle using radiographic devices (e.g., C-arm flouroscopy), and inserts securing members of the spinal fixation device (referred to as "spinal pedicle screws") into the spinal pedicle. Thereafter, the connection units (e.g., rods or plates) are attached to the upper portions of the pedicle screws in order to provide support and stability to the injured portion of the spinal column. Thus, in conventional spinal fixation procedures, the patient's back is incised about 10~15 cm, and as a result, the back muscle, which is important for maintaining the spinal column, is incised or injured, resulting in significant post-operative pain to the patient and a slow recovery period.

Recently, to reduce patient trauma, a minimally invasive surgical procedure has been developed which is capable of performing spinal fixation surgery through a relatively small hole or "window" that is created in the patient's back at the location of the surgical procedure. Through the use of an endoscope, or microscope, minimally invasive surgery allows a much smaller incision of the patient's affected area. Through this smaller incision, two or more securing members (e.g., pedicle screws) of the spinal fixation device are screwed into respective spinal pedicle areas using a navigation system. Thereafter, special tools are used to connect the stabilizing members (e.g., rods or plates) of the fixation device to the securing members. Alternatively, or additionally, the surgical procedure may include inserting a step dilator into the incision and then gradually increasing the diameter of the dilator. Thereafter, a tubular retractor is inserted into the dilated area to retract the patient's muscle and provide a visual field for surgery. After establishing this visual field, decompression and, if desired, fusion procedures may be performed, followed by a fixation procedure, which includes the steps of finding the position of the spinal pedicle, inserting pedicle screws into the spinal pedicle, using an endoscope or a microscope, and securing the stabilization members (e.g., rods or plates) to the pedicle screws in order to stabilize and support the weakened spinal column.

One of the most challenging aspects of performing the minimally invasive spinal fixation procedure is locating the entry point for the pedicle screw under endoscopic or microscopic visualization. Usually anatomical landmarks and/or radiographic devices are used to find the entry point, but clear anatomical relationships are often difficult to identify due to the confined working space. Additionally, the minimally invasive procedure requires that a significant amount of the soft tissue must be removed to reveal the anatomy of the regions for pedicle screw insertion. The removal of this soft tissue results in bleeding in the affected area, thereby adding to the difficulty of finding the correct position to insert the securing members and causing damage to the muscles and soft tissue surrounding the surgical area. Furthermore, because it is difficult to accurately locate the point of insertion for the securing members, conventional procedures are unnecessarily traumatic.

Radiography techniques have been proposed and implemented in an attempt to more accurately and quickly find the position of the spinal pedicle in which the securing members will be inserted. However, it is often difficult to obtain clear images required for finding the corresponding position of the spinal pedicle using radiography techniques due to radiographic interference caused by metallic tools and equipment used during the surgical operation. Moreover, reading and interpreting radiographic images is a complex task requiring significant training and expertise. Radiography poses a further problem in that the patient is exposed to significant amounts of radiation.

Although some guidance systems have been developed which guide the insertion of a pedicle screw to the desired entry point on the spinal pedicle, these prior systems have proven difficult to use and, furthermore, hinder the operation procedure. For example, prior guidance systems for pedicle screw insertion utilize a long wire that is inserted through a guide tube that is inserted through a patient's back muscle and tissue. The location of insertion of the guide tube is determined by radiographic means (e.g., C-arm fluoroscope) and driven until a first end portion of the guide tube reaches the desired location on the surface of the pedicle bone. Thereafter, a first end portion of the guide wire, typically made of a biocompatible metal material, is inserted into the guide tube and pushed into the pedicle bone, while the opposite end of the wire remains protruding out of the patient's back. After the guide wire has been fixed into the pedicle bone, the guide tube is removed, and a hole centered around the guide wire is dilated and retracted. Finally, a pedicle screw having an axial hole or channel configured to receive the guide wire therethrough is guided by the guide wire to the desired location on the pedicle bone, where the pedicle screw is screw-driven into the pedicle.

Although the concept of the wire guidance system is a good one, in practice, the guide wire has been very difficult to use. Because it is a relatively long and thin wire, the structural integrity of the guide wire often fails during attempts to drive one end of the wire into the pedicle bone, making the process unnecessarily time-consuming and laborious. Furthermore, because the wire bends and crimps during insertion, it does not provide a smooth and secure anchor for guiding subsequent tooling and pedicle screws to the entry point on the pedicle. Furthermore, current percutaneous wire guiding systems are used in conjunction with C-arm flouroscopy (or other radiographic device) without direct visualization with the use of an endoscope or microscope. Thus, current wire guidance systems pose a potential risk of misplacement or pedicle breakage. Finally, because one end of the wire remains protruding out of the head of the pedicle screw, and the patient's back, this wire hinders freedom of motion by the surgeon in performing the various subsequent procedures involved in spinal fixation surgery. Thus, there is a need to provide an improved guidance system, adaptable for use in minimally invasive pedicle screw fixation procedures under endoscopic or microscopic visualization, which is easier to implant into the spinal pedicle and will not hinder subsequent procedures performed by the surgeon.

As discussed above, existing methods and devices used to cure spinal diseases are in need of much improvement. Most conventional spinal fixation devices are too rigid and inflexible. This excessive rigidity causes further abnormalities and diseases of the spine, as well as significant discomfort to the patient. Although some existing spinal fixation devices do provide some level of flexibility, these devices are not designed or manufactured so that varying levels of flexibility may be easily obtained to provide a desired level of flexibility for each particular patient. Additionally, prior art devices having flexible connection units (e.g., rods or plates) pose a greater risk of mechanical failure and do not provide long-term durability and stabilization of the spine. Furthermore, existing methods of performing the spinal fixation procedure are unnecessarily traumatic to the patient due to the difficulty in finding the precise location of the spinal pedicle or sacral of the backbone where the spinal fixation device will be secured.

BRIEF SUMMARY OF THE INVENTION

The invention addresses the above and other needs by providing an improved method and system for stabilizing an injured or weakened spinal column.

To overcome the deficiencies of conventional spinal fixation devices, in one embodiment, the inventor of the present invention has invented a novel flexible spinal fixation device with an improved construction and design that is durable and provides a desired level of flexibility and stability.

As a result of long-term studies to reduce the operation time required for minimally invasive spinal surgery, to minimize injury to tissues near the surgical area, in another embodiment, the invention provides a method and device for accurately and quickly finding a position of the spinal column in which securing members of the spinal fixation device will be inserted. A novel guidance/marking device is used to indicate the position in the spinal column where the securing members will be inserted.

BRIEF DESCRIPTION OF THE DRAWINGS

FIG. 23A illustrates a perspective view of two pedicle screws inserted into the pedicles of two adjacent vertebrae at a skewed angle, in accordance with one embodiment of the invention.

FIG. 23B illustrates a structural view of a coupling assembly of a pedicle screw in accordance with one embodiment of the invention.

FIG. 23C provides a perspective view of a slanted stabilizing spacer in accordance with one embodiment of the invention.

FIG. 58 illustrates a cross sectional view of a metal-hybrid spacer in accordance with an embodiment of the present invention.

DETAILED DESCRIPTION OF THE PREFERRED EMBODIMENTS

The invention is described in detail below with reference to the figures wherein like elements are referenced with like numerals throughout.

Figure 1:
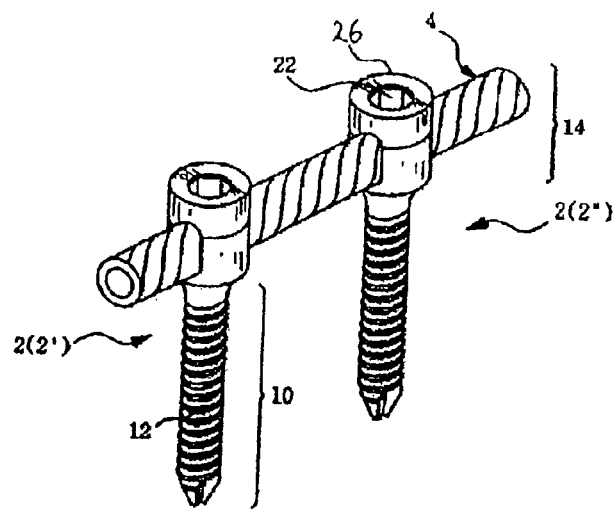
FIG. 1 illustrates a perspective view of a spinal fixation device in accordance with one embodiment of the invention.

FIG. 1 depicts a spinal fixation device in accordance with one embodiment of the present invention. The spinal fixation device includes two securing members 2 (designated as 2' and 2"), and a flexible fixation rod 4 configured to be received and secured within a coupling assembly 14, as described in further detail below with respect to FIG. 3. Each securing member 2 includes a threaded screw-type shaft 10 configured to be inserted and screwed into a patient's spinal pedicle. As shown in FIG. 1, the screw-type shaft 10 includes an external spiral screw thread 12 formed over the length of the shaft 10 and a conical tip at the end of the shaft 10 configured to be inserted into the patient's spinal column at a designated location. Other known forms of the securing member 2 may be used in connection with the present invention provided the securing member 2 can be inserted and fixed into the spinal column and securely coupled to the rod 4.

As described above, the spinal fixation device is used for surgical treatment of spinal diseases by mounting securing members 2 at desired positions in the spinal column. In one embodiment, the rod 4 extends across two or more vertebrae of the spinal column and is secured by the securing members 2 so as to stabilize movement of the two or more vertebrae.

Figure 2:
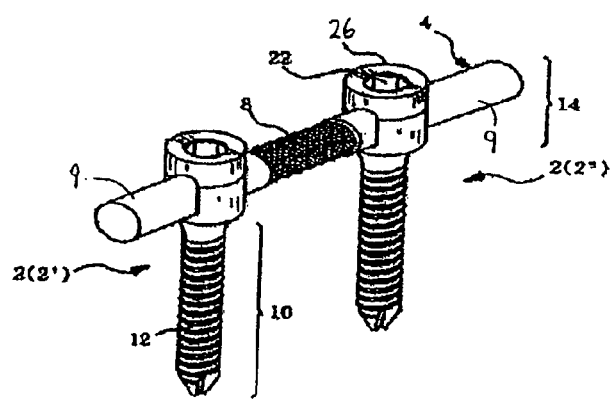
FIG. 2 illustrates a perspective view of spinal fixation device in accordance with another embodiment of the invention.

FIG. 2 illustrates a perspective view of a spinal fixation device in accordance with a further embodiment of the present invention. The spinal fixation device of FIG. 2 is similar to the spinal fixation device of FIG. 1 except that the rod 4 comprises a flexible middle portion 8 juxtaposed between two rigid end portions 9 of the rod 4.

Figure 3:
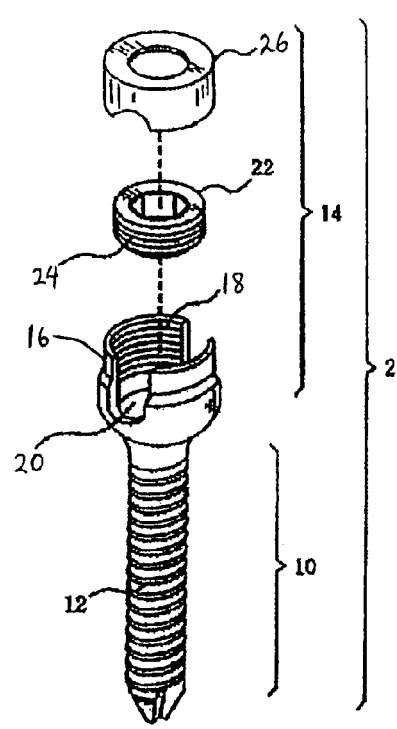
FIG. 3 illustrates an exploded view of the coupling assembly 14 of the pedicle screw 2 of FIGS. 1 and 2, in accordance with one embodiment of the invention.

FIG. 3 provides an exploded view of the securing member 2 of FIGS. 1 and 2 illustrating various components of the coupling assembly 14, in accordance with one embodiment of the invention. As shown in FIG. 3, the coupling assembly 14 includes: a cylindrical head 16 located at a top end of the screw-type shaft 10, a spiral thread or groove 18 formed along portions of the inner wall surface of the cylindrical head 16, and a U-shaped seating groove 20 configured to receive the rod 4 therein. The coupling assembly 14 further comprises an outside-threaded nut 22 having a spiral thread 24 formed on the outside lateral surface of the nut 22, wherein the spiral thread 24 is configured to mate with the internal spiral thread 18 of the cylindrical head 16. In a further embodiment, the coupling assembly 14 includes a fixing cap 26 configured to be mounted over a portion of the cylindrical head 16 to cover and protect the outside-threaded nut 22 and more securely hold rod 4 within seating groove 20. In one embodiment an inner diameter of the fixing gap 26 is configured to securely mate with the outer diameter of the cylindrical head 16. Other methods of securing the fixing cap 26 to the cylindrical head, such as correspondingly located notches and groove (not shown), would be readily apparent to those of skill in the art. In preferred embodiments, the components and parts of the securing member 2 may be made of highly rigid and durable bio-compatible materials such as stainless steel, iron steel, titanium or titanium alloy. Additionally or alternatively, non-metal biocompatible materials may also be utilized such as polymers, elastomers, resins, ceramics, and composites thereof. Such materials are known in the art. As also known in the art, and used herein, "bio-compatible" materials refers to those materials that will not cause any adverse chemical or immunological reactions after being implanted into a patient's body.

Figure 4:
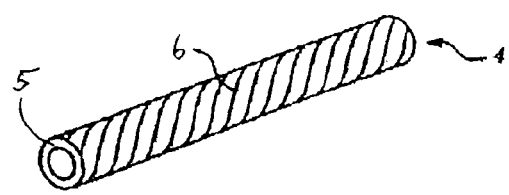
FIG. 4 illustrates a perspective view of a flexible rod connection unit in accordance with one embodiment of the invention.

As shown in FIGS. 1 and 2, in preferred embodiments, the rod 4 is coupled to the securing means 2 by seating the rod 4 horizontally into the seating groove 20 of the coupling means 14 perpendicularly to the direction of the length of the threaded shaft 10 of securing member 2. The outside threaded nut 22 is then received and screwed into the cylindrical head 16 above the rod 4 so as to secure the rod 4 in the seating groove 20. The fixing cap 26 is then placed over the cylindrical head 16 to cover, protect and more firmly secure the components in the internal cavity of the cylindrical head 16. FIGS. 4-7 illustrate perspective views of various embodiments of a rod 4 that may be used in a fixation device, in accordance with the present invention. FIG. 4 illustrates the rod 4 of FIG. 1 wherein the entire rod is made and designed to be flexible. In one embodiment, rod 4 comprises a metal tube or pipe having a cylindrical wall 5 of a predefined thickness. In alternative embodiments, the rod 4 may comprise a tube made from a biocompatible metal-synthetic hybrid material or entirely from a biocompatible synthetic material. Examples of biocompatible metals are: titanium, stainless steel, zirconium, tantalum, cobalt, chromium, nickel and alloys thereof. Examples of biocompatible synthetic materials are: polymers, elastomers, resins, plastics, carbon graphite and composites thereof. Such materials are well known in the art.

In one embodiment, in order to provide flexibility to the rod 4, the cylindrical wall 5 is cut in a spiral fashion along the length of the rod 4 to form spiral cuts or grooves 6. As would be apparent to one of ordinary skill in the art, the width and density of the spiral grooves 6 may be adjusted to provide a desired level of flexibility. In one embodiment, the grooves 6 are formed from very thin spiral cuts or incisions that penetrate through the entire thickness of the cylindrical wall of the rod 4. As known to those skilled in the art, the thickness and material of the tubular walls 5 also affect the level of flexibility.

In one embodiment, the rod 4 is designed to have a flexibility that substantially equals that of a normal back. Flexibility ranges for a normal back are known by those skilled in the art, and one of ordinary skill can easily determine a thickness and material of the tubular walls 5 and a width and density of the grooves 6 to achieve a desired flexibility or flexibility range within the range for a normal back. When referring to the grooves 6 herein, the term "density" refers to tightness of the spiral grooves 6 or, in other words, the distance between adjacent groove lines 6 as shown in FIG. 4, for example. However, it is understood that the present invention is not limited to a particular, predefined flexibility range. In one embodiment, in addition to having desired lateral flexibility characteristics, the rigidity of the rod 4 should be able to endure a vertical axial load applied to the patient's spinal column along a vertical axis of the spine in a uniform manner with respect to the rest of the patient's natural spine.

Figure 5:
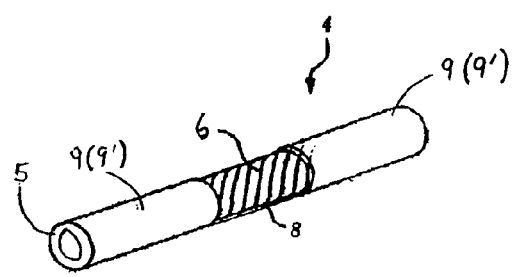
FIG. 5 illustrates a perspective view of a flexible rod connection unit in accordance with another embodiment of the invention.

FIG. 5 illustrates the rod 4 of FIG. 2 wherein only a middle portion 8 is made and designed to be flexible and two end portions 9 are made to be rigid. In one embodiment, metal end rings or caps 9', having no grooves therein, may be placed over respective ends of the rod 4 of FIG. 4 so as make the end portions 9 rigid. The rings or caps 9' may be permanently affixed to the ends of the rod 4 using known methods such as pressing and/or welding the metals together. In another embodiment, the spiral groove 6 is only cut along the length of the middle portion 8 and the end portions 9 comprise the tubular wall 5 without grooves 6. Without the grooves 6, the tubular wall 5, which is made of a rigid metal or metal hybrid material, exhibits high rigidity.

Figure 6:
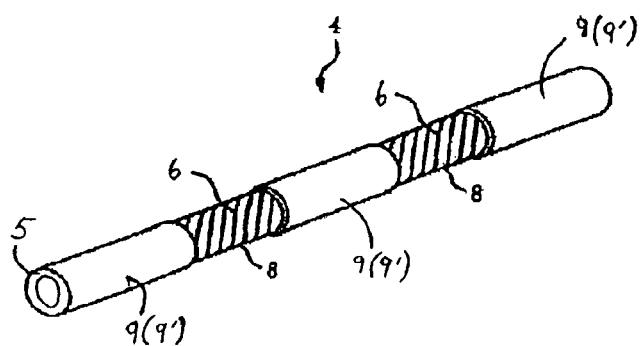
FIG. 6 illustrates a perspective view of a flexible rod connection unit in accordance with a further embodiment of the invention.

FIG. 6 illustrates a further embodiment of the rod 4 having multiple sections, two flexible sections 8 interleaved between three rigid sections 9. This embodiment may be used, for example, to stabilize three adjacent vertebrae with respect to each other, wherein three pedicle screws are fixed to a respective one of the vertebrae and the three rigid sections 9 are connected to a coupling assembly 14 of a respective pedicle screw 2, as described above with respect to FIG. 3. Each of the flexible sections 8 and rigid sections 9 may be made as described above with respect to FIG. 5.

Figure 7:
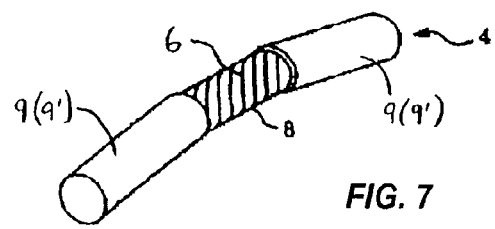
FIG. 7 illustrates a perspective view of a pre-bent flexible rod connection unit in accordance with one embodiment of the invention.

FIG. 7 illustrates another embodiment of the rod 4 having a pre-bent structure and configuration to conform to and maintain a patient's curvature of the spine, known as "lordosis," while stabilizing the spinal column. Generally, a patient's lumbar is in the shape of a 'C' form, and the structure of the rod 4 is formed to coincide to the normal lumbar shape when utilized in the spinal fixation device of FIG. 2, in accordance with one embodiment of the invention. In one embodiment, the pre-bent rod 4 includes a middle portion 8 that is made and designed to be flexible interposed between two rigid end portions 9. The middle portion 8 and end portions 9 may be made as described above with respect to FIG. 5. Methods of manufacturing metallic or metallic-hybrid tubular rods of various sizes, lengths and pre-bent configurations are well-known in the art. Additionally, or alternatively, the pre-bent structure and design of the rod 4 may offset a skew angle when two adjacent pedicle screws are not inserted parallel to one another, as described in further detail below with respect to FIG. 23A.

Figure 8:
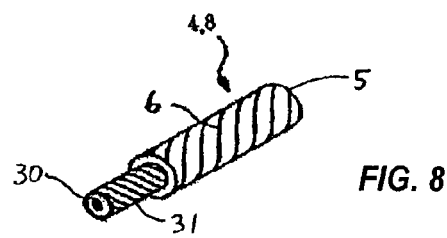
FIG. 8 illustrates a perspective, cross-sectional view of a flexible portion of connection unit in accordance with one embodiment of the invention.

Additional designs and materials used to create a flexible tubular rod 4 or flexible middle portion 8 are described below with respect to FIGS. 8-10. FIG. 8 illustrates a perspective, cross-sectional view of a flexible tubular rod 4, or rod portion 8 in accordance with one embodiment of the invention. In this embodiment, the flexible rod 4, 8 is made from a first metal tube 5 having a spiral groove 6 cut therein as described above with respect to FIGS. 4-7. A second tube 30 having spiral grooves 31 cut therein and having a smaller diameter than the first tube 5 is inserted into the cylindrical cavity of the first tube 5. In one embodiment, the second tube 30 has spiral grooves 31 which are cut in an opposite spiral direction with respect to the spiral grooves 6 cut in the first tube 5, such that the rotational torsion characteristics of the second tube 30 offset at least some of the rotational torsion characteristics of the first tube 5. The second flexible tube 30 is inserted into the core of the first tube to provide further durability and strength to the flexible rod 4, 8. The second tube 30 may be made of the same or different material than the first tube 5. In preferred embodiments, the material used to manufacture the first and second tubes 5 and 30, respectively, may be any one or combination of the following exemplary biocompatible metals: titanium, stainless steel, zirconium, tantalum, cobalt, chromium, nickel, aluminum, vanadium, and alloys thereof. In alternative embodiments, the tubes 5 and 30 may be made from a biocompatible metal-synthetic hybrid material or entirely from a biocompatible synthetic material. Examples of biocompatible synthetic materials are: polymers, elastomers, resins, plastics, carbon graphite and composites thereof. Such materials are well known in the art.

Figure 9:
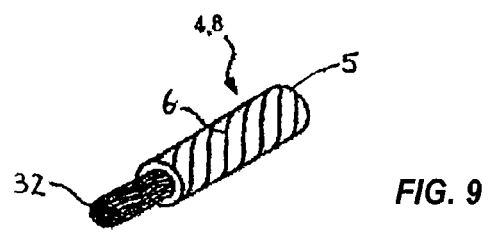
FIG. 9 illustrates a perspective, cross-sectional view of a flexible portion of connection unit in accordance with another embodiment of the invention.

FIG. 9 illustrates a perspective, cross-sectional view of a flexible rod 4, 8 in accordance with a further embodiment of the invention. In one embodiment, the flexible rod 4, 8 includes an inner core made of a biocompatible metallic wire 32 comprising a plurality of overlapping thin metallic yarns, such as steel yarns, titanium yarns, or titanium-alloy yarns. The wire 32 is encased by a metal, or metal hybrid, flexible tube 5 having spiral grooves 6 cut therein, as discussed above. The number and thickness of the metallic yarns in the wire 32 also affects the rigidity and flexibility of the rod 4, 8. By changing the number, thickness or material of the yarns flexibility can be increased or decreased. Thus, the number, thickness and/or material of the metallic yarns in the wire 32 can be adjusted to provide a desired rigidity and flexibility in accordance with a patient's particular needs. Those of ordinary skill in the art can easily determine the number, thickness and material of the yarns, in conjunction with a given flexibility of the tube 5 in order to achieve a desired rigidity v. flexibility profile for the rod 4, 8. In alternative embodiments, the wire 32 and plurality of yarns may be made from a biocompatible metal-synthetic hybrid material or entirely from biocompatible synthetic materials, as discussed above.

Figure 10:
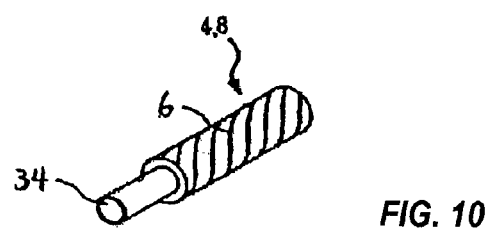
FIG. 10 illustrates a perspective, cross-sectional view of a flexible portion of connection unit in accordance with a further embodiment of the invention.

FIG. 10 shows yet another embodiment of a flexible rod 4 wherein the flexible tube 5 encases a non-metallic, flexible core 34. In various embodiments, the core 34 may be made from, for example, known biocompatible metals, biocompatible shape memory alloys (e.g., NITINOL), or biocompatible synthetic materials such as carbon fiber, Poly Ether Ether Ketone (PEEK), Poly Ether Ketone Ketone Ether Ketone (PEKKEK), or Ultra High Molecular Weight Poly Ethylene (UHMWPE).

Figure 11:
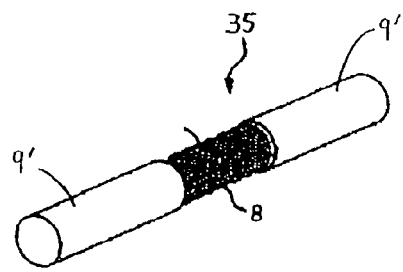
FIG. 11 illustrates a perspective view of a flexible rod connection unit in accordance with one embodiment of the invention.

FIG. 11 illustrates a perspective view of another embodiment of the flexible rod 35 in which a plurality of wires 32, as described above with respect to FIG. 9, are interweaved or braided together to form a braided wire rod 35. The braided wire rod 35 can be made from the same materials as the wire 32 discussed above. In addition to the variability of the rigidity and flexibility of the wire 32 as explained above, the rigidity and flexibility of the braided rod 35 can be further modified to achieve desired characteristics by varying the number and thickness of the wires 32 used in the braided structure 35. For example, in order to achieve various flexion levels or ranges within the known flexion range of a normal healthy spine, those of ordinary skill in the art can easily manufacture various designs of the braided wire rod 35 by varying and measuring the flexion provided by different gauges, numbers and materials of the wire used to create the braided wire rod 35. In a further embodiment each end of the braided wire rod 35 is encased by a rigid cap or ring 9' as described above with respect to FIGS. 5-7, to provide a rod 4 having a flexible middle portion 8 and rigid end portions 9. In a further embodiment (not shown), the braided wire rod 35 may be utilized as a flexible inner core encased by a tube 5 having spiral grooves 6 cut therein to create a flexible rod 4 or rod portion 8, in a similar fashion to the embodiments shown in FIGS. 8-10. As used herein the term "braid" or "braided structure" encompasses two or more wires, strips, strands, ribbons and/or other shapes of material interwoven in an overlapping fashion. Various methods of interweaving wires, strips, strands, ribbons and/or other shapes of material are known in the art. Such interweaving techniques are encompassed by the present invention. In another exemplary embodiment (not shown), the flexible rod 35 includes a braided structure having two or more strips, strands or ribbons interweaved in a diagonally overlapping pattern.

Figure 12A:
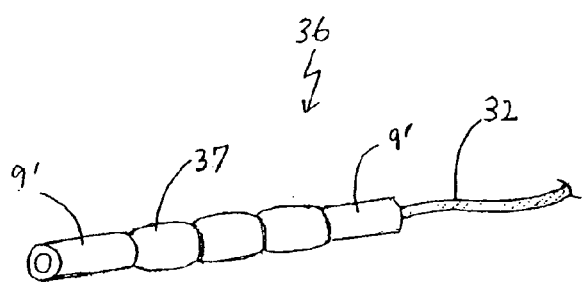
FIG. 12A illustrates a perspective view of a flexible connection unit having one or more spacers in between two end portions, in accordance with one embodiment of the invention.
Figure 12B:
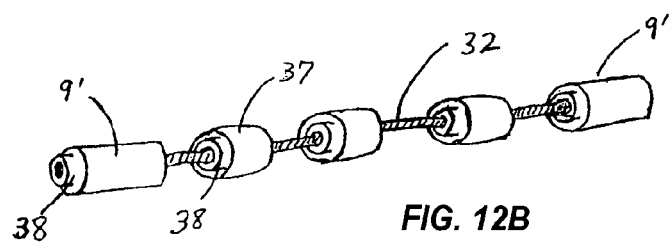
FIG. 12B illustrates an exploded view of the flexible connection unit of FIG. 12A.
Figure 12C:
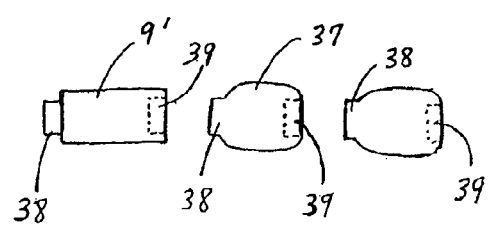
FIG. 12C provides a view of the male and female interlocking elements of the flexible connection unit of FIGS. 12A and 12B, in accordance with one embodiment of the invention.

FIG. 12A illustrates a further embodiment of a flexible connection unit 36 having two rigid end portions 9' and an exemplary number of spacers 37 interposed between the end portions. In one embodiment, the rigid end portions 9' and spacers can be made of bio-compatible metal, metal-hybrid, and/or synthetic materials as discussed above. The connection unit 36 further includes a flexible member or wire 32, as discussed above with respect to FIG. 9, which traverses an axial cavity or hole (not shown) in each of the rigid end portions 9' and spacers 37. FIG. 12B illustrates an exploded view of the connection unit 36 that further shows how the wire 32 is inserted through longitudinal axis holes of the rigid end portions 9' and spacers 37. As further shown in FIG. 12B, each of the end portions 9' and spacers 37 include a male interlocking member 38 which is configured to mate with a female interlocking cavity (not shown) in the immediately adjacent end portion 9' or spacer 37. FIG. 12 C illustrates an exploded side view and indicates with dashed lines the location and configuration of the female interlocking cavity 39 for receiving corresponding male interlocking members 38.

Figure 13:
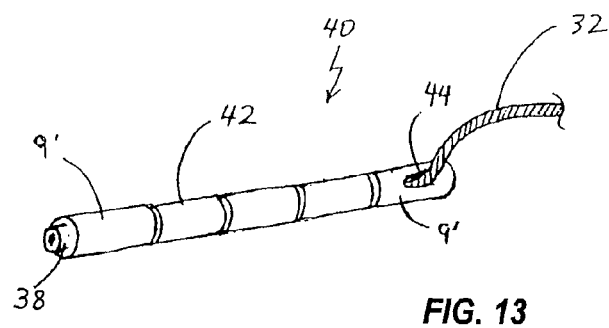
FIG. 13 shows a perspective view of a flexible connection unit, in accordance with a further embodiment of the invention.

FIG. 13 shows a perspective view of a flexible connection unit 40 in accordance with another embodiment of the invention. The connection unit 40 is similar to the connection unit 36 described above, however, the spacers 42 are configured to have the same shape and design as the rigid end portions 9'. Additionally, the end portions 9' have an exit hole or groove 44 located on a lateral side surface through which the wire 32 may exit, be pulled taut, and clamped or secured using a metal clip (not shown) or other known techniques. In this way, the length of the flexible connection unit 36 or 40 may be varied at the time of surgery to fit each patient's unique anatomical characteristics. In one embodiment, the wire 32 may be secured using a metallic clip or stopper (not shown). For example, a clip or stopper may include a small tubular cylinder having an inner diameter that is slightly larger than the diameter of the wire 32 to allow the wire 32 to pass therethrough. After the wire 32 is pulled to a desired tension through the tubular stopper, the stopper is compressed so as to pinch the wire 32 contained therein. Alternatively, the wire 32 may be pre-secured using known techniques during the manufacture of the connection units 36, 40 having a predetermined number of spacers 37, 42 therein.

Figure 14:
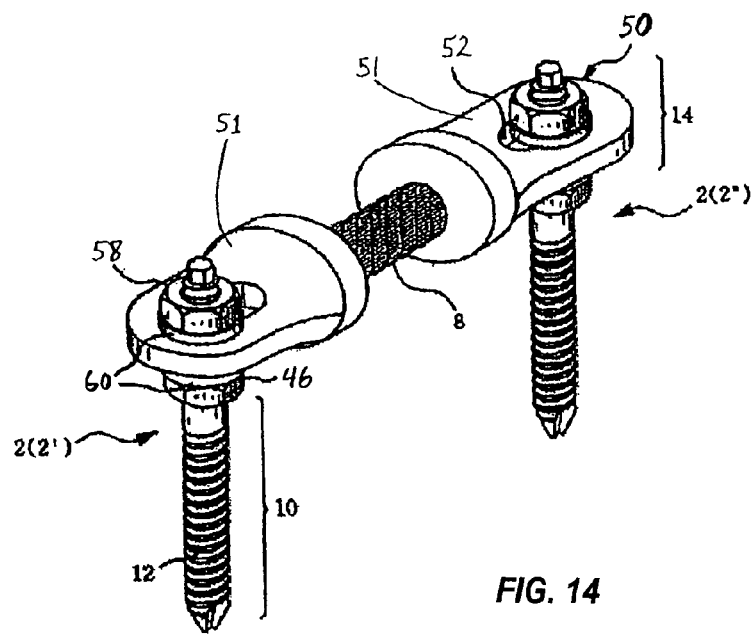
FIG. 14 illustrates a perspective view of a spinal fixation device in accordance with another embodiment of the invention.

FIG. 14 depicts a spinal fixation device according to another embodiment of the present invention. The spinal fixation device includes: at least two securing members 2 containing an elongate screw type shaft 10 having an external spiral thread 12, and a coupling assembly 14. The device further includes a plate connection unit 50, or simply "plate 50," configured to be securely connected to the coupling parts 14 of the two securing members 2. The plate 50 comprises two rigid connection members 51 each having a planar surface and joined to each other by a flexible middle portion 8. The flexible middle portion 8 may be made in accordance with any of the embodiments described above with respect to FIGS. 4-11. Each connection member 51 contains a coupling hole 52 configured to receive therethrough a second threaded shaft 54 (FIG. 15) of the coupling assembly 14.

Figure 15:
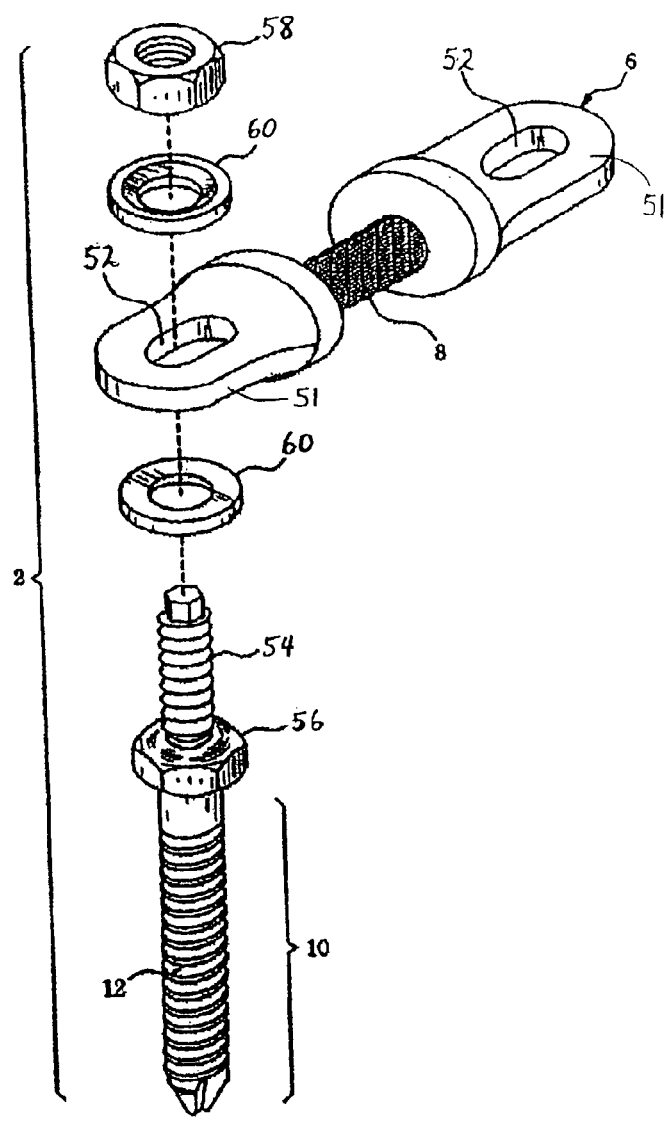
FIG. 15 illustrates an exploded view of the spinal fixation device of FIG. 14.

As shown in FIG. 15, the coupling assembly 14 of the securing member 2 includes a bolt head 56 adjoining the top of the first threaded shaft 10 and having a circumference or diameter greater than the circumference of the first threaded shaft 10. The second threaded shaft 54 extends upwardly from the bolt head 56. The coupling assembly 14 further includes a nut 58 having an internal screw thread configured to mate with the second threaded shaft 54, and one or more washers 60, for clamping the connection member 51 against the top surface of the bolt head 56, thereby securely attaching the plate 50 to the pedicle screw 2.

Figure 16A:
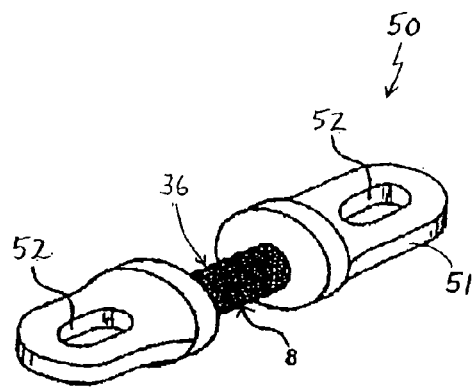
FIG. 16A shows a perspective view of a flexible plate connection unit in accordance with one embodiment of the invention.
Figure 16B:
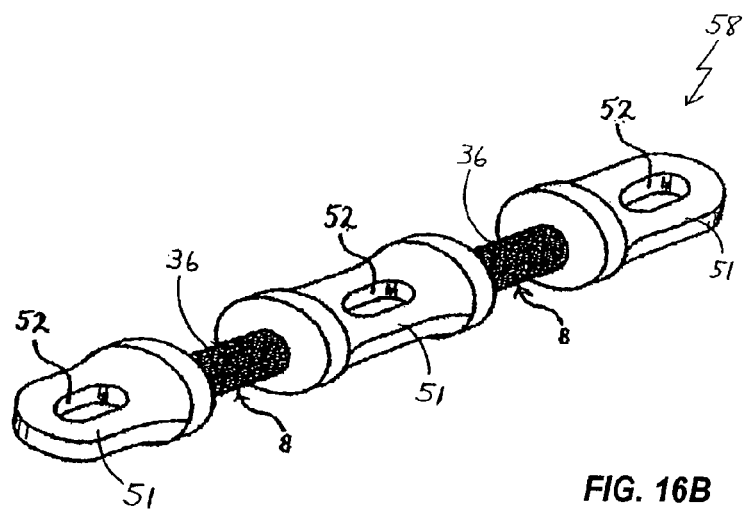
FIG. 16B illustrates a perspective view of a flexible plate connection unit in accordance with a further embodiment of the invention.
Figure 16C:
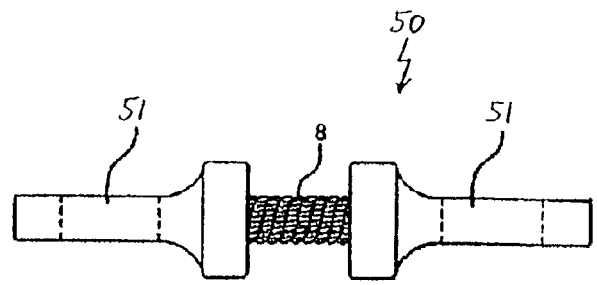
FIG. 16C shows a side view of the flexible plate connection unit of FIG. 16A.
Figure 16D:
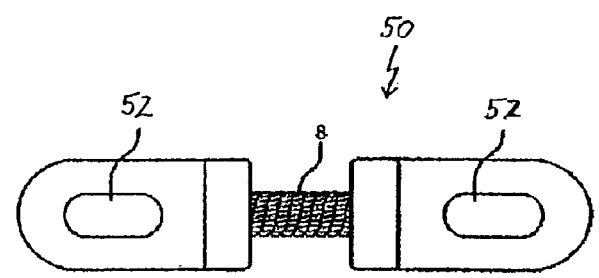
FIG. 16D shows a top view of the flexible plate connection unit of FIG. 16A.

FIGS. 16A and 16B illustrate two embodiments of a plate connection unit 40 having at least two coupling members 51 and at least one flexible portion 8 interposed between and attached to two adjacent connection members 51. As shown in FIGS. 16A and 16B, the flexible middle portion 8 comprises a flexible braided wire structure 36 as described above with respect to FIG. 11. However, the flexible portion 8 can be designed and manufactured in accordance with any of the embodiments described above with respect to FIGS. 4-11, or combinations thereof. FIGS. 16C and 16D illustrate a side view and top view, respectively, of the plate 50 of FIG. 16A. The manufacture of different embodiments of the flexible connection units 50 and 58 having different types of flexible middle portions 8, as described above, is easily accomplished using known metallurgical, organic polymer, natural resin, or composite materials, and compatible manufacturing and machining processes.

Figure 16E:
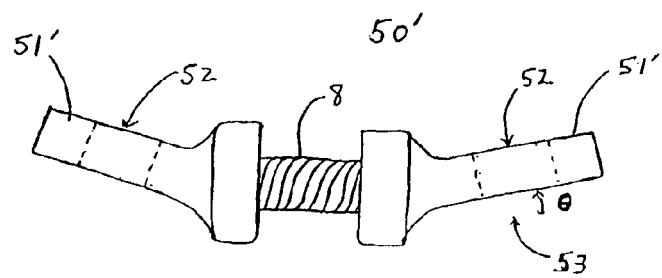
FIG. 16E illustrates a side view of the flexible plate connection unit of FIG. 16A having a pre-bent configuration in accordance with a further embodiment of the invention.

FIG. 16E illustrate a side view of a pre-bent plate connection unit 50', in accordance with a further embodiment of the invention. This plate connection unit 50' is similar to the plate 50 except that connection members 51' are formed or bent at an angle θ from a parallel plane 53 during manufacture of the plate connection unit 50'. As discussed above with respect to the pre-bent rod-like connection unit 4 of FIG. 7, this pre-bent configuration is designed to emulate and support a natural curvature of the spine (e.g., lordosis). Additionally, or alternatively, this pre-bent structure may offset a skew angle when two adjacent pedicle screws are not inserted parallel to one another, as described in further detail below with respect to FIG. 23A.

Figure 17:
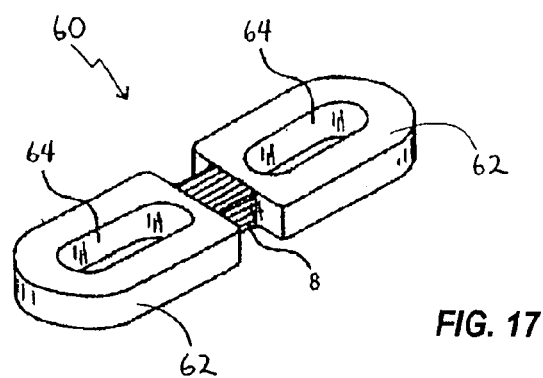
FIG. 17 is a perspective view of a flexible plate connection unit in accordance with another embodiment of the invention.

FIG. 17 illustrates a perspective view of a plate connection unit 60 having two planar connection members 62 each having a coupling hole 64 therein for receiving the second threaded shaft 44 of the pedicle screw 2. A flexible middle portion 8 is interposed between the two connection members 62 and attached thereto. In one embodiment, the flexible middle portion 8 is made in a similar fashion to wire 32 described above with respect to FIG. 9, except it has a rectangular configuration instead of a cylindrical or circular configuration as shown in FIG. 9. It is understood, however, that the flexible middle portion 8 may be made in accordance with the design and materials of any of the embodiments previously discussed.

Figure 18:
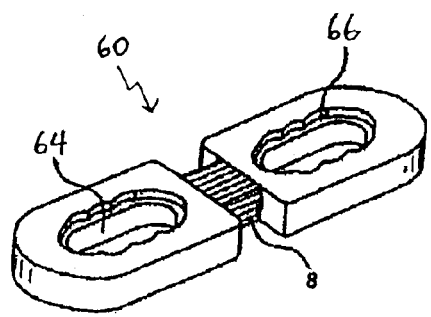
FIG. 18 illustrates a perspective view of a flexible plate connection unit in accordance with another embodiment of the invention.

FIG. 18 illustrates a perspective view of a further embodiment of the plate 60 of FIG. 17 wherein the coupling hole 64 includes one or more nut guide grooves 66 cut into the top portion of the connection member 62 to seat and fix the nut 58 (FIG. 15) into the coupling hole 64. The nut guide groove 66 is configured to receive and hold at least a portion of the nut 58 therein and prevent lateral sliding of the nut 58 within the coupling hole 64 after the connection member 62 has been clamped to the bolt head 56 of the pedicle screw 2.

Figure 19:
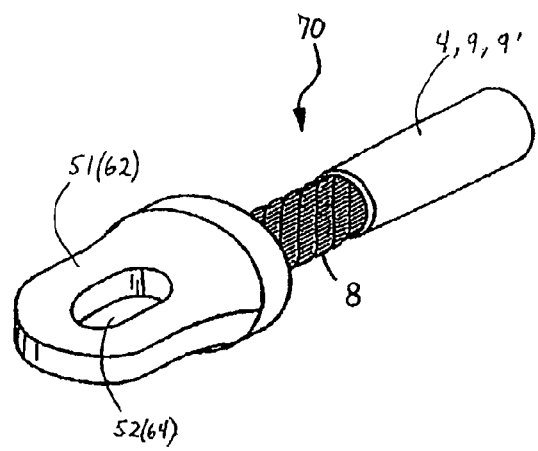
FIG. 19 illustrates a perspective view of a hybrid rod-plate connection unit having a flexible middle portion according to a further embodiment of the present invention.

FIG. 19 illustrates a perspective view of a hybrid plate and rod connection unit 70 having a rigid rod-like connection member 4, 9 or 9', as described above with respect to FIGS. 4-7, at one end of the connection unit 70 and a plate-like connection member 51 or 62, as described above with respect to FIGS. 14-18, at the other end of the connection unit 70. In one embodiment, interposed between rod-like connection member 9 (9') and the plate-like connection member 52 (64) is a flexible member 8. The flexible member 8 may be designed and manufactured in accordance with any of the embodiments discussed above with reference to FIGS. 8-13.

Figure 20:
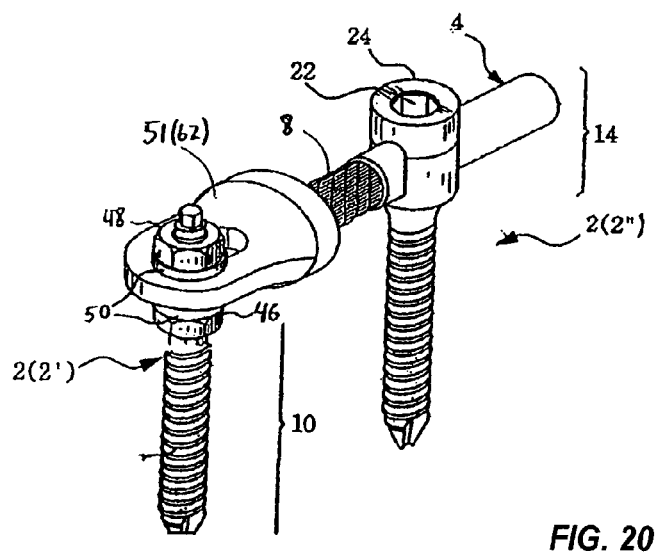
FIG. 20 is a perspective view of a spinal fixation device that utilizes the hybrid rod-plate connection unit of FIG. 19.

FIG. 20 illustrates a perspective view of a spinal fixation device that utilizes the hybrid plate and rod connection unit 70 of FIG. 19. As shown in FIG. 20, this fixation device utilizes two types of securing members 2 (e.g., pedicle screws), the first securing member 2' being configured to securely hold the plate connection member 42(64) as described above with respect to FIG. 15, and the second securing member 2" being configured to securely hold the rod connection member 4, 9 or 9', as described above with respect to FIG. 3.

Figure 21:
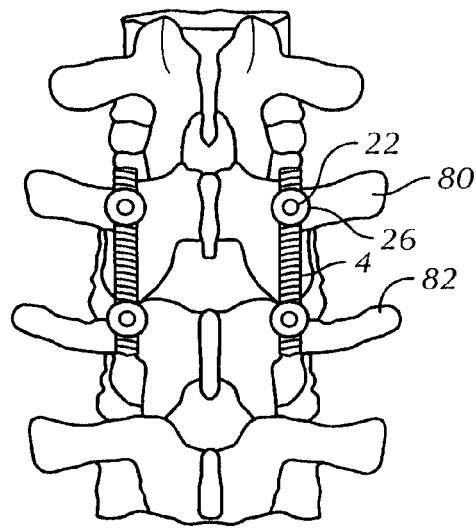
FIG. 21 illustrates a perspective view of the spinal fixation device of FIG. 1 after it has been implanted into a patient's spinal column.
Figure 22A:
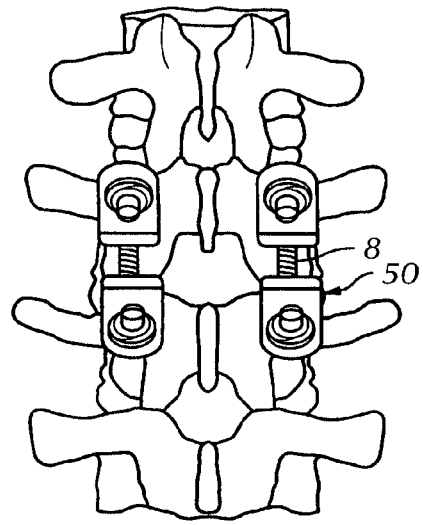
FIGS. 22A and 22B provide perspective views of spinal fixation devices utilizing the plate connection units of FIGS. 16A and 16B, respectively.
Figure 22B:
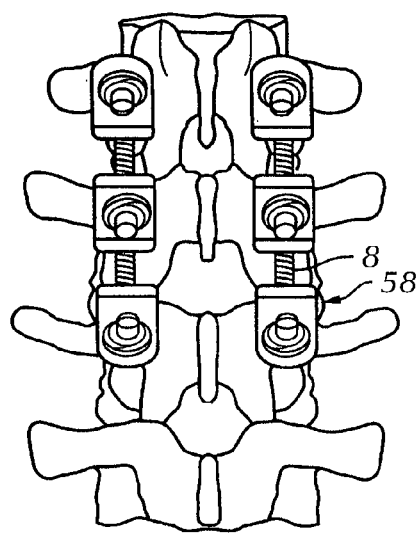

FIG. 21 illustrates a perspective top view of two spinal fixation devices, in accordance with the embodiment illustrated in FIG. 1, after they are attached to two adjacent vertebrae 80 and 82 to flexibly stabilize the vertebrae. FIGS. 22A and 22B illustrate perspective top views of spinal fixation devices using the flexible stabilizing members 50 and 58 of FIGS. 16A and 16B, respectively, after they are attached to two or more adjacent vertebrae of the spine.

FIG. 23A illustrates a side view of a spinal fixation device after it has been implanted into the pedicles of two adjacent vertebrae. As shown in this figure, the pedicle screws 2 are mounted into the pedicle bone such that a center axis 80 of the screws 2 are offset by an angle θ from a parallel plane 82 and the center axes 80 of the two screws 2 are offset by an angle of approximately 2θ from each other. This type of non-parallel insertion of the pedicle screws 2 often results due to the limited amount of space that is available when performing minimally invasive surgery. Additionally, the pedicle screws 2 may have a tendency to be skewed from parallel due to a patient's natural curvature of the spine (e.g., lordosis). Thus, due to the non-parallel nature of how the pedicle screws 2 are ultimately fixed to the spinal pedicle, it is desirable to offset this skew when attaching a rod or plate connection unit to each of the pedicle screws 2.

FIG. 23B illustrates a side view of the head of the pedicle screw in accordance with one embodiment of the invention. The screw 2 includes a cylindrical head 84 which is similar to the cylindrical head 16 described above with respect to FIG. 3 except that the cylindrical head 84 includes a slanted seat 86 configured to receive and hold a flexible rod 4 in a slanted orientation that offsets the slant or skew θ of the pedicle screw 2 as described above. The improved pedicle screw 2 further includes a slanted stabilizing spacer 88 which is configured to securely fit inside the cavity of the cylindrical head 84 and hold down the rod 4 at the same slant as the slanted seat 86. The pedicle screw 2 further includes an outside threaded nut 22 configured to mate with spiral threads along the interior surface (not shown) of the cylindrical head 84 for clamping down and securing the slanted spacer 88 and the rod 4 to the slanted seat 86 and, hence, to the cylindrical head 84 of the pedicle screw 2.

Figure 23D:
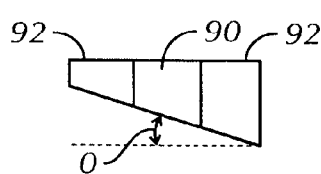
FIG. 23D illustrates a side view of the slanted stabilizing spacer of FIG. 23C.
Figure 23E:
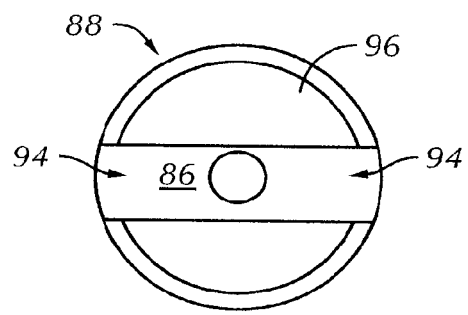
FIG. 23E is a top view of the cylindrical head of the pedicle screw of FIG. 23.

FIG. 23C shows a perspective view of the slanted spacer 88, in accordance with one embodiment of the invention. The spacer 88 includes a circular middle portion 90 and two rectangular-shaped end portions 92 extending outwardly from opposite sides of the circular middle portion 90. FIG. 23D shows a side view of the spacer 88 that further illustrates the slant from one end to another to compensate or offset the skew angle θ of the pedicle screw 2. FIG. 23E illustrates a top view of the cylindrical head 84 configured to receive a rod 4 and slanted spacer 88 therein. The rod 4 is received through two openings or slots 94 in the cylindrical walls of the cylindrical head 84, which allow the rod 4 to enter the circular or cylindrical cavity 96 of the cylindrical head 84 and rest on top of the slanted seat 86 formed within the circular or cylindrical cavity 94. After the rod 4 is positioned on the slanted seat 86, the slanted stabilizing spacer 88 is received in the cavity 96 such that the two rectangular-shaped end portions 92 are received within the two slots 94, thereby preventing lateral rotation of the spacer 88 within the cylindrical cavity 96. Finally, the outside threaded nut 22 and fixing cap 26 are inserted on top of the slanted spacer 88 to securely hold the spacer 88 and rod 4 within the cylindrical head 84.

Figure 24:
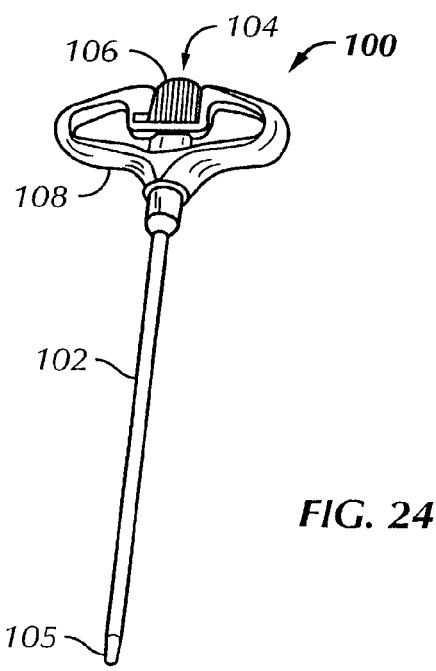
FIG. 24 illustrates a perspective view of a marking and guiding device in accordance with one embodiment of the invention.

FIG. 24 illustrates a perspective view of a marking and guidance device 100 for marking a desired location on the spinal pedicle where a pedicle screw 2 will be inserted and guiding the pedicle screw 2 to the marked location using a minimally invasive surgical technique. As shown in FIG. 24, the marking device 100 includes a tubular hollow guider 52 which receives within its hollow an inner trocar 104 having a sharp tip 105 at one end that penetrates a patient's muscle and tissue to reach the spinal pedicle. the inner trocar 104 further includes a trocar grip 106 at the other end for easy insertion and removal of the trocar 104. In one embodiment, the marking and guidance device 100 includes a guider handle 108 to allow for easier handling of the device 100.

Figure 25:
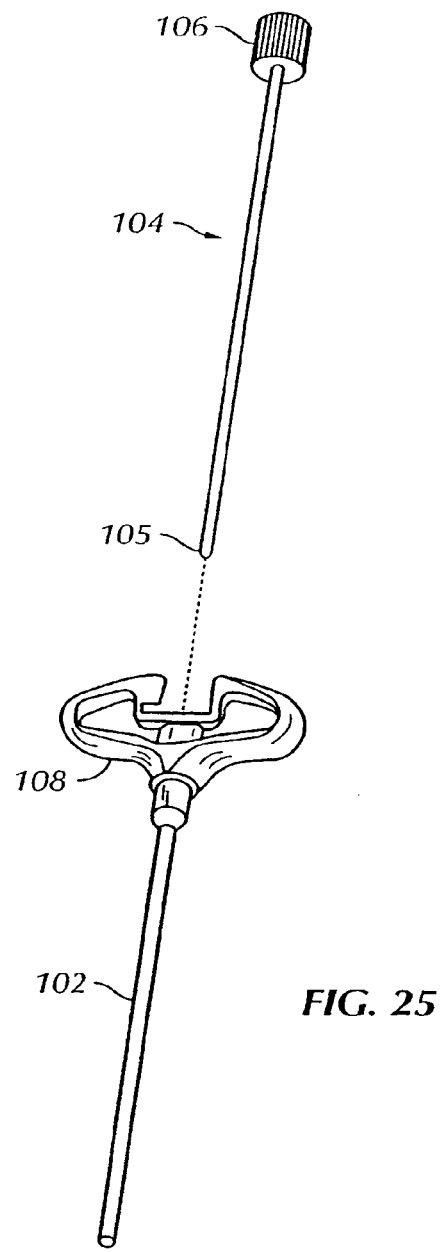
FIG. 25 is an exploded view of the marking and guidance device of FIG. 24.

As shown in FIG. 25, the trocar 104 is in the form of a long tube or cylinder having a diameter smaller than the inner diameter of the hollow of the guider 102 so as to be inserted into the hollow of the tubular guider 102. The trocar 104 further includes a sharp or pointed tip 105 for penetrating the vertebral body through the pedicle. The trocar 104 further includes a trocar grip 106 having a diameter larger than the diameter of the hollow of the guider tube 102 in order to stop the trocar 104 from sliding completely through the hollow. The trocar grip 106 also allows for easier handling of the trocar 104.

Figure 26A:
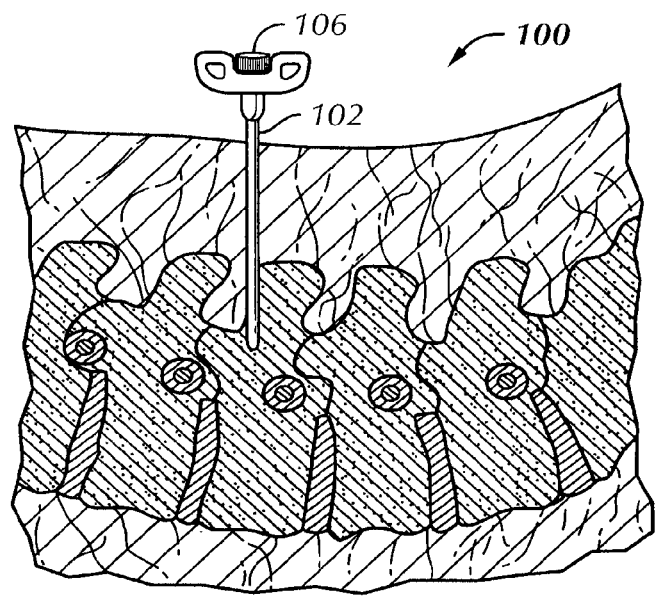
FIG. 26A provides a perspective, cross-section view of a patient's spine after the marking and guiding device of FIG. 24 has been inserted during surgery.
Figure 26B:
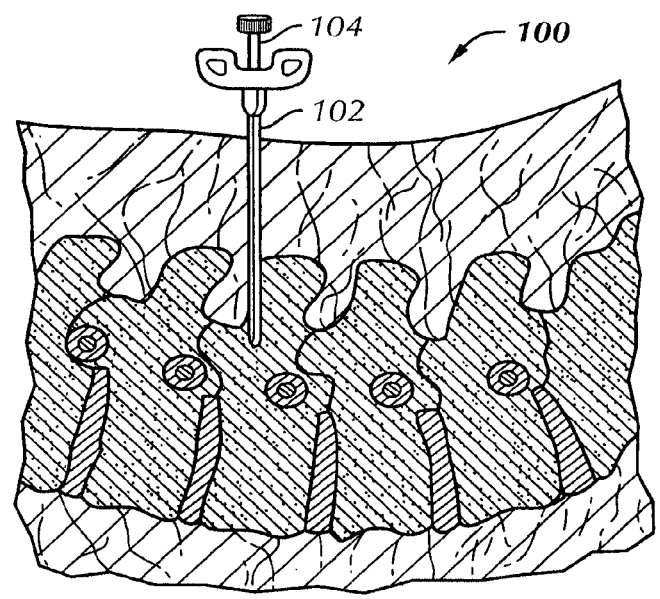
FIG. 26B provides a perspective, cross-section view of a patient's spine as an inner trocar of the marking and guiding device of FIG. 24 is being removed.

FIGS. 26A and 26B provide perspective views of the marking and guidance device 100 after it has been inserted into a patient's back and pushed through the muscle and soft tissue to reach a desired location on the spinal pedicle. The desired location is determined using known techniques such as x-ray or radiographic imaging for a relatively short duration of time. After the marking and guidance device 100 has been inserted, prolonged exposure of the patient to x-ray radiation is unnecessary. As shown in FIG. 26B, after the guidance tube 102 is positioned over the desired location on the pedicle, the inner trocar 104 is removed to allow fiducial pins (not shown) to be inserted into the hollow of the guidance tube 102 and thereafter be fixed into the pedicle.

Figure 27A:
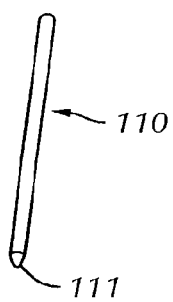
FIGS. 27A and 27B illustrate perspective views of two embodiments of a fiducial pin, respectively.
Figure 27B:
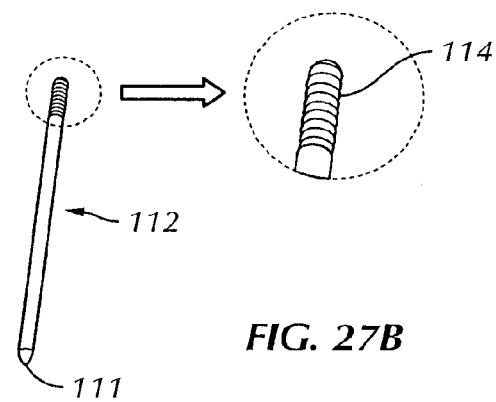

FIGS. 27A and 27B illustrate perspective views of two embodiments of the fiducial pins 110 and 112, respectively. As mentioned above, the fiducial pins 110 and 112 according to the present invention are inserted and fixed into the spinal pedicle after passing through the hollow guider 102. The pins 110 and 112 have a cylindrical shape with a diameter smaller than the inner diameter of the hollow of the guider tube 102 in order to pass through the hollow of the guider 102. An end of each fiducial pin is a sharp point 111 configured to be easily inserted and fixed into the spinal pedicle of the spinal column. In one embodiment, as shown in FIG. 27B, the other end of the fiducial pin incorporates a threaded shaft 114 which is configured to mate with an internally threaded tube of a retriever (not shown) for extraction of the pin 112. This retriever is described in further detail below with respect to FIG. 32.

The fiducial pins 110, 112 are preferably made of a durable and rigid biocompatible metal (e.g., stainless steel, iron steel, titanium, titanium alloy) for easy insertion into the pedicle bone. In contrast to prior art guide wires, because of its comparatively shorter length and more rigid construction, the fiducial pins 110, 112 are easily driven into the spinal pedicle without risk of bending or structural failure. As explained above, the process of driving in prior art guidance wires was often very difficult and time-consuming. The insertion of the fiducial pins 110, 112 into the entry point on the spinal pedicle is much easier and convenient for the surgeon and, furthermore, does not hinder subsequent procedures due to a guide wire protruding out of the patient's back.

Figure 28:
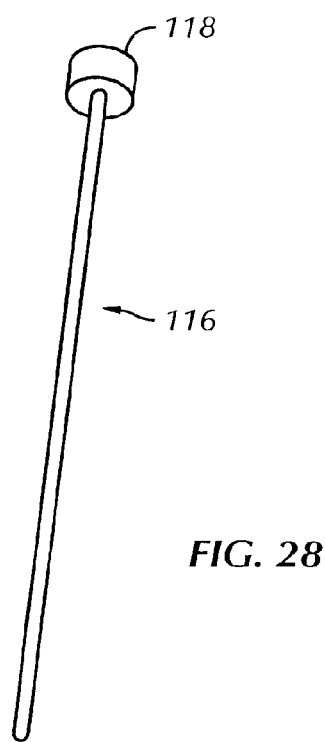
FIG. 28 is a perspective view of a pushing trocar in accordance with a further embodiment of the invention.

FIG. 28 shows a cylindrical pushing trocar 116 having a cylindrical head 118 of larger diameter than the body of the pushing trocar 116. The pushing trocar 116, according to the present invention, is inserted into the hollow of the guider 102 after the fiducial pin 110 or 112 has been inserted into the hollow of the guider 102 to drive and fix the fiducial pin 110 or 112 into the spinal pedicle. During this pin insertion procedure, a doctor strikes the trocar head 118 with a chisel or a hammer to drive the fiducial pin 110 and 112 into the spinal pedicle. In preferred embodiments, the pushing trocar 116 is in the form of a cylindrical tube, which has a diameter smaller than the inner diameter of the hollow of the guider tube 112. The pushing trocar 116 also includes a cylindrical head 118 having a diameter larger than the diameter of the pushing trocar 116 to allow the doctor to strike it with a chisel or hammer with greater ease. Of course, in alternative embodiments, a hammer or chisel is not necessarily required. For example, depending on the circumstances of each case, a surgeon may choose to push or tap the head 118 of the pushing trocar 116 with the palm of his or her hand or other object.

Figure 29A:
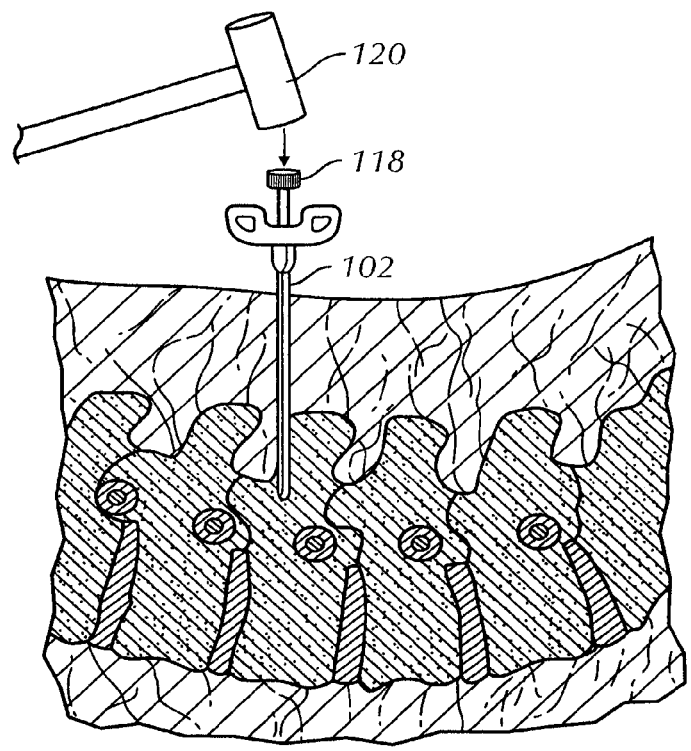
FIG. 29A illustrates a perspective, cross-sectional view of a patient's spine as the pushing trocar of FIG. 28 is used to drive a fiducial pin into a designate location of a spinal pedicle, in accordance with one embodiment of the invention.
Figure 29B:
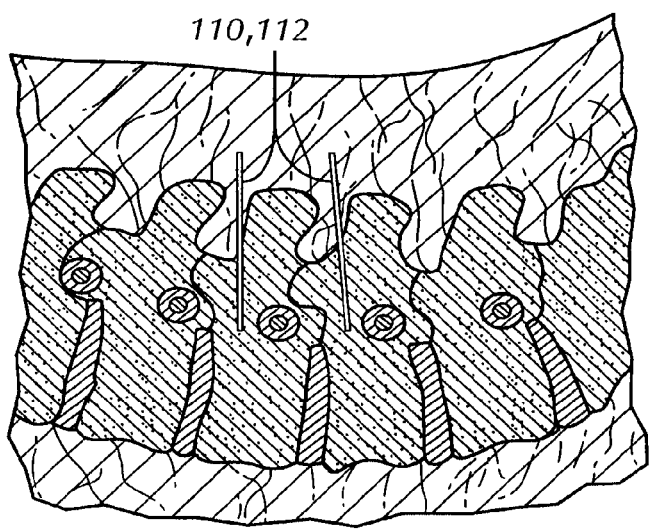
FIG. 29B illustrates a perspective, cross-sectional view of a patient's spine after two fiducial pins have been implanted into two adjacent spinal pedicles, in accordance with one embodiment of the invention.

FIG. 29A illustrates how a hammer or mallet 120 and the pushing trocar 116 may be used to drive the pin 110, 112 through the hollow of the guider tube 102 and into the designated location of the spinal pedicle. FIG. 29B illustrates a perspective cross-sectional view of the spinal column after two fiducial pins 110, 112 have been driven and fixed into two adjacent vertebrae.

Figure 30:
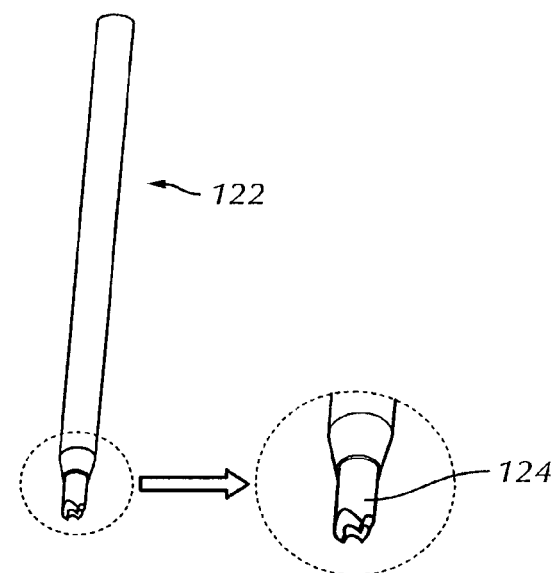
FIG. 30 is a perspective view of a cannulated awl in accordance with one embodiment of the invention.
Figure 31:
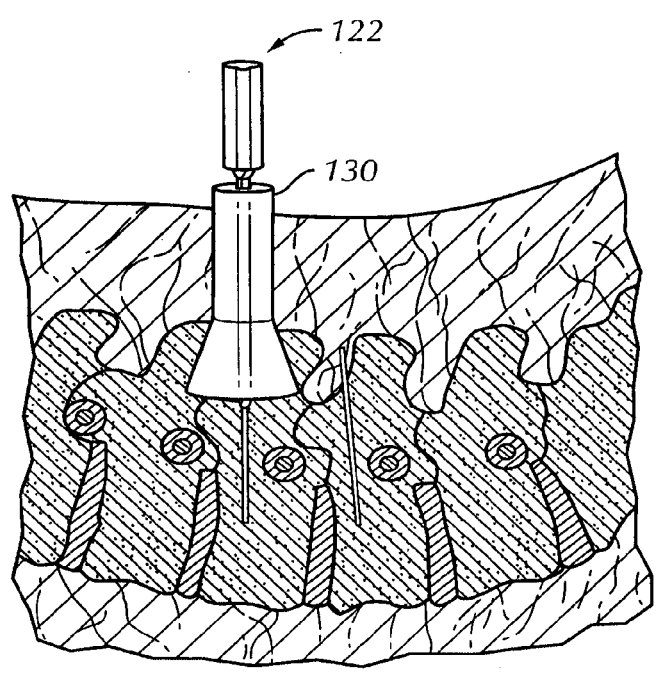
FIG. 31 is a perspective, cross-sectional view of a patient's spine as the cannulated awl of FIG. 30 is being used to enlarge an entry hole for a pedicle screw, in accordance with one embodiment of the invention.

After the fiducial pins 110 or 112 have been inserted into the spinal pedicle as discussed above, in one embodiment, a larger hole or area centered around each pin 110, 112 is created to allow easer insertion and mounting of a pedicle screw 2 into the pedicle bone. The larger hole is created using a cannulated awl 122 as shown in FIG. 30. The cannulated awl 122 is inserted over the fiducial pin 110, 112 fixed at the desired position of the spinal pedicle. The awl 122 is in the form of a cylindrical hollow tube wherein an internal diameter of the hollow is larger than the outer diameter of the fiducial pins 110 and 112 so that the pins 110, 112 may be inserted into the hollow of the awl 122. The awl 122 further includes one or more sharp teeth 124 at a first end portion for cutting and grinding tissue and bone so as to create the larger entry point centered around the fiducial pin 110, 112 so that the pedicle screw 2 may be more easily implanted into the spinal pedicle. FIG. 31 illustrates a perspective cross-sectional view of a patient's spinal column when the cannulated awl 122 is inserted into a minimally invasive incision in the patient's back, over a fiducial pin 110, 112 to create a larger insertion hole for a pedicle screw 2 (not shown). As shown in FIG. 31, a retractor 130 has been inserted into the minimally invasive incision over the surgical area and a lower tubular body of the retractor 130 is expanded to outwardly push surrounding tissue away from the surgical area and provide more space and a visual field for the surgeon to operate. In order to insert the retractor 130, in one embodiment, the minimally invasive incision is made in the patient's back between and connecting the two entry points of the guide tube 102 used to insert the two fiducial pins 110, 112. Before the retractor 130 is inserted, prior expansion of the minimally invasive incision is typically required using a series of step dilators (not shown), each subsequent dilator having a larger diameter than the previous dilator. After the last step dilator is in place, the retractor 130 is inserted with its lower tubular body in a retracted, non-expanded state. After the retractor 130 is pushed toward the spinal pedicle to a desired depth, the lower tubular portion is then expanded as shown in FIG. 31. The use of step dilators and retractors are well known in the art.

Figure 32:
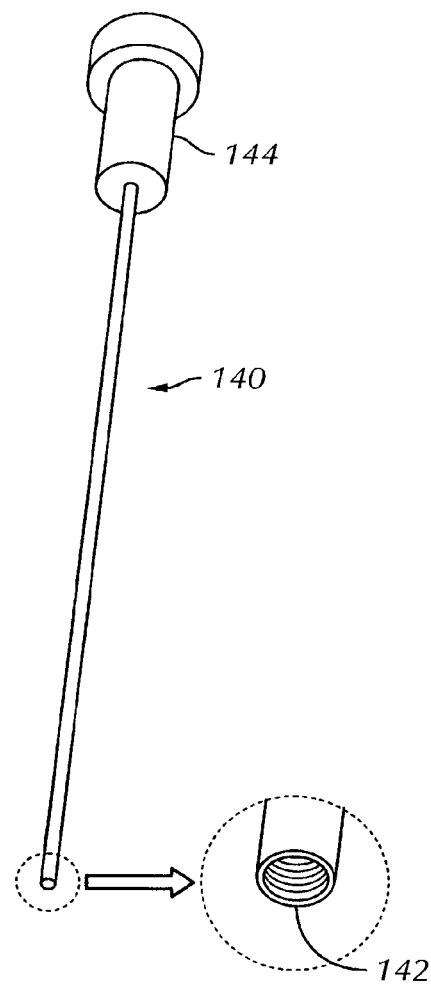
FIG. 32 provides a perspective view of fiducial pin retrieving device, in accordance with one embodiment of the invention.

After the cannulated awl 122 has created a larger insertion hole for the pedicle screw 2, in one embodiment, the fiducial pin 110, 112 is removed. As discussed above, if the fiducial pin 112 has been used, a retrieving device 140 may be used to remove the fiducial pin 112 before implantation of a pedicle screw 2. As shown in FIG. 32, the retriever 140 comprises a long tubular or cylindrical portion having an internally threaded end 142 configured to mate with the externally threaded top portion 114 of the fiducial pin 112. After the retriever end 142 has been screwed onto the threaded end 114, a doctor my pull the fiducial pin 112 out of the spinal pedicle. In another embodiment, if the fiducial pin 110 without a threaded top portion has been used, appropriate tools (e.g., specially designed needle nose pliers) may be used to pull the pin 110 out.

Figure 33:
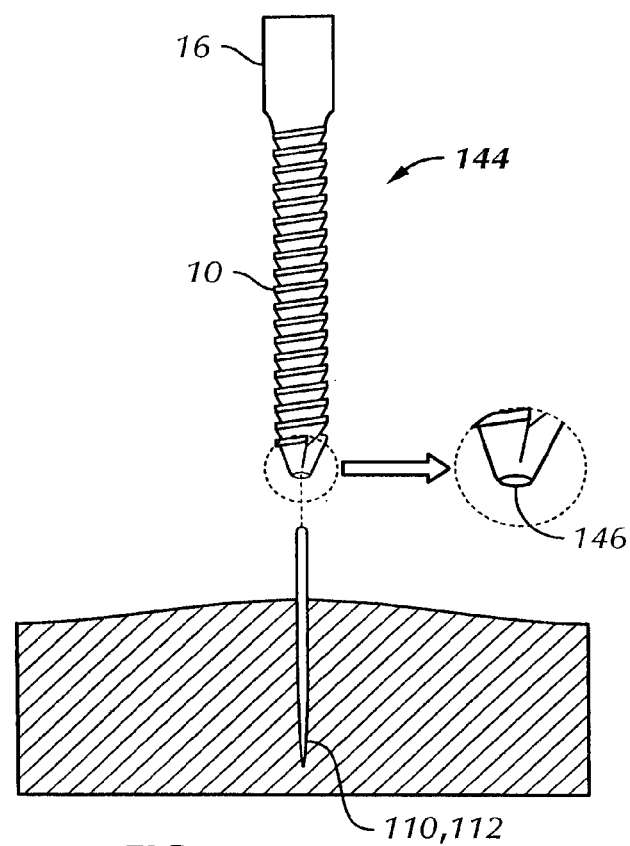
FIG. 33 is a perspective view of a pedicle screw having an axial cylindrical cavity for receiving at least a portion of a fiducial pin therein, in accordance with a further embodiment of the invention.

In alternate embodiments, the fiducial pins 110, 112 are not extracted from the spinal pedicle. Instead, a specially designed pedicle screw 144 may be inserted into the spinal pedicle over the pin 110, 112 without prior removal of the pin 110, 112. As shown in FIG. 33, the specially designed pedicle screw 144 includes an externally threaded shaft 10 and a coupling assembly 14 (FIG. 3) that includes a cylindrical head 16 (FIG. 3) for receiving a flexible rod-shaped connection unit 4 (FIGS. 4-13). Alternatively, the coupling assembly 14 may be configured to receive a plate-like connection unit as shown in FIGS. 14-20. The pedicle screw 144 further includes a longitudinal axial channel (not shown) inside the threaded shaft 10 having an opening 146 at the tip of the shaft 10 and configured to receive the fiducial pin 110, 112 therein.

Figure 34:
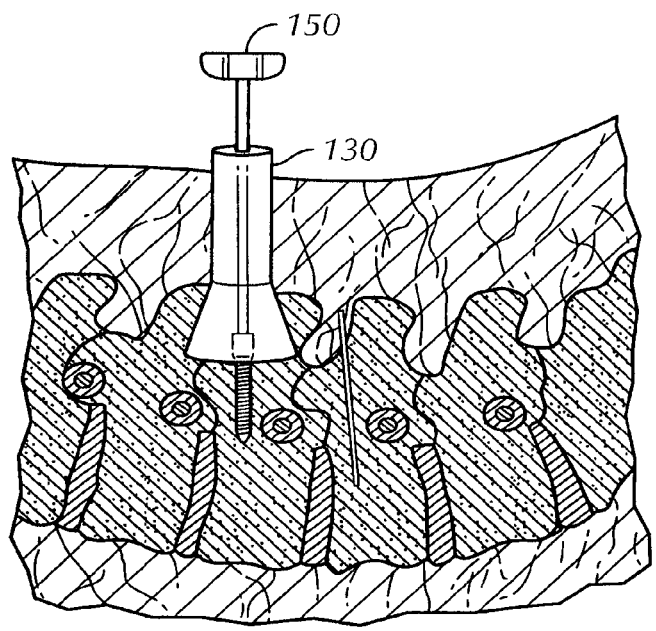
FIG. 34 is a perspective, cross-sectional view of a patient's spine after one pedicle screw has been implanted into a designated location of a spinal pedicle, in accordance with one embodiment of the invention.

FIG. 34 illustrates a perspective cross-sectional view of the patient's spinal column after a pedicle screw 2 has been inserted into a first pedicle of the spine using an insertion device 150. Various types of insertion devices 150 known in the art may be used to insert the pedicle screw 2. As shown in FIG. 34, after a first pedicle screw 2 has been implanted, the retractor 130 is adjusted and moved slightly to provide space and a visual field for insertion of a second pedicle screw at the location of the second fiducial pin 110, 112.

Figure 35:
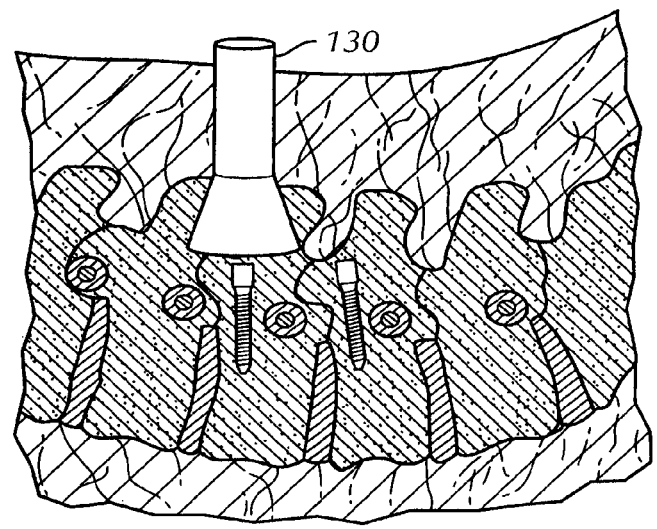
FIG. 35 is a perspective, cross-sectional view of a patient's spine after two pedicle screws have been implanted into designated locations of two adjacent spinal pedicles, in accordance with one embodiment of the invention.

FIG. 35 provides a perspective, cross sectional view of the patient's spinal column after two pedicle screws 2 have been implanted in two respective adjacent pedicles of the spine, in accordance with the present invention. After the pedicle screws 2 are in place, a flexible rod, plate or hybrid connection unit as described above with respect to FIGS. 4-20 may be connected to the pedicle screws to provide flexible stabilization of the spine. Thereafter, the retractor 130 is removed and the minimally invasive incision is closed and/or stitched.

Figure 36A:
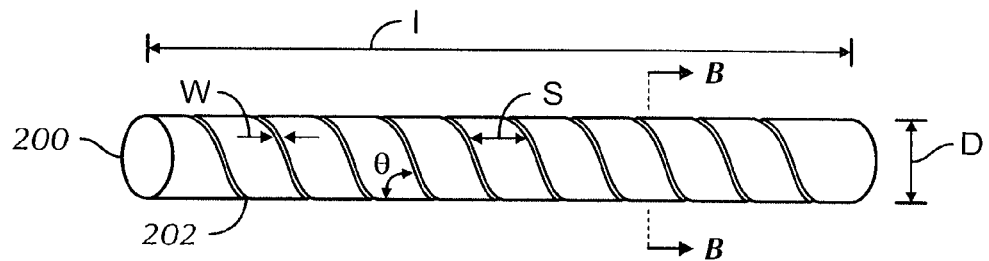
FIG. 36A is perspective view of a flexible rod for spinal fixation having a spiral groove cut therein, in accordance with one embodiment of the present invention.

FIG. 36A illustrates a perspective view of a flexible rod 200 for spinal fixation, in accordance with a further embodiment of the invention. The rod 200 is configured to be secured by securing members 2 as described above with reference to FIGS. 1-3. In preferred embodiments, the rod 200, and rods 210, 220, 230 and 240 described below, are comprised of a solid, cylindrically-shaped rod made of known biocompatible materials such as: stainless steel, iron steel, titanium, titanium alloy, NITINOL, and other suitable metal, metal-synthetic hybrid or non-metal materials or compositions, as discussed above. As shown in FIG. 36A, spiral grooves 202 are cut or formed along at least a portion of the length of the cylindrical body of the rod 200. In an exemplary embodiment, the length of the rod "l" may be between 4 and 8 centimeters (cm), and its cylindrical diameter "D" is between 4-8 millimeters (mm). The spiral grooves 202 have a width "w" between 0.1 and 0.5 mm and a spiral angle θ between 50 and 85 degrees from horizontal. The distance between spiral grooves 202 can be between 3 and 6 mm. However, as understood by those skilled in the art, the above dimensions are exemplary only and may be varied to achieve desired flexibility, torsion and strength characteristics that are suitable for a particular patient or application.

Figure 36B:
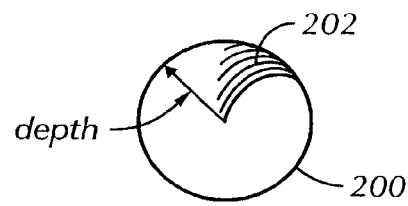
FIG. 36B provides a cross-sectional view of the flexible rod of FIG. 36A, taken along lines B-B of FIG. 36A.

FIG. 36B illustrates a cross-sectional view of the flexible rod 200, taken along lines B-B of FIG. 36A. As shown, spiral groove 202 is cut toward the center longitudinal axis of the cylindrical rod 200. The groove may be formed continuously in a spiral fashion, as a helix or an interrupted helix for a solid or hollow rod, or are as disconnected circumferential grooves for a solid rod. If hollow rods have disconnected circumferential grooves formed in them, the grooves can only partially penetrate the rod material to avoid discontinuities. In one embodiment, the depth of the groove 202 is approximately equal to the cylindrical radius of the rod 200, as shown in FIG. 36B, and penetrates as deep as the center longitudinal axis of the cylindrical rod 200. However, the cross sectional area and shape of the rod, groove depth, groove width, groove cross-section shape, and groove to groove spacing of the grooved portion of the longitudinal member can be varied to adjust mechanical and structural characteristics as desired. For example, deepening or widening grooves increases flexibility, while increasing groove-to-groove spacing decreases flexibility. This can be used to modify extent of rod bending at a fixed bending force, custom tailor the bent shape of the rod, and equalize mechanical stresses in the rod during bending in order to minimize material fatigue and improve rod reliability.

Figure 37A:
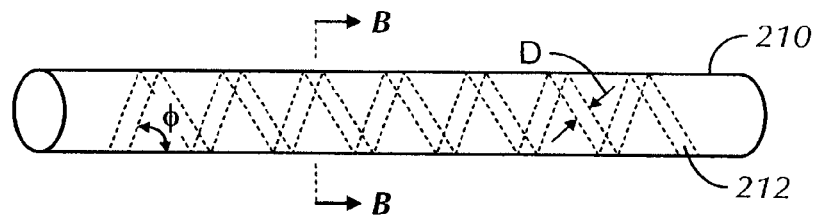
FIG. 37A illustrates a perspective view of a flexible rod for spinal fixation having transverse tunnels within the body of the rod, in accordance with one embodiment of the invention.

FIG. 37A illustrates a flexible rod 210 for spinal fixation in accordance with another embodiment of the invention. The rod 210 includes a plurality of transverse holes or tunnels 212 drilled or formed within the body of the rod 210. In one embodiment, the tunnels 212 pass through a center longitudinal axis of the cylindrical rod 210 at an angle (d) from horizontal. The openings for each respective tunnel 212 are located on opposite sides of the cylindrical wall of the rod 210 and adjacent tunnels 212 share a common opening on one side of the cylindrical wall, forming a zigzag pattern of interior tunnels 212 passing transversely through the central longitudinal axis of the rod 210, as shown in FIG. 37A. In one embodiment, the diameter D of each tunnel 212 may be varied between 0.2 to 3 mm, depending the desired mechanical and structural characteristics (e.g., flexibility, torsion and strength) of the rod 210. However, it is understood that these dimensions are exemplary and other diameters D may be desired depending on the materials used and the desired structural and mechanical characteristics. Similarly, the angle from horizontal Φ may be varied to change the number of tunnels 212 or the distance between adjacent tunnels 212.

Figure 37B:
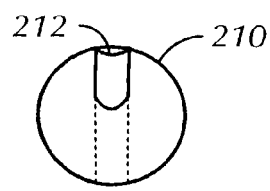
FIG. 37B is a cross-sectional view of the flexible rod of FIG. 37A, taken along lines B-B of FIG. 37A.

FIG. 37B illustrates a cross-sectional view of the flexible rod 210 taken along lines B-B of FIG. 37A. The tunnel 212 cuts through the center cylindrical axis of the rod 210 such that openings of the tunnel 212 are formed at opposite sides of the cylindrical wall of the rod 210.

Figure 38A:
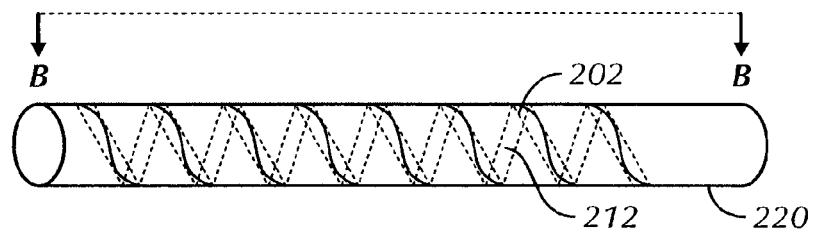
FIG. 38A is a perspective view of a flexible rod for spinal fixation having a spiral groove cut therein and transverse tunnels in the body of the rod, in accordance with a further embodiment of the invention.

FIG. 38A illustrates a perspective view of a flexible rod 220 for spinal fixation, in accordance with a further embodiment of the invention. Rod 220 incorporates the spiral grooves 202 described above with reference to FIGS. 36A and 36B as well as the transverse tunnels 212 described above with respect to FIGS. 37A and 37B. The spiral grooves 202 are cut into the surface of the cylindrical wall of the rod 220 toward a center longitudinal axis of the rod 220. As discussed above, the dimensions of the spiral grooves 202 and their angle from horizontal θ (FIG. 36A) may be varied in accordance with desired mechanical and structural characteristics. Similarly, the dimensions of the transverse tunnels 212 and their angle from horizontal Φ (FIG. 37A) may be varied in accordance with desired mechanical and structural characteristics. In one embodiment, the angles θ and Φ are substantially similar such that the openings of the tunnels 212 substantially coincide with the spiral grooves 202 on opposite sides of the cylindrical wall of the rod 220.

Figure 38B:
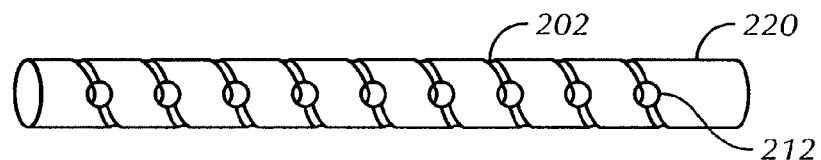
FIG. 38B is a top view of the flexible rod of FIG. 38A, from the perspective of lines B-B of FIG. 38A.

FIG. 38B shows a top view of the flexible rod 220 taken along the perspective indicated by lines B-B of FIG. 38A. As shown in FIG. 38B, the openings of the tunnels 212 coincide with the spiral grooves 202. By providing both spiral grooves 202 and transverse tunnels 212 within a solid rod 220, many desired mechanical and structural characteristics that are suitable for different patients, applications and levels of spinal fixation may be achieved.

Figure 39A:
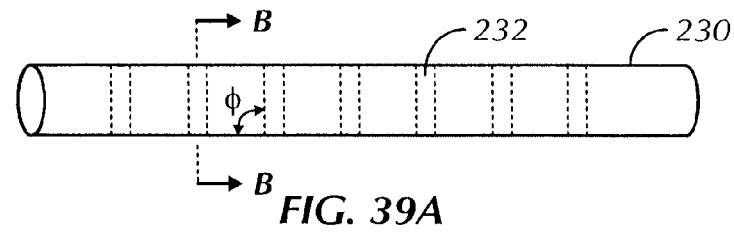
FIG. 39A is a perspective view of a flexible rod for spinal fixation having transverse tunnels within the body of the rod, in accordance with another embodiment of the invention.

FIG. 39A illustrates a flexible rod 230 for spinal fixation, in accordance with another embodiment of the invention. The rod 230 includes a plurality of transverse tunnels 232 formed in the body of the rod 230. The tunnels 232 are substantially similar to the tunnels 212 described above with respect to FIGS. 37A and 37B, however, the tunnels 232 are not linked together in a zigzag pattern. Rather, each tunnel 232 is substantially parallel to its immediate adjacent tunnels 232 and the openings of one tunnel 232 do not coincide with the openings of adjacent tunnels 232. As shown in FIG. 39A, the angle from horizontal Φ in this embodiment is approximately 90 degrees. However, it is understood that other angles Φ may be incorporated in accordance with the present invention. It is further understood that the dimensions, size and shape of the tunnels 232 (as well as tunnels 212) may be varied to achieve desired mechanical and structural characteristics. For example, the cross-sectional shape of the tunnels 212 and 232 need not be circular. Instead, for example, they may be an oval or diamond shape, or other desired shape.

Figure 39B:
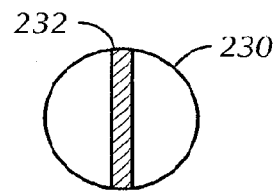
FIG. 39B is a cross-sectional view of the flexible rod of FIG. 39A, taken along lines B-B of that figure.
Figure 39C:
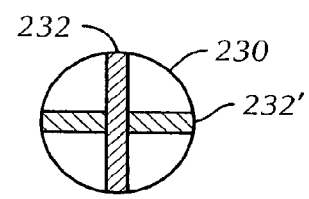
FIG. 39C is an alternative cross-sectional view of the flexible rod of FIG. 39A, taken along lines B-B of that figure, having substantially orthogonal transverse tunnels in the body of the rod, in accordance with a further embodiment of the invention.

FIG. 39B illustrates a cross-sectional view of the rod 230 taken along lines B-B of FIG. 39A. As shown in FIG. 39B, the transverse tunnel 232 travels vertically and transversely through the center longitudinal axis of the rod 230. FIG. 39C illustrates a cross-sectional view of a further embodiment of the rod 230, wherein an additional transverse tunnel 232' is formed substantially orthogonal to the first transverse tunnel 232 and intersect the first transverse tunnel 232 at the center, cylindrical axis point. In this way, further flexibility of the rod 230 may be provided as desired.

Figure 40A:
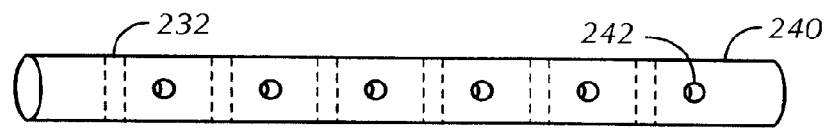
FIG. 40A illustrates a perspective view of a flexible rod for spinal fixation, in accordance with a further embodiment of the invention.
Figure 40B:
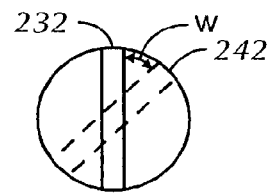
FIG. 40B illustrates a cross-sectional view of a flexible rod for spinal fixation in accordance with a further embodiment of the invention.

FIG. 40A illustrates a perspective view of a flexible rod 240, in accordance with a further embodiment of the invention. The rod 240 includes a plurality of interleaved transverse tunnels 232 and 242 which are substantially orthogonal to each other and which do not intersect, as shown in FIG. 40A. In another embodiment, a cross-sectional view of which is shown in FIG. 40B, adjacent tunnels 232 and 242 need not be orthogonal to one another. Each tunnel 232, 242 can be offset at a desired angle ω from its immediately preceding adjacent tunnel 232, 242. As can be verified by those of skill in the art, without undue experimentation, by varying the dimensions of the tunnels, their numbers, and their angular directions with respect to one another, various desired mechanical and structural characteristics for flexible rods used in spinal fixation devices may be achieved.

Figure 41A:
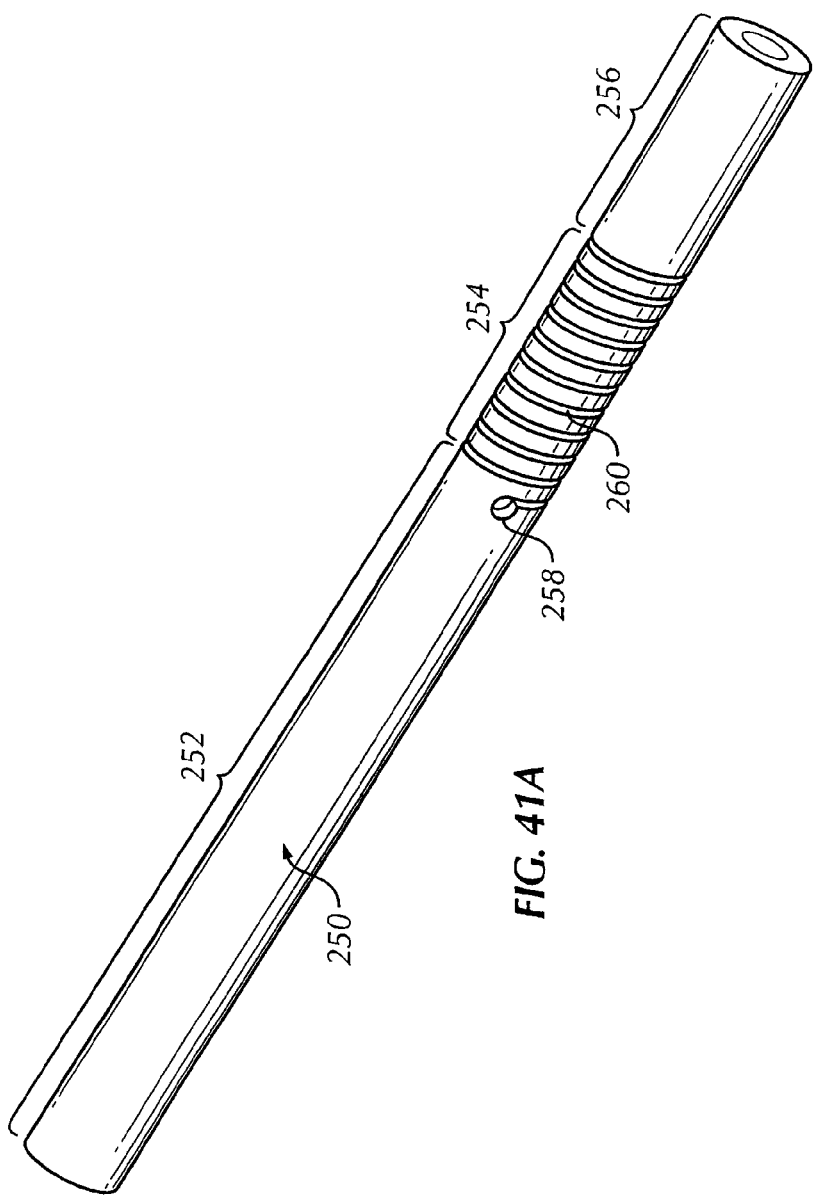
FIG. 41A illustrates a perspective view of a flexible longitudinal member connection unit in accordance with one embodiment of the invention.

Sometimes for multi-level spinal fixation procedures, as shown in FIG. 22B for example, it may be desirable for one spinal joint to be rigidly fixed, while an adjacent spinal joint is dynamically (flexibly) stabilized. An embodiment of a longitudinal member to accomplish this function is shown in FIG. 41A. Axial portion 254 of longitudinal member 250 is grooved to provide increased flexibility for bending, whereas axial portions 252 and 256 are not grooved and remain relatively rigid. The hole 258 is used to terminate the groove to prevent the formation of cracks and improve reliability. The use of such holes of expanded diameter to terminate grooves or slots in materials is well known in the art as a means of reducing peak mechanical stresses in materials and reducing the likelihood of material failure.

Figure 41B:
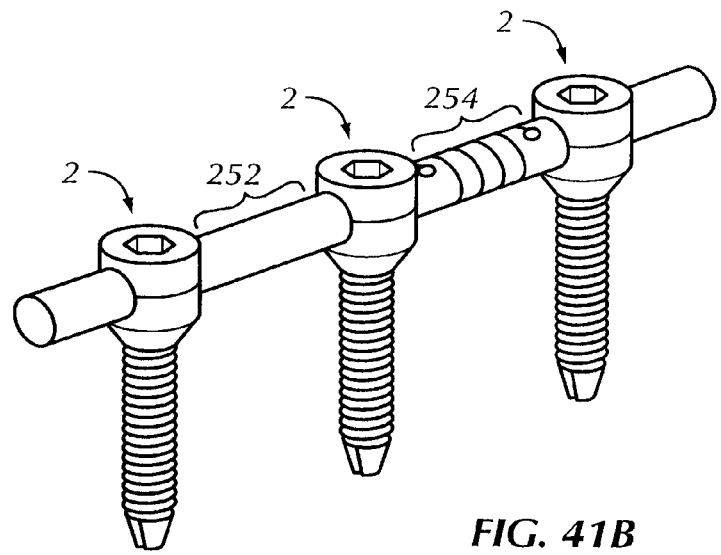
FIG. 41B illustrates a perspective view of the connection unit of FIG. 41A assembled with securing members.

FIG. 41B illustrates the assembly of the rod 250 of FIG. 41A configured to be secured to a patient's spine using at least three securing members 2 (FIG. 3) having a flexible section 254 disposed between a first pair of securing members 2 and a non-flexible section 252 disposed between a second pair for securing members 2.

Figure 41C:
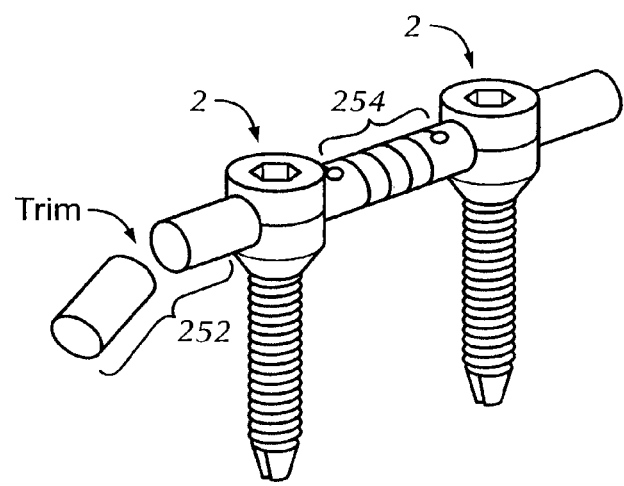
FIG. 41C illustrates a perspective view of a flexible longitudinal member trimmed to length and assembled with securing members.

As a further embodiment illustrated in FIG. 41C, an extended ungrooved section 252 can accommodate a range of positions for a single securing member 2 to be placed. In another embodiment, extended ungrooved sections can be symmetrically disposed at either end of a grooved section. It is appreciated that the extended length of section 252 provides a "one size fits all" longitudinal member 250 that can accommodate various distances between the pedicle bones of adjacent vertebrae. As shown in FIG. 41C, the distance between the adjacent securing members, 2 and 2', may be adjusted by selecting the location of the securing member 2 on section 252. Any excess length of section 252 can then be trimmed away or removed.

Groove parameters such as groove depth, groove width, groove cross-section shape or profile, and groove to groove spacing of the grooved portion 254 can be uniformly constant for uniform structural and mechanical characteristics along the axis of the grooved portion 254. Sometimes it is advantageous to have axially varying structural and mechanical characteristics for the longitudinal member in order to control local mechanical stress levels, custom tailor bending shapes, or affect resistance to bending in all bending directions or in selected bending directions. The cross-sectional area of a cylindrical (for example) hollow longitudinal member can be changed by changing the outer diameter, while maintaining constant wall thickness for the hollow cylinder. Another embodiment is to modify the wall thickness by adjusting the internal diameter (i.e. the diameter of the cavity within the cylinder) while keeping the outer diameter of the hollow cylinder constant. Still other embodiments simultaneously vary the external diameter and the internal diameter. It is easily seen how the above arguments also apply to longitudinal members with shapes that are not cylindrical.

Figure 42A:
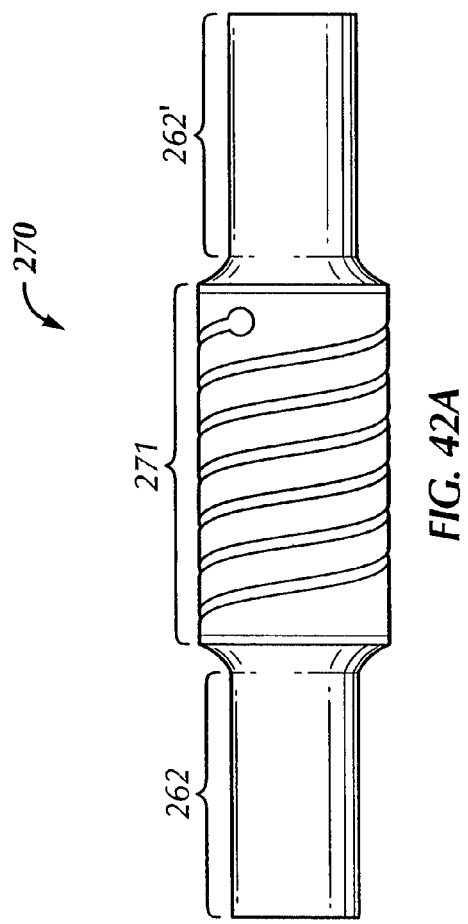
FIG. 42A illustrates a side view of a flexible longitudinal member connection unit in accordance with a further embodiment of the invention.

FIG. 42A illustrates a side view of a flexible, spirally grooved stabilization device 270 in accordance with an embodiment of the invention. The spirally grooved section 271 has an expanded outer diameter relative to ungrooved sections 262 and 262'. Whereas the spiral groove imparts increased flexibility to section 271, it would also impart greater per unit area material strain to section 271 relative to ungrooved sections 262 and 262' because of reduced cross-sectional material area in section 271, due to the presence of the grooves, if the outer diameter of spirally grooved section 271 were the same as the outer diameter of the ungrooved sections 262 and 262'. Expanding the outer diameter of section 271 can maintain acceptable material stress levels during the flexing of the spirally grooved section 271 for both the spirally grooved section 271, and the ungrooved sections 262 and 262'.

In one embodiment, if the longitudinal member of FIG. 42A is hollow, the inner diameter of the cavity of the spirally grooved section 271 can be the same as the inner diameter of the cavity of the ungrooved sections 262 and 262', whereas the outer diameter of the grooved flexible section 271 is increased to reduce material stresses during bending and/or vary the flexibility of the grooved section 271.

Figure 42B:
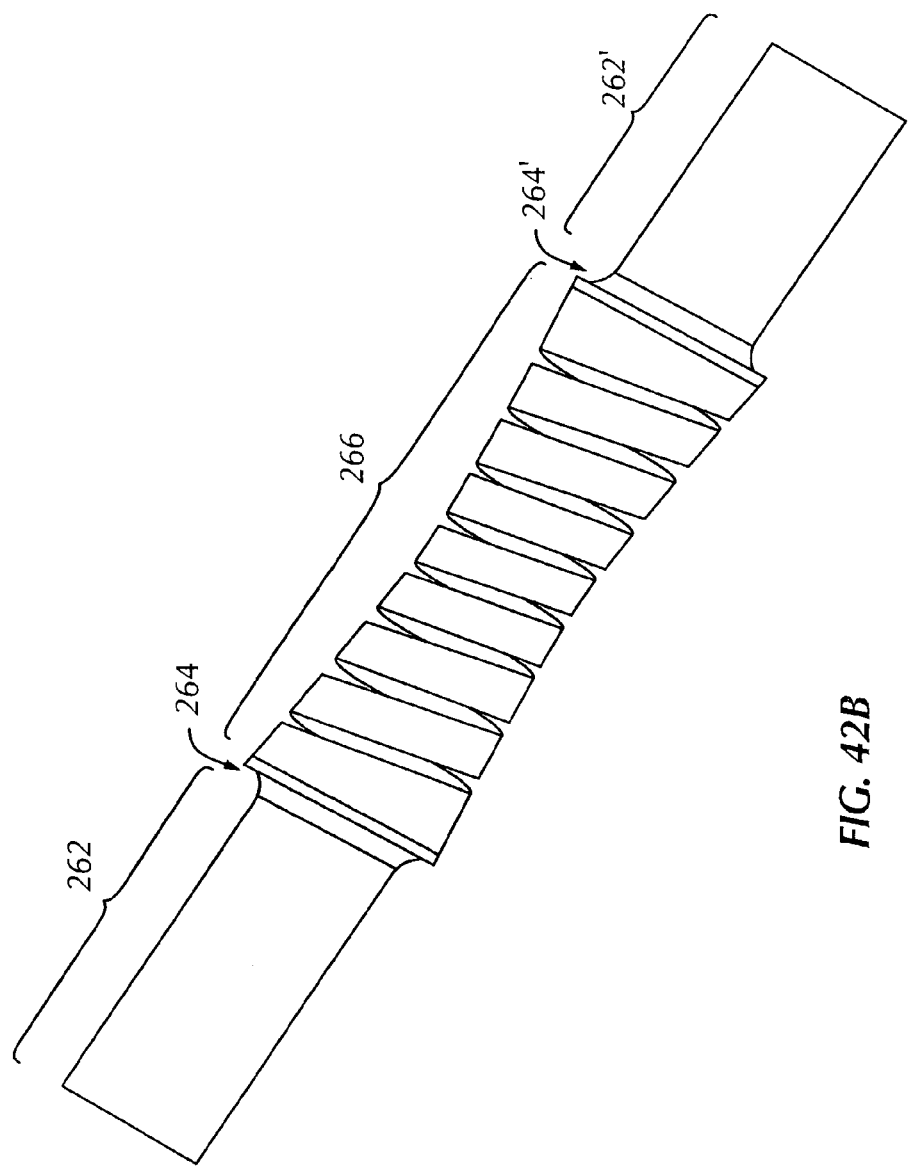
FIG. 42B illustrates a side view of a flexible longitudinal member connection unit in accordance with another embodiment of the invention.

FIGS. 42A and 42B (discussed below) illustrate examples of a longitudinal spinal stabilization device wherein a flexible section has a different cross-sectional profile (e.g., outer diameter (in the case of a cylindrical rod) or perimetric shape than that of corresponding end portions of the longitudinal stabilization device.

In a further embodiment, the cross-sectional profile (e.g., outer diameter) of the grooved flexible section is kept the same as the cross-sectional profile (e.g., outer diameter) of the ungrooved sections, whereas the inner diameter of the cavity of the grooved flexible section is reduced relative to the inner diameters of the cavities of the ungrooved sections. This has a similar material stress reduction effect as described above.

In still further embodiments of the present invention, both inner and outer diameters of the grooved flexible section can be varied with respect to the inner and outer diameters of the ungrooved sections to reduce material strain differences between the sections.

FIG. 42B illustrates a side view of another embodiment of the present invention that accomplishes variation in flexibility along a longitudinal axis by adjusting the cylindrical diameter or cross-sectional profile of the grooved section 266 (while maintaining a constant inner cavity diameter for the case of a hollow longitudinal member) in order to achieve reduced mechanical stresses in the vicinity of transition sections 264 and 264', between the grooved section 266 and ungrooved sections 262 and 262', respectively. The outer diameter of the grooved section 266 is smallest near a central portion of the grooved section 266 and gradually expands toward the ungrooved sections 262. This provides more cross-sectional material area to distribute forces through, thereby reducing per unit area stress in the regions of the grooved section 266 near the transition sections 264 and 264'.

Figure 43A:
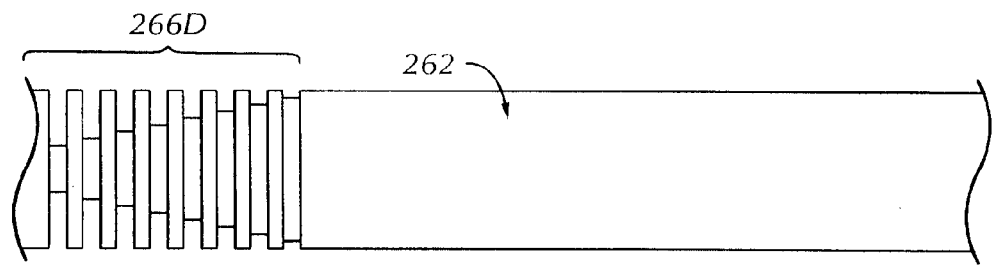
FIG. 43A illustrates a side view of a flexible longitudinal member connection unit in accordance with another embodiment of the invention.
Figure 43B:
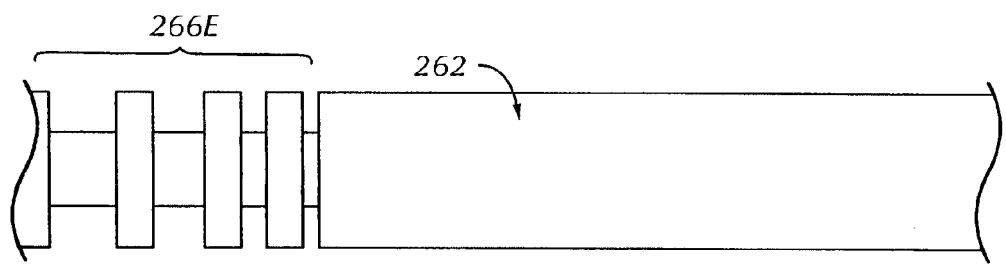
FIG. 43B illustrates a perspective view of a flexible longitudinal member connection unit in accordance with another embodiment of the invention.
Figure 43C:
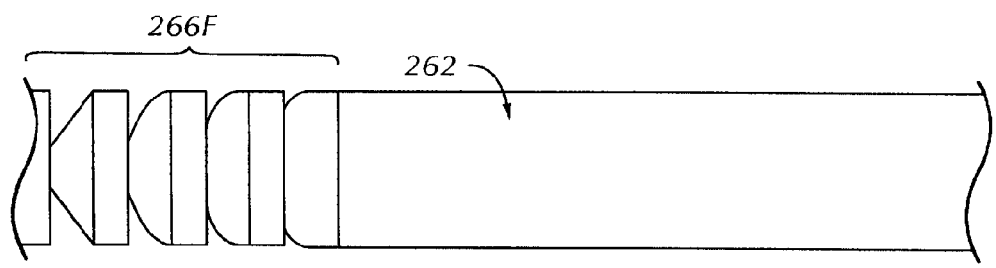
FIG. 43C illustrates a side view of a flexible longitudinal member connection unit in accordance with another embodiment of the invention.
Figure 43D:
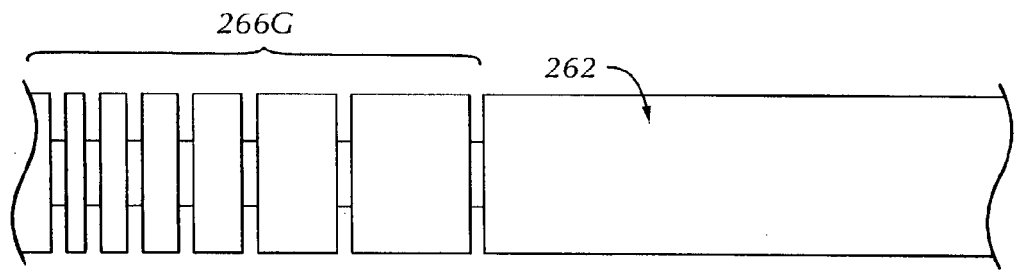
FIG. 43D illustrates a side view of a flexible longitudinal member connection unit in accordance with another embodiment of the invention.

In another embodiment, axial variations of groove depth, groove width, groove cross-section shape, and groove to groove spacing can also achieve axially variant flexibility and mechanical characteristics, either alone or in combination with variance of the cylindrical cross-section as discussed above. For example: (i) tapering the groove depth from a maximum near the center of a grooved section to near zero at a boundary with a non grooved section (FIG. 43A); (ii) tapering the groove width from a maximum near the center of a grooved section to near zero at a boundary with a non grooved section (FIG. 43B); (iii) transitioning groove shape from one permitting maximum flexure near the center of a grooved section to a shape providing reduced flexure at a boundary with a non grooved section (FIG. 43C); or (iv) expanding groove to groove spacing from a minimum near the center of a grooved section to a maximum at a boundary with a non grooved section (FIG. 43D).

Figure 44:
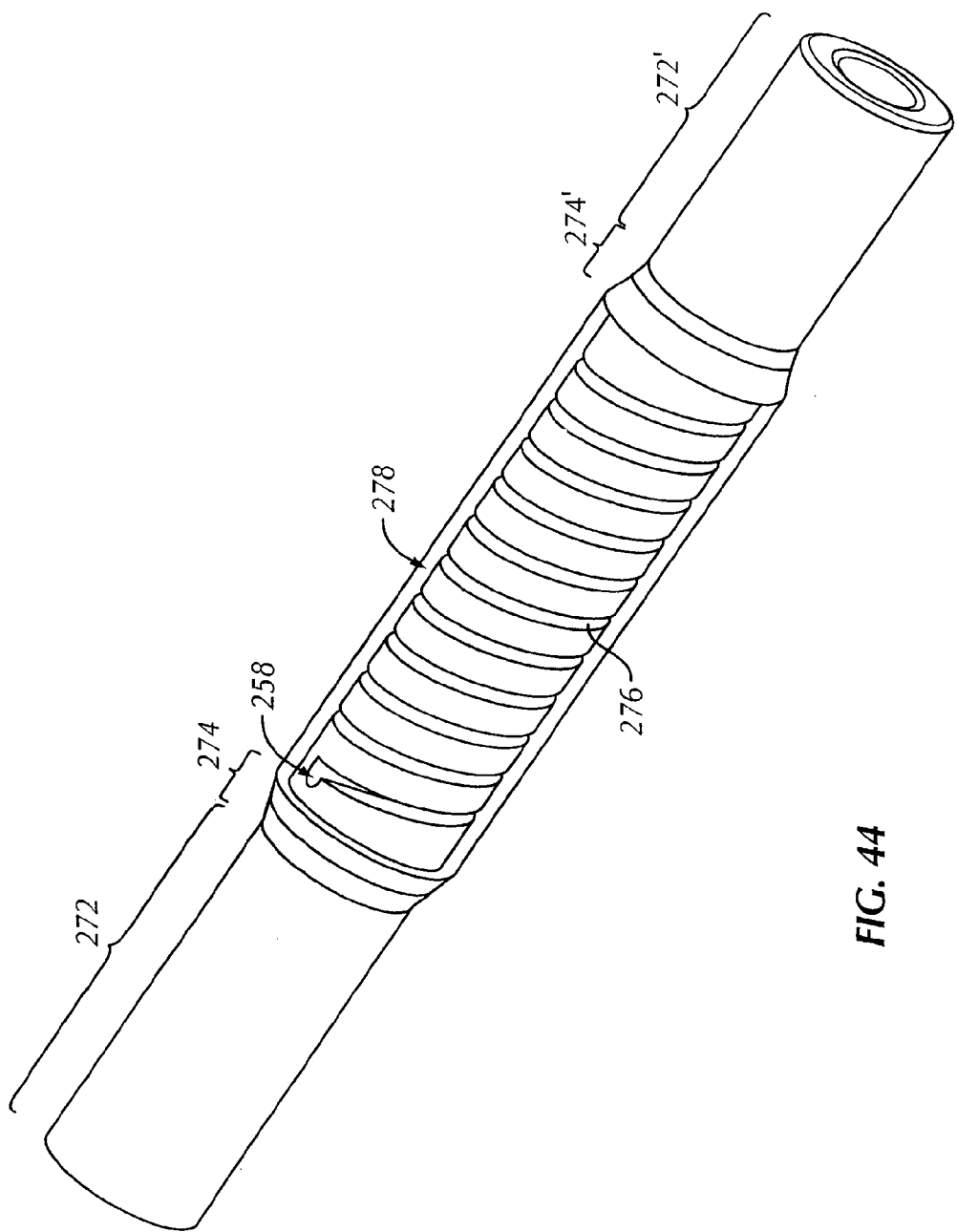
FIG. 44 illustrates a perspective view of a flexible longitudinal member connection unit in accordance with a further embodiment of the invention.

FIG. 44 illustrates a longitudinal member with an elastomer cladding 278 around the grooved section 276. In this embodiment, elastomer cladding 278 covers only grooved section 276 and does not cover ungrooved sections 272. Also optional tapers 274 are formed in the longitudinal member to provide for a smooth surface transition between clad and unclad sections. These optional tapers 274 also fixate the longitudinal position of the cladding. Alternately the cladding may be extended onto an ungrooved section 272. The elastomer cladding may (i) contact only the surface of the longitudinal member, (2) additionally penetrate into the grooves of the longitudinal member, or (3) if the longitudinal member is hollow, additionally penetrate to and at least partially fill the inside of the longitudinal member. The elastomer cladding provides additional control over the axial and flexural stability of the longitudinal member, as well as providing a barrier between tissues and the grooved section.

The elastomer cladding can consist of any of a variety of medical grade elastomers, including, for example, silicone, polyurethane, polycarbonateurethane and silicone-urethane copolymers. The cladding can be applied to the longitudinal member using a variety of techniques that are well known in the art. In one technique, a thermoplastic or thermosetting resin can be injected into a heated mold surrounding the desired section of the longitudinal member, while it is affixed within a mold. An advantage of this injection molding process is that it can accommodate cladding material that are not of sufficiently low viscosity for application by alternate means at room temperature and pressure. A further advantage of injection molding is that the shape of the exterior of the cladding is determined by the shape of the mold that is used. Another injection molding advantage is the reproducible penetration of groove interstices and the interior of hollow longitudinal members. Alternative molding techniques include compression molding and transfer molding.

Other cladding application methods include liquid injection molding, dipping, spraying, or painting with a mechanical applicator such as a paintbrush. These methods require that the cladding material be applied in a low viscosity form. For an example a resin for application could be suspended in a solvent that evaporates after application. In another example, the cladding material is applied in a low viscosity form and subsequently cured through chemical, heat, or radiation methods. It is sometime useful to mask parts of the longitudinal member where application of the cladding material is not desired.

Figure 45A:
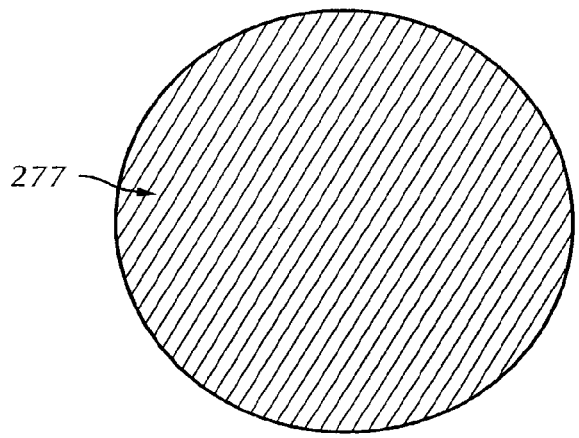
FIG. 45A illustrates a cross-section view of a flexible longitudinal member connection unit in accordance with an embodiment of the invention.
Figure 45B:
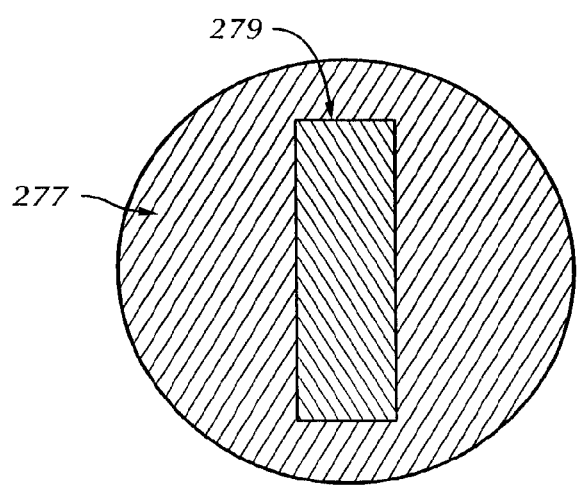
FIG. 45B illustrates a cross-section view of a flexible longitudinal member made of two types of material in accordance with another embodiment of the invention.

FIG. 45A illustrates a uniform cross-section of the flexible section of a longitudinal member made of a material 277. FIG. 44B illustrates a non-uniform cross-section of a rod as a flexible section of a longitudinal member made of a material 277 that includes a section made of another material 279. Clearly the rod of FIG. 45A will exhibit the same bending behavior with applied force in both the x and y directions. If the materials of sections 320 and 330 have different bending characteristics, the rod of FIG. 45B will exhibit different bending behavior with applied force for the x and y directions. For example, if material 279 in FIG. 45B is stiffer than material 277, the rod will bend more easily in the x direction than in the y direction.

Figure 46A:
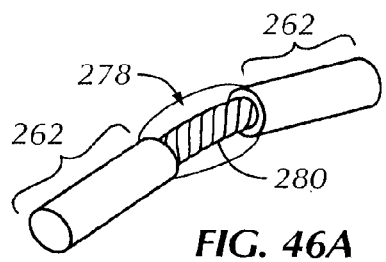
FIGS. 46A-C illustrate perspective views of a metal-hybrid longitudinal member with an elastomer cladding, in accordance with various embodiments of the invention.
Figure 46B:
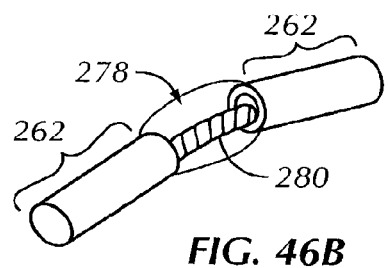

FIG. 46A illustrates another embodiment of a metal hybrid longitudinal member with an elastomer cladding 278 around a wire portion 280 of the longitudinal member. In this embodiment, elastomer cladding 278 surrounds a braided wire 280 between two unclad end portions 262. The wire may also be a single wire, multiple wires that are not braided (not shown), and may be coaxial with the end portions 262 or positioned eccentrically with respect to the longitudinal axis of the end portions 262 as shown in FIG. 46B. The wire portion 280 may be straight as shown in FIG. 46A or curved, such as the wire 281 shown in FIG. 46C. A straight wire 280 between end portions 262 provides greater resistance to tension than a curved wire 281, which straightens as the longitudinal member elongates under tension. In one embodiment, the end portions 262 and wire 280 may be made from any desired and suitable biocompatible metal or metal-synthetic hybrid material discussed above with respect to rod 4 and wire 32. In further embodiments, the cladding 278 may be made from any one or combination of suitable biocompatible synthetic or non-metal materials discussed above.

Figure 46C:
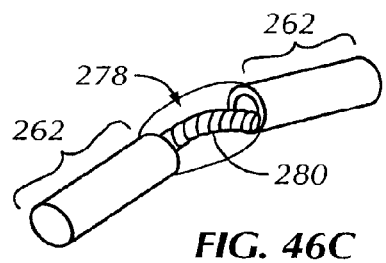

The stiffness of the metal hybrid longitudinal member in FIGS. 46A-C may be modified by varying the wire configuration within the elastomer cladding 278 as described above, or by varying the physical geometry of the wire 280 and/or cladding 278. Those skilled in the art will recognize that stiffness may be altered by changing the length and/or diameter of the wire portion 280 and cladding 278, the ratio of diameters, or the number and placement of wires, for example.

Figure 47A:
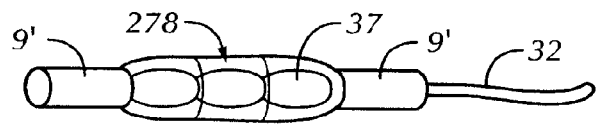
FIGS. 47A-B illustrate perspective views of a longitudinal member having at least one spacer and an elastomer, in accordance with various embodiments of the invention.

FIG. 47A illustrates yet another embodiment of a flexible connection unit having one or more spacers 37 between two rigid end portions 9' with an elastomer cladding 278 covering the one or more spacers 37. The connection unit further includes a wire 32, which traverses a longitudinal axial channel or hole in each of the spacers 37. In one embodiment, as shown in FIG. 47A, the spacers 37 occupy substantially all of the space between the end portions 9' such that the plurality of spacers 37 are maintained in a substantially fixed position along a longitudinal axis direction between the end portions 9'. In other words, the spacers 37 do not move or slide substantially with respect to the wire 32 in the longitudinal direction because there is no space between the end portions 9' to do so. Each spacer 37 abuts an adjacent spacer 37 and/or end portion 9' such that it does not have room to slide with respect to the wire 32 or other flexible member located in the longitudinal axial channels of the spacers 37 between the end portions 9'. A cladding 278 is formed around each spacer 37 or around the entire group of spacers 37. It is appreciated that the combination of the spacer 37 and cladding 278 forms a composite or hybrid spacer wherein the spacer 37 provides a first material of the hybrid spacer and the cladding provides a second material of the hybrid spacer. In one embodiment, the spacers 37 may be made from a biocompatible metal or metal-synthetic hybrid materials, as discussed above, and the cladding 278 may be made from any one or combination of suitable biocompatible synthetic or non-metal materials discussed above.

Figure 47B:
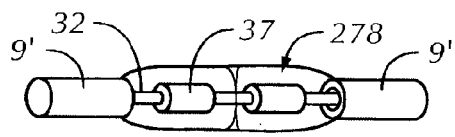

In another embodiment, the spacers 37 may be positioned along the wire 32 such that there is room between adjacent spacers 37 and the end portions 9', as shown in FIG. 47B. A cladding 278 is formed around the spacers 37 and the wire 32 such that substantially all of the space between adjacent spacers 37 and the end portions 9' is occupied by the cladding 278. Thus, the cladding 278 limits the motion of spacers 37 and the wire 32 encased therein and provides additional rigidity to the flexible portion between the end portions 9'. The cladding 278, spacers 37 and wire 32 may be made from any suitable material, including those discussed above with respect FIGS. 9, 10 and 47A, for example.

The cladding 278 in FIGS. 47A & B is shown to encapsulate all of each of the metal-hybrid spacers 37 between the end portions 9'. Those skilled in the art will recognize that the stiffness of the connection unit 36 may be altered by cladding only a portion of the spacers 37, for example the space between the metal portion of the spacers 37 and the wire 32, or the spaces between the spacers 37 and between the spacers 37 and the end portions 9'.

The stiffness of the flexible connection unit described in the various embodiments above may be altered by selecting various biocompatible materials. For example, the spacers 37 may be made of biocompatible metals (e.g. stainless steel, titanium, titanium alloys, tantalum, zirconium, cobalt chromium, and alloys of such materials). The spacers 37 may also be made from materials comprising known rigid polymers (e.g. UHMWPE, PEEK and polyurethane) or ceramics (e.g. alumina or zirconia).

Figure 48:
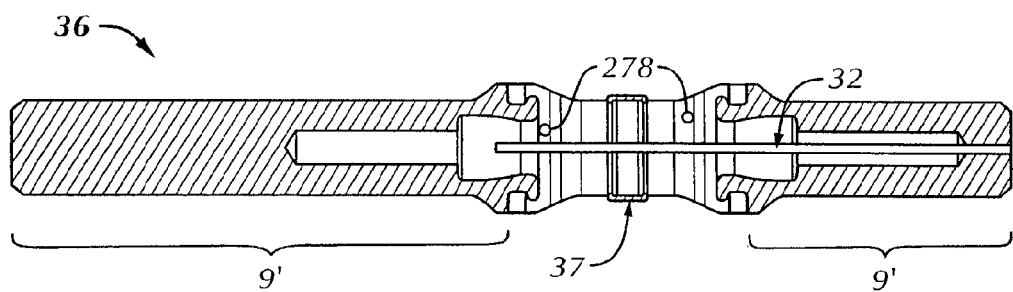
FIG. 48 illustrates a flexible connection unit having a spacer and an elastomer cladding, in accordance with another embodiment of the invention.

FIG. 48 illustrates a further embodiment of a flexible connection unit 36 having a metal spacer 37 between rigid end portions 9', with an elastomer cladding 278 surrounding at least part of the rigid spacer 37. The connection unit 36 further includes a flexible wire 32 positioned axially through the spacers 37 and end portions 9', wherein the spacer 37, end portions 9' and wire 32 are all physically separated by the elastomer cladding 278. In such an embodiment, all elements of the flexible connection unit can move relative to any other element under mechanical load, restricted only by the flex, stretch and compression characteristics of the elastomer cladding 278. Thus, the size and shape of the elements may be selected to withstand the loads on the human spinal column and to allow normal motion of the vertebrae to which the connection unit is attached. The metal spacer 37 and cladding 278 together form a metal-synthetic hybrid or composite spacer, wherein the elastomer cladding 278 separates the metal spacer 37 from respective rigid end portions 9' and the metal wire 32 so that they do not rub against each other, thereby minimizing the generation of wear debris. It is a further advantage of this embodiment that the connection unit is flexible in all directions or degrees of freedom, and therefore will permit flexion, extension, lateral bending and axial rotation of the spinal column without a fixed or rigid mechanical restriction in any direction. The elastomer cladding 278 in FIG. 48 is concentric with the flexible wire 32. In other embodiments (not shown), the wire 32 may be eccentrically located in the axial cavity of the spacer 37, or multiple wires 32, may be distributed throughout the axial cavity of the spacer 37.

The wire 32 shown in FIG. 48 is physically separated at both ends from the end portions 9'. This may be accomplished by cladding the wire 32 individually to create a metal-hybrid wire and assembling it with the end portions 9' prior to cladding the spacer 37. Alternatively the metal-hybrid wire 32 may be clad by extruding elastomer around the wire 32 or sliding it into a pre-formed extruded elastomer prior to assembly. The latter method of manufacturing has the advantage of allowing the wire 32 to slide along its axis within the elastomer cladding 278, thereby decreasing axial stiffness of the connection unit 36 relative to its flexural and shear stiffness. Those skilled in the art will recognize that if the flexible wire 32 is free to slide as described herein, then the flexural and shear stiffness of the connection unit 36 may be altered by varying the diameter of the wire 32, with minimal change in the axial stiffness of the connection unit 36. As known in the art, "flexural stiffness" relates to an amount that an object may bend and "shear stiffness" relates to an amount that an object can withstand lateral shear forces. "Axial stiffness" relates to an amount that an object can be stretched or compressed.

Figure 49:
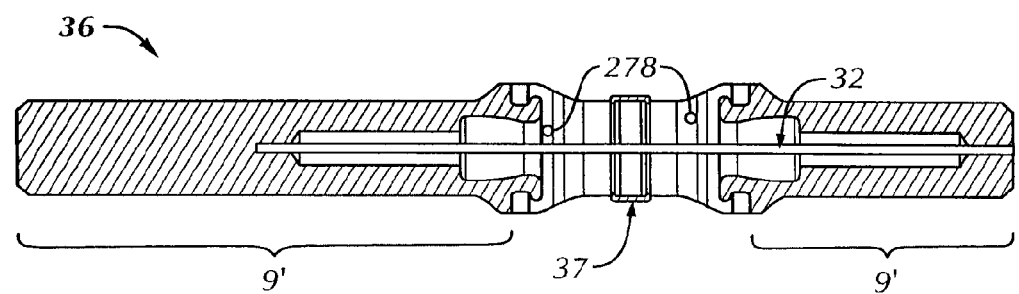
FIG. 49 illustrates a flexible connection unit having a spacer and an elastomer cladding, in accordance with another embodiment of the invention.

FIG. 49 illustrates a flexible connection unit identical to FIG. 48, except that each end of the wire 32, is in contact with the end portions 9'. In an alternate embodiment (not shown) one end of the wire 32 may be in contact with one end portion 9', while the opposite end of the wire 32 is separated from the other end portion 9' by cladding as described above. Contact between the wire 32 and the end portions 9' may be sliding contact or fixed contact such as a press fit assembly, welded assembly or brazed assembly. If both ends of the wire 32 are in fixed contact with the end portions 9', i.e. rigidly connected, the axial stiffness of the flexible connection unit is increased. A fixed contact at only one end of the wire 32, will have less effect on axial stiffness of the connection unit.

FIGS. 48 and 49 illustrate a metal-hybrid spacer that includes a metal spacer 37 that circumferentially surrounds an elastomer cladding 278. Thus, the spacer 37 is primarily clad on its inside surface. These embodiments may be easily manufactured by holding the metal portion of the spacer 37 in place relative to the end portions 9' in a mold, while the cladding 278 is applied. It is a further advantage of this embodiment that the circumferentially located spacer 37 limits the expansion and bending of the cladding 278 when the connection unit 36 is mechanically loaded. This limiting effect results in varying stiffness of the connection unit 36, particularly in axial compression, bending and shear. Those skilled in the art will recognize that stiffness of the connection unit 36 may be varied by varying the inside diameter, length and number of spacers 37.

The elastomer cladding 278 in various embodiments may be formed by a variety of methods, including a variety of molding techniques, extrusion, dipping and painting as described earlier. In an alternate embodiment, the elastomer cladding 278 is molded in place using an injection molded process and a biocompatible thermoplastic elastomer such as polycarbonate urethane (PCU). PCU has advantages of favorable biocompatibility, resistance to degradation and cracking, favorable fatigue properties and good adhesion to metal substrates in addition to its compatibility with the injection molding process. It is understood, however, that the cladding may be made from other suitable non-metal materials such as those described above. In further embodiments the surface of the spacers 37 and end portions 9' are prepared with one or more features or surface treatments to improve the durability of fixation of the elastomer cladding 278.

Figure 50A:
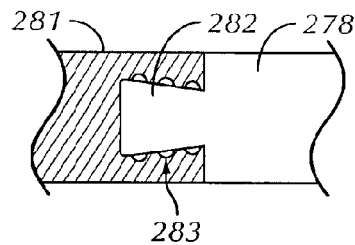
FIGS. 50A-D illustrate a variety of features for improved fixation of the elastomer cladding to a rigid surface, in accordance with various embodiments of the invention.
Figure 50B:
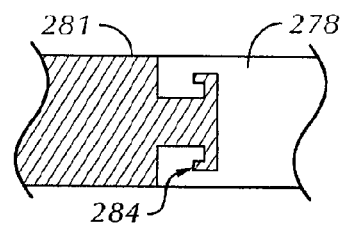
Figure 50C:
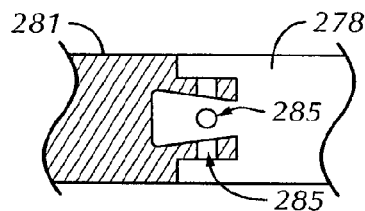
Figure 50D:
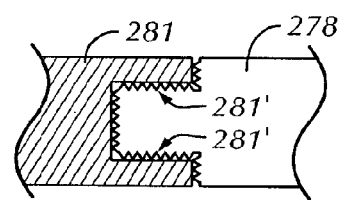

FIGS. 50A-D illustrate a variety of features for improved fixation of the elastomer cladding 278 to the surface of any rigid element 281. FIG. 50A illustrates an undercut cavity in the rigid element 281 wherein the body of the cavity 282 is larger than the neck 283, thereby capturing the elastomer cladding 278 within the cavity 282. The cavity further includes smaller undercut grooves 283 in the wall of the cavity for interdigitation of the elastomer cladding 278. The undercut grooves 283 and undercut cavity 282 may be utilized independently as well. Figure 50B illustrates an external barb 284 on the rigid element 281 around which the elastomer cladding 278 is molded. FIG. 50C illustrates holes 285 through the wall of the rigid element 281 through which the elastomer cladding 278 is molded. In one embodiment, the elastomer cladding 278 covers both the interior and exterior surfaces of the wall around the hole 285. Figure 50D illustrates a roughened surface 281' of the rigid element 281 at the interface with the elastomer cladding 278. The roughened surface may be formed by a variety of methods, including for example, grit blasting, bead blasting, plasma spraying, chemical etching and a variety of machining techniques. Any of the features illustrated in FIG. 50A-D may be used in combination with each other or in combination with surface treatments such as cleaning, passivation or chemical priming of the surface of the rigid element 281.

Figure 51:
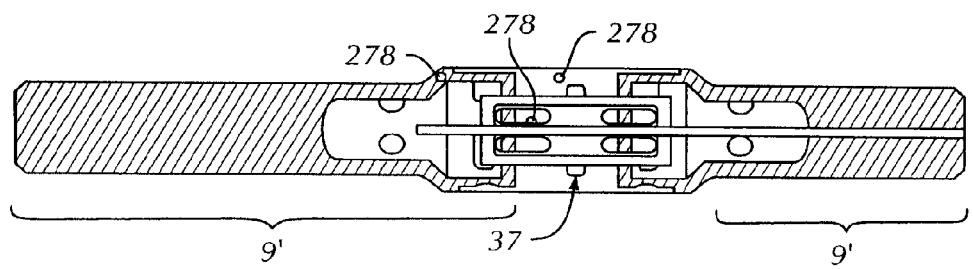
FIGS. 51-52 illustrates two respective embodiments of a flexible connection unit having at least one spacer and an elastomer cladding, in accordance with the invention.

FIG. 51 illustrates a further embodiment of a spacer 37 and end portions 9' in which the spacer 37 and end portions 9' are physically separated by the elastomer cladding 278 and are configured such that they reinforce the elastomer cladding 278 when the connection unit 36 is mechanically loaded. The spacer 37 and end portions 9' include overlapping portions that physically limit the shear displacement of the end portions 9' relative to each other without necessarily limiting axial displacement of the end portions 9' relative to each other. FIG. 51 is exemplary of any number of combinations of shapes of a spacer 37 and end portions 9' that may be used to vary stiffness of the connection unit 36 in one or more directions. Those skilled in the art will recognize that this objective may be accomplished with overlapping features or simply by increasing or reducing the spacing between the rigid spacer 37 and the end portions 9', or by adding additional spacers (not shown) and varying the spacing between adjacent spacers.

Figure 52:
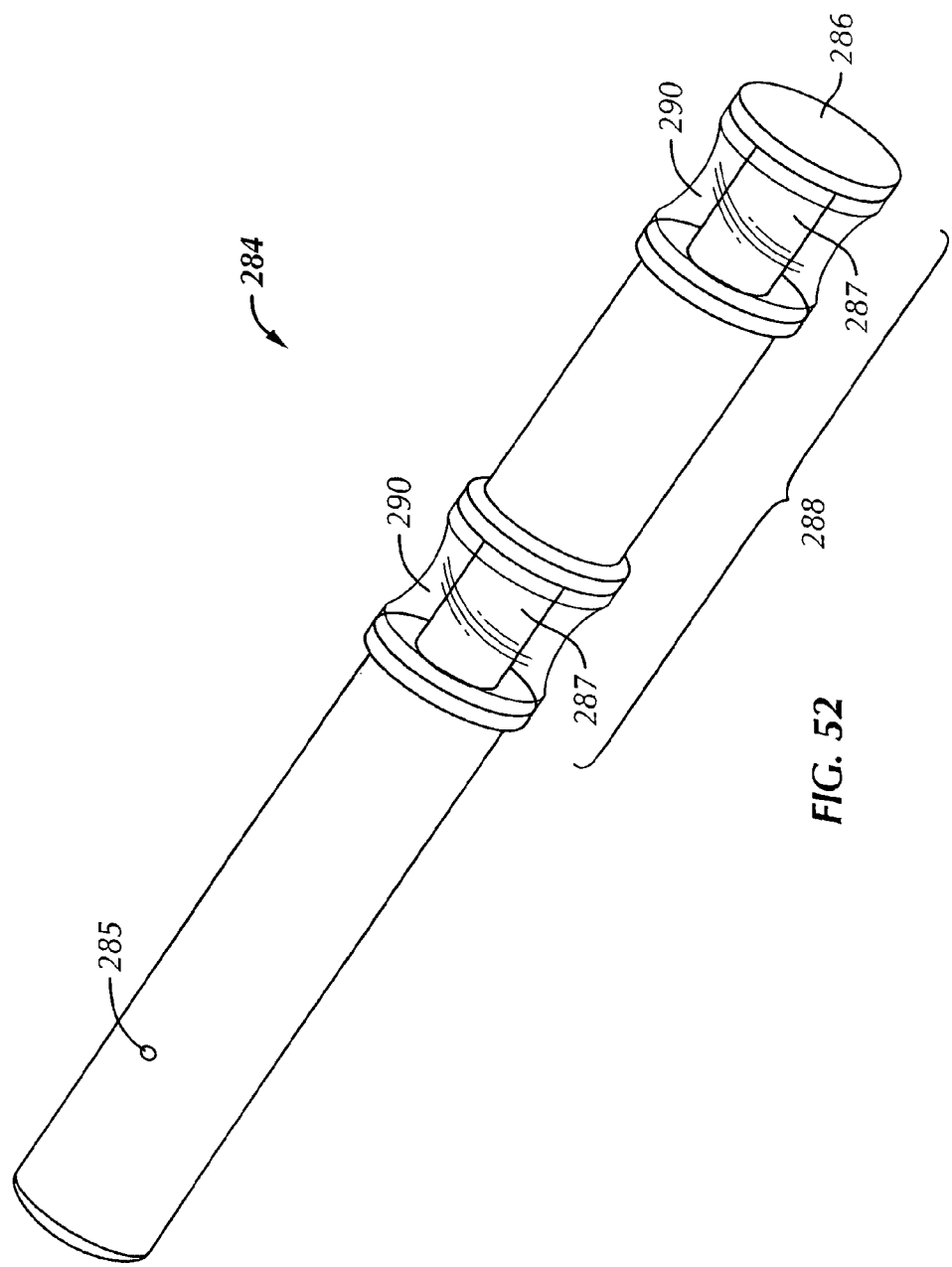

FIG. 52 illustrates another embodiment of a connection unit 284 having two rigid end portions 285 and 286, and a middle portion in which a flexible member 287 connects end portions 285 and 286 and traverses an axial hole in a metal-hybrid spacer 288. In one embodiment, metal-hybrid spacer 288 is formed from at least one metal and one elastomer material, such that the metal part of the spacer 289 is configured to be accepted and retained by a securing member such as a pedicle screw or laminar hook, and the elastomer part 290 of the spacer 288 is located on opposite sides of the metal part 289 and adjacent to respective end portions 285 and 286.

Referring to FIG. 52, when end portion 285 and metal spacer 289 are retained by respective securing members 2 (FIG. 2), for example, and affixed to adjacent vertebrae, the connection unit 284 provides stability while simultaneously permitting motion to the vertebrae in six degrees of freedom (i.e., x-axis, y-axis, z-axis, pitch, roll and yaw). Although the end portions 285 and 286 substantially limit the motion of the metal-hybrid spacer 288 in the longitudinal axial direction, the compressibility and elasticity of the elastomer part 290 on both sides of the metal spacer 289 allows for stabilized motion of the metal spacer 289 relative to the end portions 285 and 286 and/or flexible connecting member 287 in each of the six degrees of freedom while also providing a resistance and stability of motion in each of the six degrees of freedom. Thus, in one embodiment, the connection unit provides a greater range of dynamically stabilized motion. Additionally, in one embodiment, the elastomer cladding 290 comprises a high-friction material that resists sliding of the metal-hybrid spacer 288 on flexible middle portion 287, thereby providing further resistance to movement of the metal spacer 289 in the longitudinal axial direction. End portions 285 and 286 are connected to respective ends of metal-hybrid spacer 288 using any of the techniques discussed above or other known methods. End portion 285 is configured to have sufficient length to be accepted and retained by a pedicle screw or other type of securing member. When the metal part 289 of the hybrid spacer 288 is coupled to and secured to a securing member 2 (FIG. 3), for example, end portion 286 extends beyond the securing member 2 (on the side opposite the space between the two securing members 2). Thus, end portion 286 is configured to be short along the axis of the connection unit 284, in order to minimize the length of the connection unit 284 that extends beyond the securing member 2.

In another embodiment (not shown), the flexible member 287 may be located eccentric from the central longitudinal axis of the connection unit 284. This eccentric configuration provides different levels of stiffness, depending on the direction the connection unit 284 is bent. This may be advantageous if it is desired to provide a greater level of stiffness when the connection unit 284 is flexed during spinal extension (e.g., when a patient bends backward) and a lesser level of stiffness when the connection unit 284 is flexed during spinal flexion (e.g. when a patient bends forward). Additionally, or alternatively, different levels of stiffness v. direction of bending profiles may be achieved by applying different amounts or thicknesses of cladding 290 on one side of the connection unit 284 than on other sides of the connection unit 284. Additionally, different amounts and/or types of cladding materials 290 may be applied on either side of the spacer 289. Thus, the connection unit 284 can provide different levels of stiffness in different directions of movement of the spacer 289 and, hence, varying levels of stability can be provided to different directions of movement of a vertebra secured to the spacer 289 via a securing member 2. In these embodiments wherein the level of stiffness of the connection unit 284 depends on the direction of bending, appropriate markings (e.g., laser etchings, physical features, etc.) may be placed on the connection unit 284 to indicate the proper orientation of the connection unit 284 prior to securing the connection unit 284 to a patient's spine.

Figure 53:
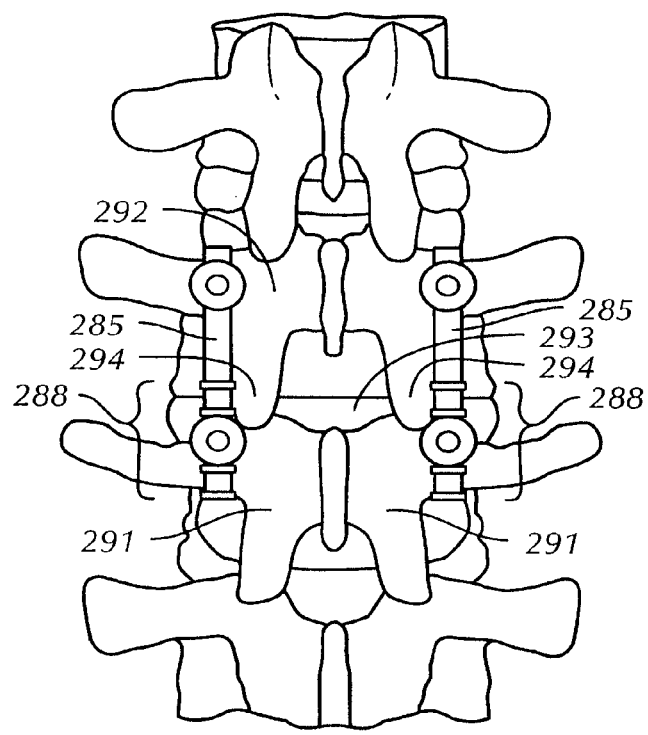
FIG. 53 illustrates two flexible connection units as shown in FIG. 52 attached to a patient's spine, in accordance with one embodiment of the present invention.

FIG. 53 illustrates the position of two connection units 284 after they have been implanted and secured to respective vertebrae of the spine. For each connection unit 284, the metal hybrid spacer 288 is fixed to the inferior vertebra 291, and end portion 285 is fixed to the superior vertebra 292. As shown in FIG. 53, the connection unit 284 provides allows for flexibility that takes into account the natural and anatomical motion of the spine. Because the invertebral disc 293 and facet joint 294 are closer to the pedicle of the inferior vertebra 291 than the pedicle of the superior vertebra 292, the flexible portion of the connection unit 284 provided by metal hybrid spacer 288, when it is secured to the inferior vertebra 291, is located off-center at or near the level of the natural joint in the spine, namely, the level of the intravertebral disc 293 and the facet joints 294. This flexibility at the level of the natural joint allows for natural and anatomically correct motion of the spine.

Figure 54:
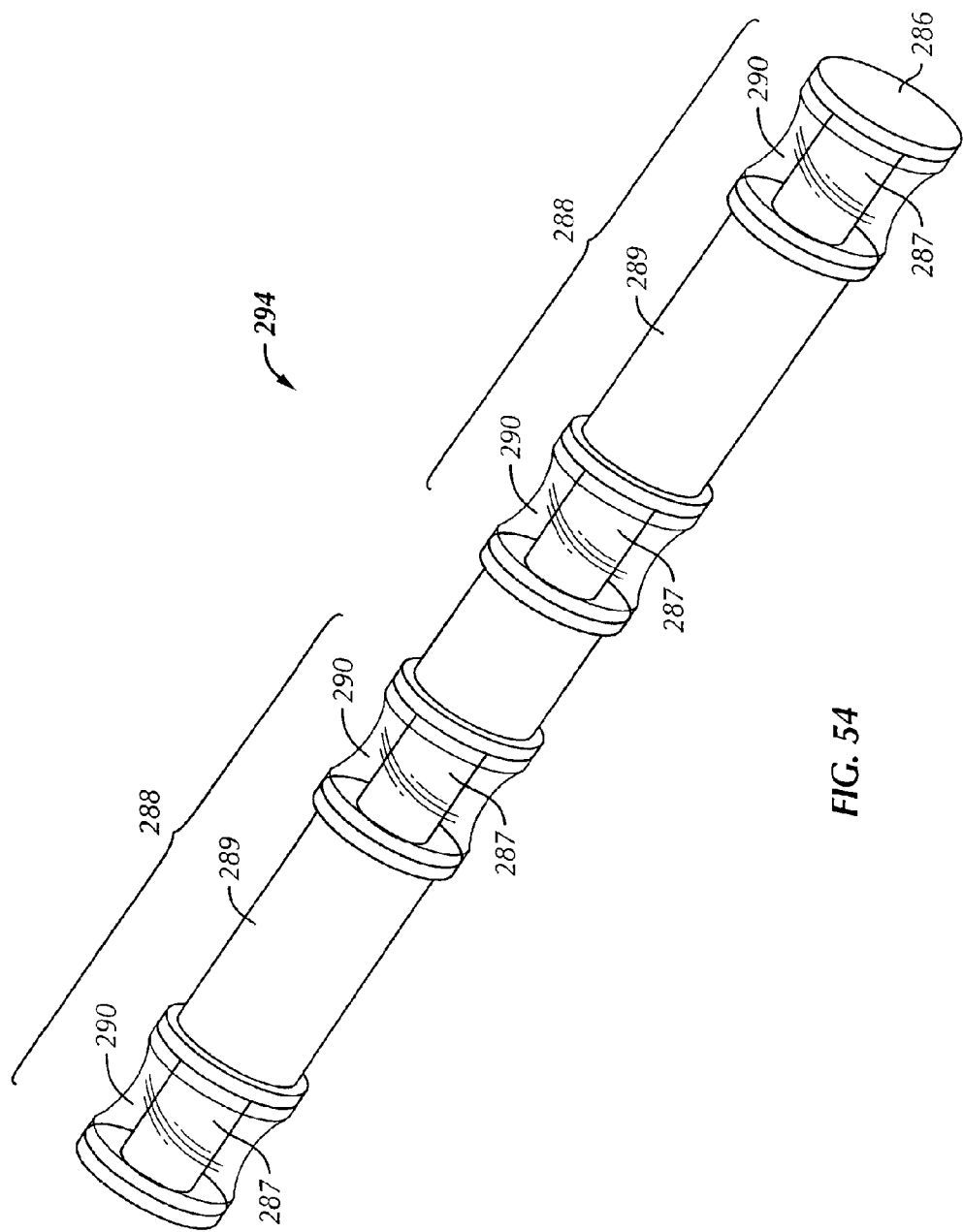
FIGS. 54-55 illustrates additional embodiments of a flexible connection unit having at least one spacer and an elastomer cladding, in accordance with the invention.

Of course, if flexibility is desired at additional areas this may be achieved by duplicating the metal-hybrid spacer 288 and connecting member 287 at the opposite end of the connection unit 294 as shown in FIG. 54. Connection unit 295 is configured to be retained by respective securing members attached to both spacers 288. The spacers 288 in connection unit 295 may be longer than the spacer 288 in connection unit 284 so that variability in the distance between vertebrae may be accommodated. In further embodiments, the connection units described above can be extended to stabilize two or more joints or spinal motion segments between three or more adjacent vertebrae, and affixed to respective vertebrae by three or more securing members (e.g., pedicle screws). Thus, in one embodiment, a connection unit includes a plurality of metal-hybrid spacers 288 for providing flexible stabilization to a plurality of joints or spinal motion segments. Additionally, the metal-hybrid spacers 288 may be alternated with rigid end portions 285 in any order or combination as needed by the surgeon. In this way, a hybrid multi-level or multi-spine segment connection unit may be designed, wherein each segment of the connection unit can provide a desired level of flexibility suited for each respective pair of inferior and superior vertebrae to be stabilized. For example, a first section of the connection unit that stabilizes a first pair of vertebrae may be very rigid, while a second section of the connection unit that stabilizes a second pair of vertebrae may be more flexible when compared to the first section. Numerous desired combinations of sections may be achieved to create a hybrid multi-level or multi-segment connection unit, in accordance with the present invention.

Figure 55:
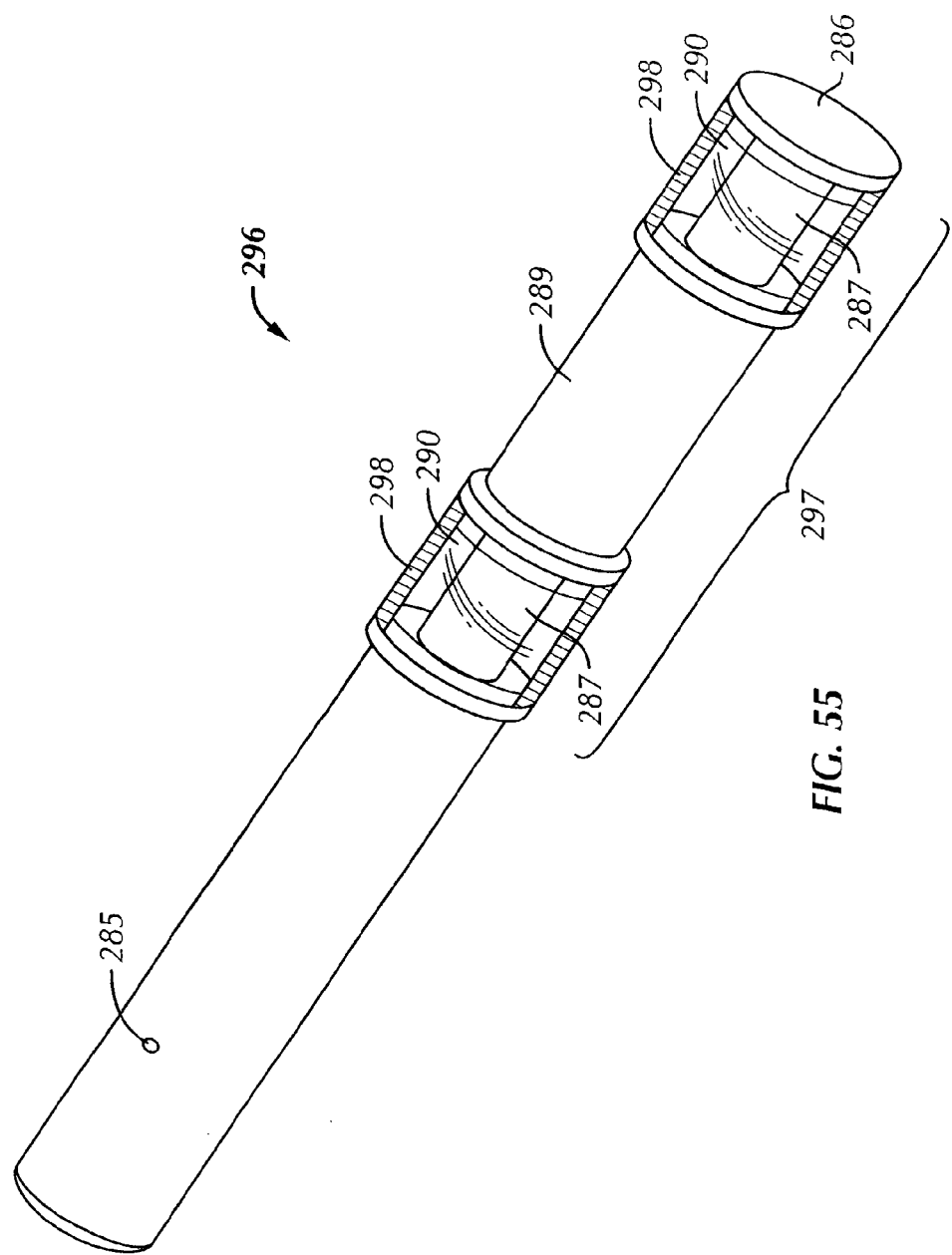

In various embodiments, the flexible member 287 as shown in FIGS. 52, 54 and 55 may be a solid member of rigid material, such as a biocompatible metal, preferably the same material as end portions 285 and 286 integrally formed with end portion 285 and permanently fixed to end portion 286. Alternatively, connecting member 287 may be a wire, plurality of wires, braided cable or other structure for connecting end portions 285 and 286. It will be clear to one skilled in the art that the structure, length and diameter of the connecting member will affect the flexibility of the connection unit 284. Similarly, the metal-hybrid spacer 288 may be made of a biocompatible metal, preferably the same material as end portions 285 and 286, and a biocompatible elastomer, for example, silicone or polyurethane and preferably polycarbonate urethane. The metal-hybrid spacer 288 is shown to be of substantially the same outside diameter as the rigid end portions 285 and 286. Alternatively, the elastomer part of the spacer 290 may be smaller or larger in diameter, or may be variable in diameter. It will be clear to one skilled in the art that the flexibility of the connection unit 284 may be changed by the selection of the cladding material and varying its dimensions.

The non-metal or elastomer portion 290 of the metal-hybrid spacer 288 may be attached to the surfaces of the respective end portions 285 and 286, the metal spacer 289 and/or the flexible member 287 by a variety of methods including those shown in FIGS. 50A-50D. As shown in FIGS. 52-55, the elastomer cladding 290 maintains the metal spacer 289 in a substantially fixed position with respect to the end portions 285 and 286, while allowing some relative movement of the spacer 289 when external forces cause the cladding to bend or compress in any direction. Thus, in one embodiment, the flexibility of the connection unit 284 is substantially limited by the compressibility of the elastomer part 290 of the hybrid spacer 288, which may be compressed in various directions by the motion of the metal part 289 of the spacer 288, when the metal part 289 is fixed to the vertebral bone by a securing member 2.

FIG. 55 illustrates an embodiment of a connection unit 296 with a metal-hybrid spacer 297 comprised of more than two different materials. The spacer 297 has a metal part 289 and an elastomer part 290 as described in FIG. 52 and an additional bio-absorbable part 298, shown external to the elastomer part 290. The bio-absorbable part 298 of the metal-hybrid spacer is configured to substantially extend from each end of the metal part of the spacer 289 to the nearest end of respective rigid end portions 285 and 286 and to restrict motion of the metal part 297, until bio-absorbable part 298 is softened or degraded in the body. The bio-absorbable part of the spacer 298 may be comprised of at least one material selected from a group of known bio-absorbable materials consisting of: polylactic acid, polyglycolic acid, polyglactic acid, polydioxanone, polyglyconate, calcium sulfate, calcium phosphate and combinations thereof. Other known bio-absorbable materials, and even those that will be discovered in the future, may be utilized in accordance with the present invention.

In one embodiment, the connection unit 296 can be used after a spinal fusion procedure. In many cases, it is desirable to rigidly secure the spine with implanted devices during the period immediately postoperative to a fusion procedure, in order to allow the surgically placed bone graft to heal and effectively fuse the adjacent vertebrae together. After fusion is successfully achieved, it is desirable to remove the implanted devices to allow the bone graft to stabilize the spine independently. This creates load on the graft site and healthy remodeling of the bone graft for secure fixation long term. However, it is highly undesirable to perform a second surgery to remove the implanted devices. The connection unit 296 in FIG. 55 initially provides a more rigid stabilization following spinal fusion and then through a natural process the bio-absorbable portion 298 of the connection unit 296 degrades and becomes absorbed by the body, thereby reducing the stiffness of the connection unit 296 and allowing the bone graft to share a greater percentage of the load to stabilize the spine long term. The flexible connection unit 296 therefore allows a surgeon to transition the level of flexible stabilization from a first more rigid state to a second less rigid state, with only one surgical procedure. Needless to say, the elimination of a surgical procedure is a tremendous advantage to patients both from a health standpoint and a financial one.

The flexible connection unit 296 can be advantageously utilized in any situation where it is desirable to provide varying levels of stability. Additionally, the relative amount and type of bio-absorbable material incorporated into the connection unit 298 can be varied to alter the initial stiffness of the connection unit 296 and the time required to fully absorb all of the bio-absorbable portion(s) 298. In one embodiment, two or more different types of bio-absorbable materials having different stiffness characteristics and/or absorption times can be utilized to provide transitions from multiple levels of stiffness. In a further embodiment, a connection unit configured to stabilize multiple spine segments can incorporate bio-absorbable materials in one or more flexible portions of the connection unit to provide varying states of flexibility by various flexible portions of the multi-spine segment connection unit. Additionally, the bio-absorbable material 298 may be applied to completely encapsulate a flexible portion (e.g., the metal-hybrid spacer portion) of a connection unit, or simply cover select portions of the connection unit, or fill gaps, spaces and/or channels of the connection unit. In other words, the application of one or more bio-absorbable materials 298 can be implemented in various ways to achieve desired initial and final stiffness characteristics for one or more flexible portions of a connection unit. Additionally, it is not necessary to combine bio-absorbable claddings 298 with non-bio-absorbable claddings 290. Thus, in one embodiment, the elastomer cladding 290 of the connection unit 296 illustrated in FIG. 55 may be omitted altogether or replaced by the bio-absorbable cladding 298, or another bio-absorbable cladding (not shown) having different stiffness and/or degradation/absorption characteristics.

Figure 56:
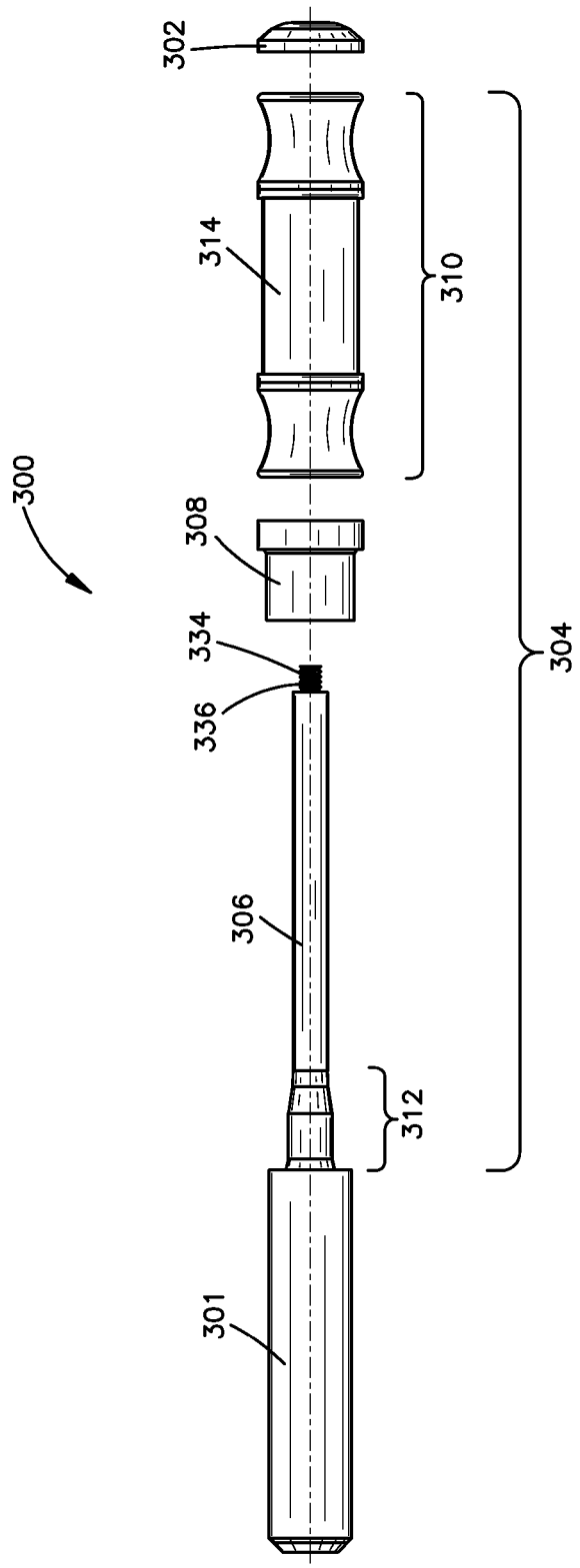
FIG. 56 illustrates an exploded view of a further embodiment of a flexible connection unit in accordance with the present invention.

FIG. 56 is an exploded view illustrating several features of a connection unit 300 in accordance with one embodiment of the present invention. The connection unit 300 has first and second end portions 301 and 302 and a middle portion 304 in which a flexible member 306 connects end portions 301 and 302 and traverses an axial hole in a collar 308 and an axial hole in a metal-hybrid spacer 310. The second end portion 302 is also referred to in this disclosure from time to time as the end cap 302. The flexible member 306 can be formed integrally with the first end portion 301, so that the first end portion 301 and a flexible member 306 are a rod-like element. In an alternative embodiment, the first end portion 301 and the flexible member 306 can be formed as two separate elements and secured together using any number of different securing methods, such as by use of adhesives, machine threads, welding, laser welding, press fitting, morse taper, or any other suitable method of securing presently known or that will be known in the future.

The first end portion 301 and the flexible member 306 may be designed in a number of different ways for providing a desired stability to a patient's back, for example, substantially equal to that of a normal back. As is appreciated, varying the physical characteristics of the first end portion 301 and flexible member 306, such as respective sizes and material composition, can change the flexibility characteristics of the connection unit 300. For example, the first end portion 301 of the connection unit 300, as shown in FIG. 56, has a larger diameter than the flexible member 306. However, the dimensions need not be so limited, as other embodiments can have other dimensions such having the first end portion 301 and flexible member 306 with the same diameter or the flexible member 306 having a larger diameter than the first end portion 301. The first end portion 301 can also be rigid, semi-rigid or flexible. In one embodiment, the first end portion 301 is flexible, but less flexible than the flexible member 306. In addition, the first end portion 301 and the flexile member can be made of the same type of material or each can be made of different materials. In one embodiment, the first end portion 301 and flexible member 306 can be made of any suitable biocompatible metal, metal-hybrid or synthetic material discussed above with respect to the end portion 285 and flexible middle portion 287 described with reference to FIG. 52. It is also understood that the first end portion 301 and the flexible member 306 can be made in accordance with the design and material specifications of any of the embodiments previously discussed.

Further to FIG. 56, a transition area 312 can be provided where first end portion 301 and the flexible member 306 connect. The transition area 312 can be tapered or stepped so that the change in diameter between the first end portion 301 and the flexible member 306 is gradual. This can reduce or eliminate stress points caused by a sudden change in diameter, as is understood by those skilled in the art. Thus, the transition area 312 can provide further strength to the device by, for example, reducing the stress associated with a change in diameter between the first end portion 301 and the flexible portion. In one embodiment, the transition area 312 is integral with the first end portion 301 and the flexible member 306 and is made of the same material as the first end portion 301 and the flexible member 306.

Figure 57:
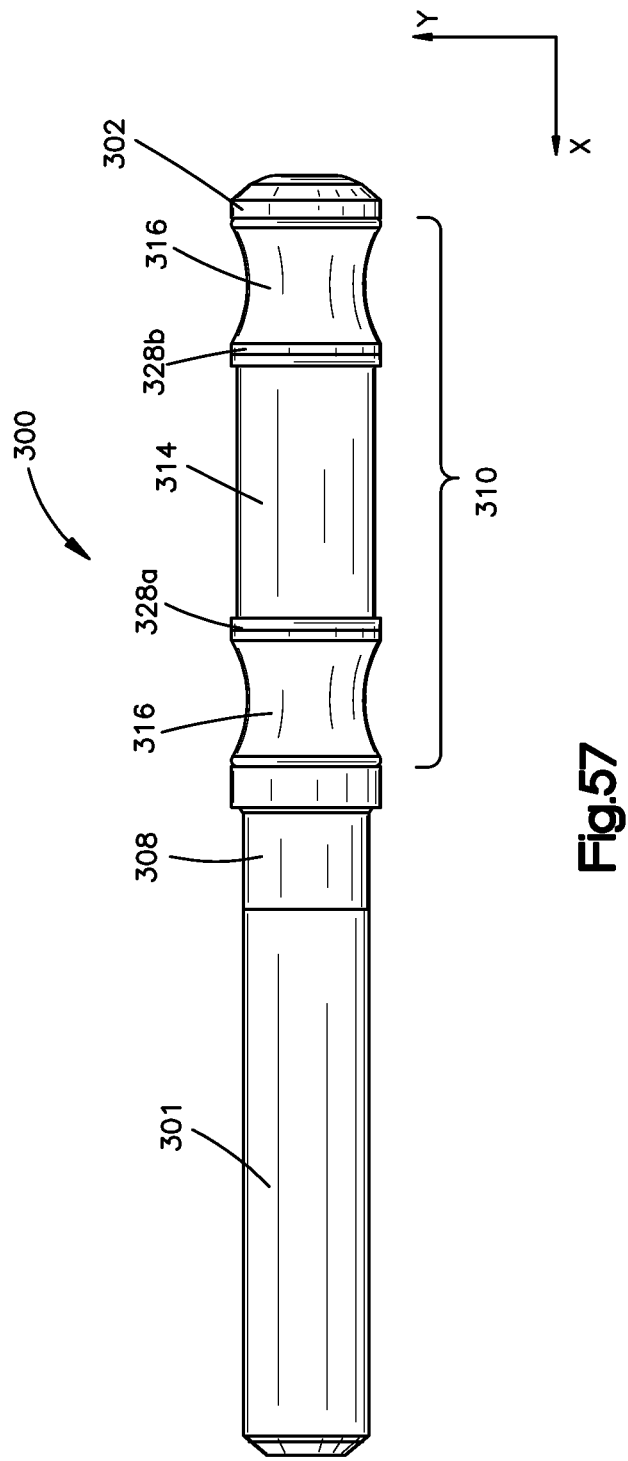
FIG. 57 illustrates the flexible connection unit of FIG. 56 in an assembled state in accordance with an embodiment of the present invention.

With reference to FIG. 57, which shows the connection unit 300 of FIG. 56 in an assembled state, the collar 308 can be positioned between the first end portion 301 and the metal-hybrid spacer 310 and over some or all of the transition area 312 (FIG. 56). The collar 308 can provide an even surface for an end of the metal-hybrid spacer 310 to abut against; as opposed to the spacer 310 contacting the transition area 312, which can provide an uneven contact surface. In one embodiment, the collar 308 is made of the same type of material as the first end portion 301 and the flexible member 306 discussed above, but may comprise a different type of material in other embodiments. Moreover, the collar 308 can be secured to the first end portion 301 or the collar 308 can be separate and "float" between the first end portion 301 and the spacer 310. If secured, the collar 308 can be secured to the first end portion 301 using any number of different securing methods, such as by use of adhesives, machine threads, welding, laser welding, press fitting, morse taper, or any other suitable method of securing presently known or known in the future.

Further to FIG. 56, the metal-hybrid spacer 310 can be similar to the metal-hybrid spacer 310 of FIG. 52. The metal-hybrid spacer 310 can include at least one metal ring element 314 and at least one resilient element or portion 316. As best seen in the cross-sectional view of the spacer 310 shown in FIG. 58, the resilient element 316 can comprise multiple sections: a first bumper section 318 located on one side of the metal ring element 314, a second bumper section 320 located on the other side of the metal ring element 314, and an internal bumper section 322 located between the first and second bumpers 318 and 320 and substantially or completely inside the core of the metal ring element 314. In one embodiment, each of the bumper sections 318, 320 and 322 is formed integral with one another. However, in other embodiments, the bumper sections 318, 320 and 322 can be non-integral or separate. In alternative embodiments, the resilient element 316 can comprise more that three bumper sections or fewer than three bumper sections for providing desired flexibility characteristics to the connection unit 300.

The resilient element 316 can consist of any of a variety of medical grade elastomers, including, for example, silicone, polyurethane, polycarbonateurethane and silicone-urethane copolymers. It is understood that the resilient element 316 can be made from other suitable non-metal materials such as those described above. In alternative embodiments, the resilient element 316 may be implemented as a helical metal spring, disc spring, wave spring or other resilient structures. The resilient element 316 can be formed on the sides of and within the core of the metal ring element 314 using a variety of techniques that are well known in the art. In one technique, a thermoplastic or thermosetting resin can be injected into a heated mold, while the metal ring element 314 is affixed within a mold. An advantage of this injection molding process is that it can accommodate elastomer materials that are not of sufficiently low viscosity for application by alternate means at room temperature and pressure. As is understood, the mold can be shaped to form the hollow axial core of the spacer 310, or the hollow axial core can be formed by cutting out elastomer after the molding process is finished. A further advantage of injection molding is that the shape of the exterior of the cladding is determined by the shape of the mold that is used. Alternative molding techniques include compression molding and transfer molding.

In accordance with one embodiment, the stiffness of one of the bumper sections 318, 320 or 322 can be different from one or more of the other bumper sections 318, 320 or 322. Specifically, the stiffness of each bumper can be independently tuned by adjusting the physical properties of the bumper. For example, as is appreciated by those skilled in the art, the stiffness can be modified by changing the length, diameter, ratio of diameters, placement and material composition of one or more of the bumper sections. Additionally, the resistance provided by bumper regions may be adjusted by changing the length of the spacing provided for the resilient element between the first and second ends of the connection unit, thereby compressively biasing the resilient element. In one embodiment, the length of the spacing provided between the first and second ends may be adjusted by selecting a collar 308 of desired dimensions. Other techniques for adjusting this length would be readily apparent to those of skill in the art.

Deformation zones can also be provided for controlling the deformation of the resilient element 316. Deformations zones can have the desired effect of providing a more predictive and consistent response to compressive forces. For example, because most buckling of an resilient element 316 having deformation zones occurs at the deformation zones, it can be easier to predict the resilient element's 316 response. In contrast, an absence of deformation zones can result in deformation at any number of different locations about the elastomer portion 316. For example, a resilient element 316 not having a defined deformation zone may buckle at one location in response to a compressive force that is applied a first time, but buckle at a different, second location when the exact same compressive force is applied a second time. As is appreciated by those skilled in the art, buckling at different locations can provide different responses to the same compressive force. Consequently, it can be difficult to predict the response of an elastomer portion that does not have predefined deformation zones.

In one embodiment of the present invention, predefined deformation zones are formed by contouring the shape of the resilient element 316 so that it buckles at the predefined deformation zones. In the embodiment shown in FIG. 58, the first bumper 318 is contoured to have a reduced diameter its center, thereby defining a first predefined deformation zone 324, and the second bumper is contoured to have a reduced diameter its center, thereby defining a second predefined deformation zone 326. Accordingly, the resilient element 316 is configured to buckle at the first deformation zone 324 when ring element 314 translates in, for example, a longitudinal axial direction toward the first deformation zone 324, and buckle at the second deformation zone 326 when the ring element 314 translates in, for example, a longitudinal axial direction toward the second deformation zone 326.

Similar to the metal part 289 referenced in FIG. 52, the metal ring element 314 can be configured to be accepted and retained by a securing member such as the securing member 2 described with reference to FIG. 3. To help properly position the ring element 314 in a securing member, shoulders 328a and 328b can be provided at respective ends of the ring element 314, as best seen in FIGS. 57 and 58. For example, positioning the head 16 (FIG. 3) of the securing member 2 between the shoulders 328a and 328b can provide assurance that the ring element 314 is positioned correctly in the securing member 2.

In one embodiment, the shoulders 328a and 328b may also be sized so that a fastening member, such as the threaded nut 22 or the cap member 26 of FIG. 3, cannot be fastened to a screw mount, such as head 16 of FIG. 3, if the shoulders 328a and 328b are not positioned properly. For example, the shoulders 328a and 328b may be required to be positioned on either side of the screw head 16; otherwise, if one of the shoulders 328a or 328b is inside the screw head 16, then the nut 22 cannot be properly inserted into the head 16 because the shoulder 328 extends at least partially into the area of the head 16 configured to receive the nut 22. As a result, a person securing the ring element 314 to the securing member 2 should realize that the ring element 314 is not positioned properly in the head 16 if the nut 22 cannot be properly fastened to the securing member 2. Thus, if unable to fasten the nut 22, the person installing the connection unit 300 should reposition the ring element 314 within the head 16.

With further reference to FIG. 58, in particular the magnified view of the spacer 310, the interior edges of the ring element 314 may be trumpeted. As used herein, the term trumpeted can be defined as rounded out or flared. In one embodiment, the inner diameter of the ring element 314 is substantially constant in the center portion of the metal ring element 314, but increases (i.e., is trumpeted) near the ends of the ring element 314. In a further embodiment, the inner diameter is smallest at the center and gradually increases toward the ends of the ring element 314 so that the longitudinal cross-sectional shape of the interior surface of the ring element 314 has a constant radius of curvature.

Trumpeting the ends of the ring element 314 can provide several benefits. First, trumpeting the ends can provide more surface area between the ring element 314 and the resilient element 316 than if the inner surface of the ring element 314 had, for example, sharp corners at the edges. The additional surface area can result in less contact stress, which can reduce the likelihood of the ring element 314 cutting the resilient element 316, especially at the edges of the ring element 314. Trumpeting the ends can also facilitate toggling rotation of the ring element 314. Toggling rotation permits a more natural motion of the spine, and is discussed in more detail below.

Figure 59A:
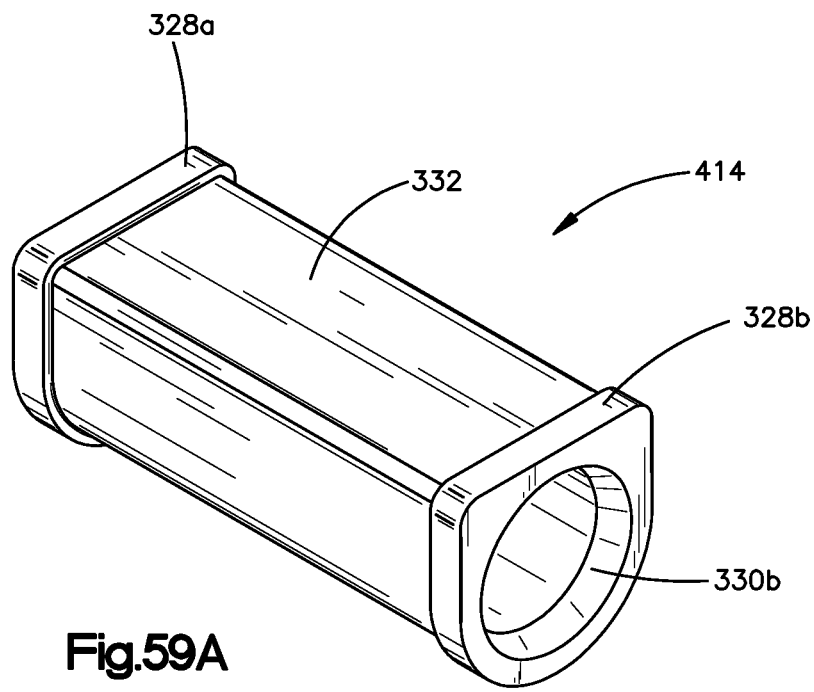
FIGS. 59a-b illustrate a perspective view and front cross-sectional view of an embodiment of a D-ring metal ring in accordance with the present invention.
Figure 59B:
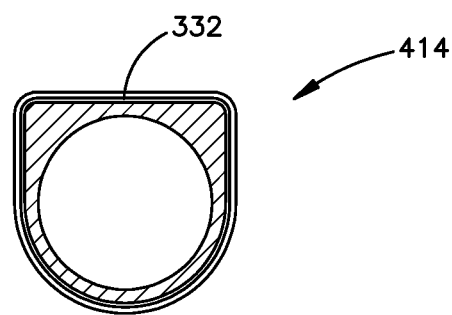

FIGS. 59a and 59b depict a further embodiment of a ring element 414 in accordance with the present invention. FIG. 59a is a perspective view of the ring element 414 and FIG. 59b is a front cross-sectional view of the ring element 414. As shown, the ring element 414 is similar to the ring element 314 shown in FIGS. 56-58, except that the ring element 414 has a generally D-like cross-sectional shape. The ring element 414 is referred to in this disclosure from time to time as a "D-ring." Also, similar to the ring element 314, the D-ring 414 can have trumpeted ends 330 as well as shoulders 328a, 328b. It is believed that the cross-sectional shape of the D-ring 414 can distribute a compressive load resulting from a locking cap (e.g. nut 22 of FIG. 3) compressing down onto a flat top surface 332 of the ring 414 better than most other configurations. The D-ring's 414 ability to better distribute this type of compressive load can reduce or altogether avoid localized buckling, thereby enabling higher locking torques and the use of thinner ring walls.

Referring back to FIG. 56, the end cap 302 is fastened to an end of the flexible member 306 and retains the collar 308 and the spacer 310 between the first end 301 and the end cap 302. In one embodiment, the end cap 302 has an axial core with internal threads (not shown). The end cap 302 can be secured to the flexible member 306 by threading the internal threads with corresponding external threads 334 located at an end of the flexible member 306. Once threaded together, an outside seam (not shown) between the flexible member 306 and the end cap 302 can be laser welded to further secure the end cap 302 to the flexible member 306. In other embodiments, the end cap 302 may be secured to the first end portion 301 using any number of different securing methods, including but not limited to press fitting, use of adhesives, swaging and morse taper.

With reference to FIG. 56, a shoulder 336 can be formed on the flexible member 306 for preventing the end cap 302 from traveling along the longitudinal axis of the flexible member 306 past a predetermined distance when being secured to the flexible member 306. Advantageously, the predetermined distance can be associated with a desired preload on the spacer 310. This is because when assembling the connection unit 300, the resilient element 316 of the spacer 310 may be compressed to some extent after the end cap 302 is attached. This may happen, for example, if the spacer 310 in its uncompressed state has a longitudinal length that is longer than the length between the collar 308 and the end cap 302. Accordingly, the amount the spacer 310 is compressed after the end cap 302 is attached can correspond to a preload amount.

In one embodiment, the spacer 310 having a preload provides a first level of resistance to a longitudinal movement of the metal ring 314 until the preload is overcome. Once the preload is overcome, the spacer 310 provides a second level of resistance, which is less than the first level of resistance.

Because it is believed that most people dealing with spine pain typically feel most the their pain during an initial range of motion of the spine, but do not feel as much pain after the initial range of motion, the spacer 310 can be configured with a preload that provides more support (e.g. more resistance) during the initial, painful range of motion and less support (e.g. less resistance) after the initial range of motion.

As described above, in one embodiment, the spacer 310 is not affixed to the collar 308, end cap 302 or of flexible member 306 and, therefore, can separate from the end cap 302 or collar 308 after a preload associated with the spacer 310 has been overcome. Accordingly, in this embodiment, the spacer 310 only resists compression and does not resist motion by tension or elongation. By configuring the spacer 310 to resist compression only, it is believed that the connection unit 300 can provide better dynamic support during motion of the spine.

Referring to FIG. 57, when end portion 301 and spacer 310 are retained by respective securing members 2 (FIG. 2), for example, and affixed to adjacent vertebrae, the connection unit 300 provides stability while simultaneously permitting motion to the vertebrae in six degrees of freedom (i.e., x-axis, y-axis, z-axis, pitch, roll and yaw). Movement of the metal ring element 314 in a pitch, roll, yaw or combination thereof may also be referred to in this disclosure as a "toggling" motion. Although the end portions 301 and 302 substantially limit the motion of the spacer 310 in the longitudinal axial direction, the compressibility and elasticity of the resilient element 316 on both sides of the metal ring element 314 and between the metal ring element 314 and the flexible member 306 allows for stabilized motion of the metal ring element 314 relative to the end portions 301 and 302 and/or flexible member 306 in each of the six degrees of freedom while also providing a resistance and stability of motion in each of the six degrees of freedom. Thus, in one embodiment, the connection unit 300 provides a greater range of dynamically stabilized motion. Additionally, in one embodiment, the resilient element 316 permits sliding of the metal-hybrid spacer 310 on flexible member 306, thereby providing further movement of the metal ring element 314 in the longitudinal axial direction. In one embodiment, the metal hybrid spacer 310 floats between end portions 301 and 302 (i.e. the spacer 310 is not affixed to respective ends portions 301 and 302 or collar 308) so that the metal-hybrid spacer 310 can be physically separated from the end cap 302 or collar 308 in response to a sufficient longitudinal axial force.

Figure 60:
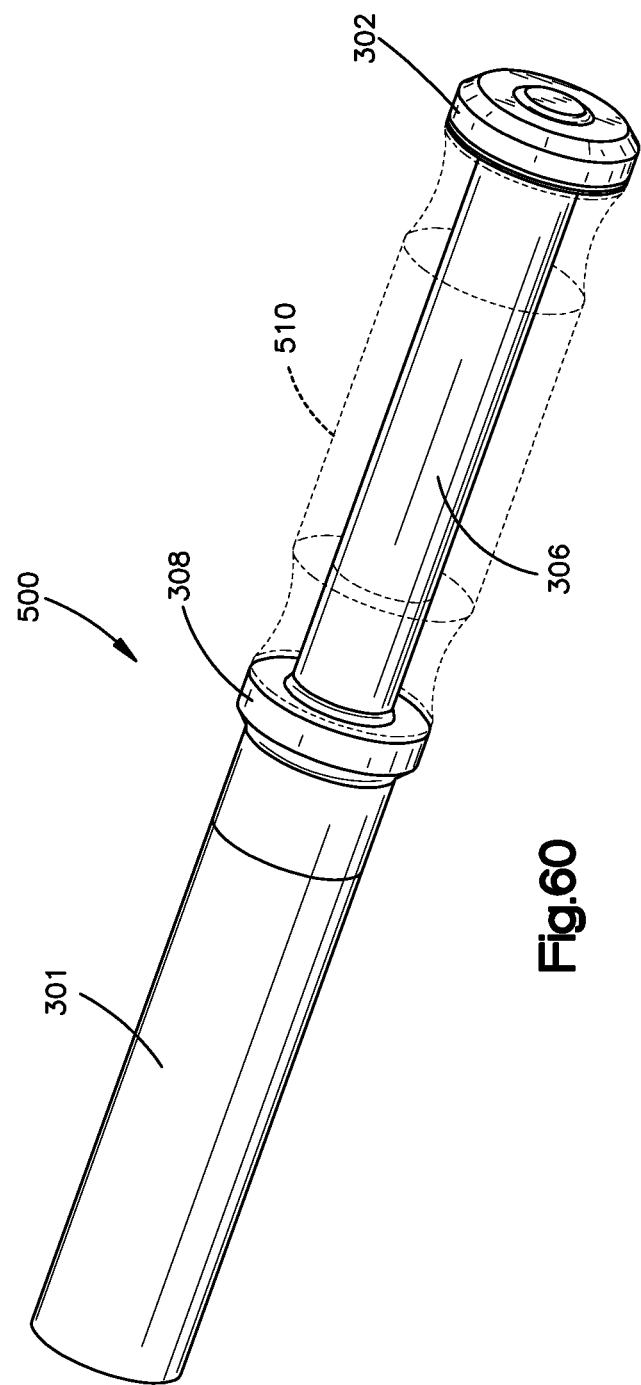
FIG. 60 illustrates a flexible connection unit in accordance with one embodiment of the invention.

FIG. 60 illustrates an alternative embodiment of a connection unit 500 in accordance with the present invention. Connection unit 500 is similar to connection unit 300 of FIG. 56, except that the spacer 310 is comprised of single resilient element 510 rather than the metal-hybrid spacer 310 shown in FIG. 56. In this embodiment, the single resilient element 510 is configured to be directly received within a correspondingly shaped securing head of a bone securing member (e.g., ring-shaped head of a pedicle screw). Thus, the securing head of the bone securing member assumes the functionality of the ring element 314 of the metal-hybrid spacer. When the resilient element 510 is received within and secured to the securing head of a bone securing member, the resilient element 510 functions to provide dynamic resistance against relative motion of the bone securing member in at least five degrees of freedom, excluding rotation about a longitudinal axis of the connection unit. In an alternative embodiment, the resilient element 510 provides sufficient friction against the flexible member 306 located within the axial channel of the resilient element 510 so as to provide resistance to motion of the bone securing member in all six degrees of freedom.

Figure 61:
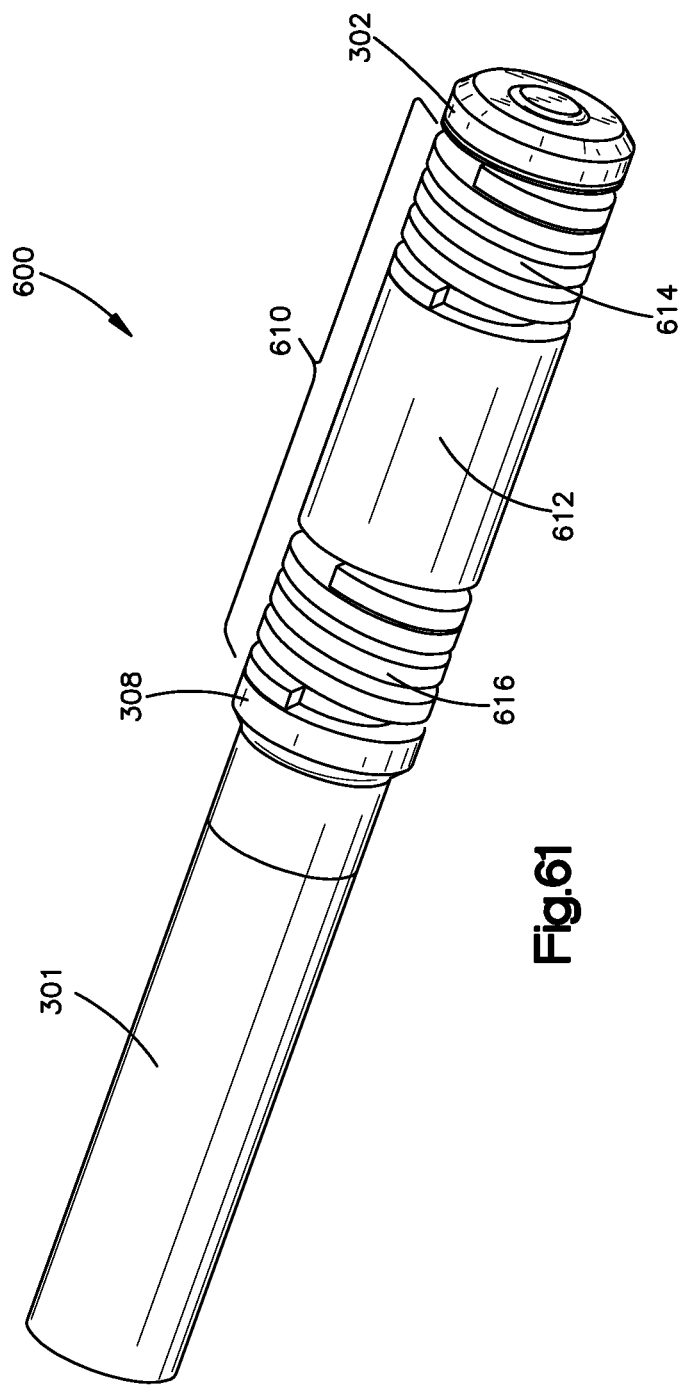
FIG. 61 illustrates a flexible connection unit in accordance with one embodiment of the invention.

FIG. 61 is a perspective view of a flexible connection unit 600, in accordance with another embodiment of the invention. Connection unit 600 is similar to connection units 300 and 500 of FIGS. 56 and 60, respectively, except that the spacer 610 of connection unit 600 includes a ring element 612 interposed between resilient spring elements 614 and 616. The ring element 612 is configured to be engaged with a securing head of a bone securing member (e.g., pedicle screw) and the resilient spring elements 614 and 616 provide resistance to longitudinal movement (e.g., sliding) of the ring element 612 along a longitudinal axis of the flexible element 306 (FIG. 56). As shown in FIG. 61, the spacer 610 is positioned between a first end 301 and a second end 302, comprising end cap 302, as described above. A collar 308 is interposed between the spacer 610 and the first end 301. As discussed above, the collar 308 can provide an even surface for an end of the metal-hybrid spacer 310 to abut against; as opposed to the spacer 310 contacting a transition area 312 (FIG. 56), which can provide an uneven contact surface.

Various embodiments of the connection units discussed in this disclosure can have several other advantages. First, some of the embodiments have a similar profile to conventional spinal fixation devices consisting of a metal rod secured to vertebrae via securing members. Because embodiments of connection units in accordance with the present invention can have a similar profile to a metal rod, the embodiments disclosed herein can have the advantage of being installed using conventional spinal fixation instrumentation. Furthermore, the low profile associated with many of the connection unit embodiments occupies less room in the patient, thereby resulting in less interference with the patient's range of motion, among other things.

Various embodiments of the invention have been described above. However, those of ordinary skill in the art will appreciate that the above descriptions of the preferred embodiments are exemplary only and that the invention may be practiced with modifications or variations of the devices and techniques disclosed above. Those of ordinary skill in the art will know, or be able to ascertain using no more than routine experimentation, many equivalents to the specific embodiments of the invention described herein. Such modifications, variations and equivalents are contemplated to be within the spirit and scope of the present invention as set forth in the claims below.

What is claimed is:

1. A flexible connection unit for use in a spinal fixation device, the flexible connection unit comprising:
   a longitudinal member having a first end portion, a second end portion and a flexible member interposed at least partially between the first and second end portions, at least one of the first end portion or the second end portion configured to be engaged by a first bone securing member; and
   a spacer located at least partially between the first and second end portions, the spacer comprising:
   (1) a rigid ring element having a length and having a first inner bore extending the length of the ring element; and
   (2) a resilient element including a first resilient portion, a second resilient portion and a connecting portion, the first resilient portion is configured to abut the first end portion, the second resilient portion is configured to abut the second end portion, and the connecting portion extends through the first inner bore connecting the first resilient portion to the second resilient portion such that the ring element is spaced apart from the first and second end portions, and the resilient element further defines a second inner bore configured to receive the flexible member such that the flexible member extends through the first and second inner bores.

2. The flexible connection unit of claim 1 wherein at least one interior edge of the ring element is rounded.

3. The flexible connection unit of claim 2 wherein both interior edges of the ring element are rounded.

4. The flexible connection unit of claim 1 wherein the ring element has a circular cross-sectional shape.

5. The flexible connection unit of claim 1 wherein a cross-sectional profile of the flexible member is smaller than a cross sectional profile of at least one of the first or second end portions.

6. The flexible connection unit of claim 1 wherein the resilient element is made of a material comprising organic polymer, elastomer, naturally occurring resin, or composite material.

7. The flexible connection unit of claim 1 wherein the connection unit is configured in the profile of a cylindrical rod.

8. The flexible connection unit of claim 1 wherein the spacer is made of a material comprising metal, metal alloy, organic polymer, naturally occurring resin, thermoplastic or composite material.

9. The flexible connection unit of claim 1 wherein the ring element is made of a material comprising metal, metal alloy or composite material.

10. The flexible connection unit of claim 1 wherein the flexible member comprises a flexible wire or bundle of wires.

11. The flexible connection unit of claim 6 wherein the resilient element comprises elastomeric cladding.

12. The flexible connection unit of claim 1 wherein the first and second end portions of the longitudinal member, the ring element and the flexible member each are made of a material comprising metal or metal alloy.

13. The flexible connection unit of claim 12 wherein the resilient element comprises elastomeric cladding.

14. The flexible connection unit of claim 1 wherein the flexible member is positioned axially through the spacer and at least a portion of the first or second end portions.

15. The flexible connection unit of claim 1 wherein the resilient element is concentric with the flexible member.

16. The flexible connection unit of claim 1 wherein the flexible member is eccentrically located in an axial cavity of the at least one spacer.

17. The flexible connection unit of claim 1 wherein the flexible member is physically separated from both the first end portion and the second end portion.

18. The flexible connection unit of claim 17 wherein the flexible member is surrounded with an elastomer.

19. The flexible connection unit of claim 18 wherein the flexible member is formed of at least one wire and the at least one wire is axially slidable within a pre-formed extruded elastomer.

20. The flexible connection unit of claim 1 wherein the flexible member is in contact with at least one of the first and second end portions.

21. The flexible connection unit of claim 1 wherein the flexible member is fixed with respect to at least one of the first and second end portions.

22. The flexible connection unit of claim 1 wherein the flexible member is fixed at both the first end portion and the second end portion.

23. The flexible connection unit of claim 1 wherein the ring element circumferentially surrounds the resilient element.

24. The flexible connection unit of claim 1 wherein the spacer comprises a plurality of ring elements and the resilient element comprises an elastomer.

25. The flexible connection unit of claim 9 wherein the resilient element is polycarbonate urethane.

26. The flexible connection unit of claim 1, wherein the resilient element is configured to abut the first and second end portions of the longitudinal member such that the resilient element is at least partially disposed within a cavity of the first or second end.

27. The flexible connection unit of claim 1, wherein the resilient element is configured to abut the first and second end portions of the longitudinal member such that the first or second end portion is at least partially disposed within a cavity of the resilient member.

* * * * *